United States Patent
Herickhoff et al.

(10) Patent No.: US 11,028,368 B2
(45) Date of Patent: Jun. 8, 2021

(54) SYSTEM AND SUBSTANCES FOR CRYOPRESERVATION OF VIABLE CELLS

(71) Applicant: Membrane Protective Technologies, Inc., Fort Collins, CO (US)

(72) Inventors: Lisa A. Herickhoff, Fort Collins, CO (US); Patrick D. Burns, Fort Collins, CO (US); Nicole R. White, Red Bank, TN (US); James A. Herickhoff, Fort Collins, CO (US)

(73) Assignee: Membrane Protective Technologies, Inc., Fort Collins, CO (US)

( * ) Notice: Subject to any disclaimer, the term of this patent is extended or adjusted under 35 U.S.C. 154(b) by 0 days.

(21) Appl. No.: 14/385,471

(22) PCT Filed: Mar. 11, 2013

(86) PCT No.: PCT/US2013/030222
§ 371 (c)(1),
(2) Date: Sep. 15, 2014

(87) PCT Pub. No.: WO2013/138239
PCT Pub. Date: Sep. 19, 2013

(65) Prior Publication Data
US 2015/0037783 A1 Feb. 5, 2015

Related U.S. Application Data

(60) Provisional application No. 61/685,224, filed on Mar. 14, 2012.

(51) Int. Cl.
| | |
|---|---|
| *C12N 1/04* | (2006.01) |
| *C12N 5/09* | (2010.01) |
| *A01N 1/02* | (2006.01) |
| *C12N 5/04* | (2006.01) |
| *C12N 5/073* | (2010.01) |
| *C12N 5/0735* | (2010.01) |
| *C12N 5/075* | (2010.01) |
| *C12N 5/076* | (2010.01) |
| *C12N 5/0797* | (2010.01) |
| *C12N 5/071* | (2010.01) |
| *C12N 5/077* | (2010.01) |
| *C12N 5/0775* | (2010.01) |

(52) U.S. Cl.
CPC ......... *C12N 5/0693* (2013.01); *A01N 1/0221* (2013.01); *A01N 1/0278* (2013.01); *C12N 1/04* (2013.01); *C12N 5/04* (2013.01); *C12N 5/061* (2013.01); *C12N 5/0603* (2013.01); *C12N 5/0606* (2013.01); *C12N 5/067* (2013.01); *C12N 5/0609* (2013.01); *C12N 5/0623* (2013.01); *C12N 5/0626* (2013.01); *C12N 5/0629* (2013.01); *C12N 5/0652* (2013.01); *C12N 5/0661* (2013.01); *C12N 5/0665* (2013.01); *C12N 5/0682* (2013.01); *C12N 5/0683* (2013.01); *C12N 2500/36* (2013.01)

(58) Field of Classification Search
CPC .... C12N 5/0693; C12N 1/04; C12N 2500/36; A01N 1/0278; A01N 1/0221
See application file for complete search history.

(56) References Cited

U.S. PATENT DOCUMENTS

| | | | |
|---|---|---|---|
| 6,368,786 B1 | 4/2002 | Saint-Roman et al. |
| 7,622,143 B2 | 11/2009 | Herickhoff et al. |
| 7,820,425 B2 | 10/2010 | Schenk |
| 7,838,210 B2 | 11/2010 | Ludwig et al. |
| 7,892,725 B2 | 2/2011 | Graham et al. |
| 8,202,558 B2 | 6/2012 | Herickhoff et al. |
| 2003/0077566 A1 | 4/2003 | Palasz et al. |
| 2006/0222724 A1 | 10/2006 | Herickhoff et al. |
| 2009/0123906 A1 | 5/2009 | Herickhoff |
| 2009/0186335 A1 | 7/2009 | Palasz et al. |
| 2011/0086336 A1 | 4/2011 | Herickhoff et al. |

FOREIGN PATENT DOCUMENTS

| | | |
|---|---|---|
| AU | 2013232381 | 12/2018 |
| EP | 1051907 A1 | 11/2000 |
| EP | 2033513 A1 | 3/2009 |
| EP | 2825635 B1 | 4/2020 |
| WO | 2006079205 A1 | 8/2006 |
| WO | 2007077560 A2 | 7/2007 |
| WO | 2009109550 A1 | 9/2009 |

(Continued)

OTHER PUBLICATIONS

Liposome Preparation. Avanti Polar Lipids, Inc. downloaded from avantilipids.com/tech-support/liposome-preparation on May 18, 2017. p. 1-6.*
Thiam et al. The Biophysics and Cell Biology of Lipid Droplets. Nat Rev Mol Cell Biol. Dec. 2013 ; 14(12): 775-786. (Year: 2013).*
Ujihira et al. Cryoprotective effect of low-molecular-weight hyaluronan on human dermal fibroblast monolayers. Cryo Letters. Mar.-Apr. 2010;31(2):101-11. (Abstract only) (Year: 2010).*
Tolman. The Effect of Droplet Size on Surface Tension. Journal of Chemical Physics. vol. 17, No. 3. p. 333-337 (Year: 1949).*

(Continued)

*Primary Examiner* — Taeyoon Kim
(74) *Attorney, Agent, or Firm* — Santangelo Law Offices, P.C.

(57) ABSTRACT

An improved cryopreservation process and substances can involve a cellular collection (1) in a cryopreservation fluid (4) that has been conditioned or treated (7) to enhance the cryopreservation process by adding (18) energy (19) such as in the surface energy of a substance in the cryopreservation fluid (4) prior to reducing energy for that same cryopreservation media for freezing. This can offer enhanced-postcryogenic viability of the cryopreserved structures or a more optimum cooling curve (22) for a specific cell type.

21 Claims, 5 Drawing Sheets

(56) References Cited

FOREIGN PATENT DOCUMENTS

WO          2013138239 A1      9/2013

OTHER PUBLICATIONS

Elodie Pillet et al. "Liposomes as an alternative to egg yolk in stallion freezing extender" Theriogenology, Los Altos, CA US. vol. 77, No. 2. Aug. 1, 2011, pp. 268-279.
Zeron, Y. et al. The effect of liposomes on thermotropic membrane phase transitions of bovine spermatoza and oocytes: implications for reducing chilling sensitivity. Cryobiology 45 (202) 143-152. Oct. 2, 2002.
Leong, et al. Minimising oil droplet size using ultrasonic emulsification. Ultrason. Sonochem 2009, 16(6):721-727.
PCT Application No. PCT/US13/030222, filed Mar. 11, 2013. Written Opinion dated May 28, 2013.
PCT Application No. PCT/US13/030222, filed Mar. 11, 2013. International Search Report dated May 28, 2013.
European Application No. 13760949.1, filed Oct. 29, 2014. European Search Report dated Aug. 21, 2015. 8 pages.
Graham, et al. Effect of several lipids, fatty acyl chain length and degree of unsaturation on the motility of bull spermatozoa after cold shock and freezing. Cryobiology 1987, 24 (1):42-52; Abstract.
Barnes, D. and G. Sato (1980) Methods for growth of cultured cells in serum-free medium. Anal., Biochem. 102:255-270.
Foote, R.H., C.C. Brockett and M.T. Kaproth (2002). Motility and fertility of bull sperm in 5 whole milk extender containing antioxidants. An Repro Sci 71:13-23.
Thompson, J. et al. Rate-controlled cryopreservation. In Karow AM (ed). Organ Preservation for Transplantation. 2nd edition. New York: Marcel Dekker 1981: 177-212 and modified and expanded by biocor.umn.edu/listing-of-protective-agents.
Parallel Australian Application No. 2013232381. Full Examination Report dated Aug. 17, 2017. 5 pages.
Lopez-Rodriguez, et al., Transient Exposure of Pulmonary Surfactant to Hyaluronan Promotes Structural and Compositional Transformation into a Highly Active State. J. Biol. Chem. Oct. 11, 2013; 288(41):29872-29881. Published online Aug. 27, 2013.
European Patent Application No. 13760949.1; Examination Report dated Mar. 22, 2018. 7 pages.
Canada Patent Application No. 2905242; Office Action dated Mar. 21, 2019, 6 pages.
European Patent Application No. 13760949.1, Provision of the minutes in accordance with Rule 124(4) EPC dated Oct. 31, 2019. 6 pages.
European Patent Application No. 13760949.1, Communication Under Rule 71(3) EPC dated Nov. 6, 2019. 72 pages.
Canadian Patent Application No. 2905243. Examiner Requisition dated May 1, 2020. 6 pages.
European Patent Application No. 13760949.1. Decision to Grant a European Patent Pursuant to Article 97(1) EPC, dated Mar. 19, 2020. 2 pages.
Tcholakova, Slavks et al; "Role of Surfactant Type and Concentration for the Mean Drop Size during Emulsification in Turbulent Flow;" Langmuir 2004, 20, 7444-7458.
Adiga, K.C.; "Droplet Breakup Energies and Formation of Ultrafine Mist": NanoMist Systems, LLC; The Navy Technology Center for Safety and Survivability; Chemistry Division; Naval Research Laboratory; Washing D.C.; 14 pages, (Year:2006).
Seidel Jr., George; "Modifying oocytes and embryos to improve their cryopreservation;" Theriogenology 65 (2006) 228-235; Animal Reproduction and Biotechnology Laboratory, Colorado State University.
Smith, Lloyd M et al; "Stability of Milk Fat Emulsions. I. Preparation of Model Oil-in-Water Emulsions and Evaluation of Their Stability;" Department of Food Science and Technology; University of California, Davis; Journal of Dairy Science; vol. 58 No. 9; 1249-1252, (1975).

* cited by examiner

SYSTEM AND SUBSTANCES FOR CRYOPRESERVATION OF VIABLE CELLS

This application is the U.S. National Stage of International Application No. PCT/US2013/030222, filed Mar. 11, 2013, which claims the benefit of and priority to U.S. Provisional Application No. 61/685,224 filed Mar. 14, 2012, each application hereby incorporated by reference herein in its entirety.

I. TECHNICAL FIELD

The present invention relates to the field of cryopreservation of biological substances such as cells, tissue, and the like. In particular it relates to processes, substances, and apparatus that can enhance and achieve cryopreservation and the freezing of biological substances, tissues, and cells in a manner that achieves enhanced results for the substances themselves, such as enhancing the viability of the frozen biological substances or perhaps enhancing the cryopreservation process itself to allow inclusion of additional substances, speed the process, or otherwise afford technical or economic advantages.

II. BACKGROUND

The need and desire to maintain the functionality of cells and/or cellular collections has been known for a long period of time. Preservation has been approached by a variety of methods including desiccation, and freezing. Freezing or cryopreservation is now a common method to preserve cells. Cellular collections are cooled then frozen to a final temperature perhaps such as −80° C. or −196° C. in liquid nitrogen. Of course freezing by definition is an exothermic reaction (reducing heat energy) and is explained by a phase change from a liquid to a solid by removing energy. Cryopreservation can include the use of very low temperatures to preserve structurally intact living cells. However while they may be structurally intact, the same cells are often not viable upon thawing. In fact, cryopreservation is wrought with challenges in that thawed cells are often damaged in some sense. For example frozen neurons have a post-cryogenic viability rate of about 30%. Live births from frozen oocytes can average about 20%. Nearly 50% of cryopreserved sperm cells are often not viable after cryopreservation. Similarly in cells such as umbilical cord blood, depending on the technique used, only 40% or less of the cells may be viable.

Often four primary factors can affect cryopreservation success. These may include cryopreservation media, temperature, freezing profiles and viability assessment. Moreover, post cryogenic viability can even be affected by handling after thawing. Common methods to allay some of the cryopreservation damage include addition of cryoprotectants such as glycerol which may increase the viscosity of the solution and vitrification. Large molecules are known to have a positive effect of increasing viscosity and therefore serve to protect cells. A variety of cryoprotective agents are known to those skilled in the art as explained below. Further, rapid cooling or rapid removal of thermal energy, can promote vitrification. Generally it is understood that vitrification can positively affect the viability of the cells. Although desired rates of cooling can vary by cell or tissue type, removing energy from the system at a rate of about −1 to −3° C./min can be considered a general rule of thumb. Controlling the rate of freezing by removing the energy out of the system at a predictable, repeatable rate appears to reduce some of the damage caused by freezing and thawing. Some substances in the cryopreservation fluid may affect the rate of freezing and of thawing. Of course, viability is affected by both by the removal of thermal energy then later by the endothermic reaction, or addition of energy to return the cell to its normal metabolic status. Adding energy to the system, for example exposing a cryovial to room temperature air, can cause a 25 degree temperature increase (−75 to −50° C.) in one minute. Such an increase in energy can be beneficial during thawing of cells as a rapid 60-90 second temperature increase to around 37° C. may decrease damage related to thawing. Cryopreservation fluid can also be customized to the type of cellular collection involved.

A component of significant influence on cryopreservation success can be the measure of viability. Of course, viability depends on the type of cellular collection and the parameter (s) to be measured. Cryopreservation induced damage that may affect viability might include induction of apoptosis or apoptotic cascade, necrosis, damage to external membrane proteins, DNA damage, oxidative damage, membrane damage, disruption in the functional areas of the cell or tissue as well as impaired growth capacity. In addition cells may experience biochemical toxicity. The effects of toxicity can include cytoskeletal reorganization, suppression of normal metabolism and membrane composition shifts. Upon thawing, if the cell has survived the effects of the toxicity, often the biochemical markers are modified such that the cell is no longer functional. Measuring these functionalities can provide a measure of the viability of the cell after cryopreservation.

The apparent limitations of cryopreservation and less than optimum anticipated results are even to some degree accepted by current technology. Several patents speak to methods of limiting cryopreservation damage by rendering the cells immotile (U.S. Pat. Nos. 7,892,725 and 7,838,210), protecting cells by using a cold shock method (U.S. Pat. No. 7,820,425), microcapsulation of embryos or cells in an alginate or similar material prior to vitrification and inclusion of an ice nucleator (US2010/0311036).

It has been postulated that antioxidants and protective components may be beneficial to cells as they go through cryopreservation, long term storage, thawing and secondary use. Interestingly it may be more economical to store cells at −80° C. than in liquid nitrogen but metabolic activity is not completely inhibited at −80° C. and therefore post cryogenic viability can be affected not only by inherent cryopreservation issues but also metabolic byproducts. These same metabolites can be problematic when cells are thawed then held in their cryopreservation fluid. Such activities can increase the potential value of compounds such as vitamin E, linoleic acid, triterpenes, phenylpropanoid, alkaloids and other hydrophobic or water insoluble structures. However, the use of hydrophobic moieties such as tocopherol and the like has been less satisfactory, and not generally addressed except in a limited sense. Examples of such include, but are not limited to, addition of tocopherol (vitamin E) to sperm cells wherein data has shown it to be beneficial in one instance, and detrimental in the next. Moreover the addition of other hydrophobic moieties such as lipids to cell culture media may be toxic to cultured cells perhaps because of problems with toxicity of free lipids in solution. This toxicity may ultimately affect the viability of the cells.

Cryopreservation is an effective method to store cells, tissues, organs, and genetic materials for the long term. However, concerns about post-cryogenic viability assemblage of biological structures can lessen the applicability and can leave many industries wanting for solutions to aid in the viability of cryopreserved items. The present invention discloses a system which overcomes many challenges associated with cryopreservation, with viability, and with adding certain substances to cryopreservation fluids in a practical fashion. It provides a method to achieve cryopreservation and to add hydrophobic moieties to cryopreservation fluid in a manner that does not reduce, and may improve the post-cryogenic viability of a plurality of biological samples.

III. DISCLOSURE OF INVENTION

Accordingly, the present invention includes a variety of aspects or embodiments which may be selected in different combinations to suit the needs of the user. First, it may be understood that attempts at adding lipids or any hydrophobic moieties, has been fraught with hurdles, including rendering the cells non-viable, and/or failing to confer protective benefits. The ability to remove variability associated with the addition of hydrophobic moieties to cryopreservation media while enhancing post-cryogenic viability is one general goal of this invention. Aspects of the invention may enable a full spectrum of protective benefits to be enhanced or perhaps even conferred upon cryopreserved cellular compositions. It can function with lipid-based antioxidants, membrane stabilizers, and other lipid soluble compounds in such a manner as to benefit not only the cells but also the thermodynamic or other processes of cryopreservation.

The invention can accomplish various goals that can be implemented either alone or in combinations to achieve a variety of objectives. In one general goal, it can function for a large variety of hydrophobic moieties and/or for a large variety of cells, cellular collections, mixtures of cell types, tissues, tissue samples, organs and other samples to be cryopreserved that may benefit such as from the use of hydrophobic substances in the cryopreservation solution.

In another general objective, the present technology can include the counter-intuitive process of adding energy to a cryopreservation solution prior to removing energy to accomplish freezing. Adding energy before removing it has now shown to be beneficial. The invention can even now allow the addition of certain lipids or certain amounts of lipids to cell storage media. Further this objective may help to prevent some damage to cells imparted by thermal energy removal during the standard cryopreservation process.

Generally embodiments of the process can permit the use of new and novel oils, new hydrophobic moieties, new lipids, or multiple lipids, that can beneficial substances in a cryopreservation fluid. These may include generally recognized as safe (GRAS) ingredients that can be utilized with food substances, and those substances approved for use with cryopreserved tissues and cells to be transplanted into humans. The hydrophobic substances to be added might also include those that could provide beneficial effects to the subject in which the cryopreserved cellular compositions are transferred or utilized.

The present invention may also enable addition of lipids not previously suitable for use with cellular collections. The present invention may also provide a method to surmount problems with cooling curve and other aspects of traditional cryopreservation processes.

Another broad objective is to enable such additions of surface energy that may in turn permit the freezing process to occur with less damage to viability than occurs during traditional cryopreservation. Moreover such an addition of energy may enable thawing to occur with less damage than during traditional process thawing. The addition of surface energy to the thermal system may be achieved by the multiplication in the number of discrete lipid droplets in the solution without changing the total concentration (v/v or w/v) of the lipid relative to the remaining cryopreservation fluid components.

One more broad objective of the present invention could include addition of energy such that unnaturally small hydrophobic moiety congregations can be realized. Such a composition may be considered as a non-natural fluidic cryopreservation composite. It can be understood that lipids and other hydrophobic moieties do not exist in a small independent droplets state unless confined by a membrane or other such barrier and therefore this state can be considered unnatural for lipids and other hydrophobic moieties. In the present invention, these unnaturally small congregations of lipids may also exist in a skewed size distribution that favors smaller size droplets like a positively skewed distribution, and which may not represent a normal Gaussian distribution of droplet size. The distribution of the unnaturally small droplet size may be such that the distribution is strongly unimodal; that is, strongly favoring a mode of one droplet size. This type of distribution of lipid droplet size may also create a situation where repeatability of cryopreservation is improved thereby providing a more reliable, non-variable cryopreservation process. Modification of the droplet variation, and associated limitation of droplet size may occur after or as a result of the addition of surface energy to the cryopreservation media (perhaps in situ) thereby maintaining the prescribed concentration of hydrophobic moiety while also enabling the addition without negative effect on the thermal profile necessitated by the particular cellular collection. Removal of, or limitation of, droplets of a specific size profile outside of the cryopreservation fluid may make it difficult to maintain or measure the appropriate lipid composition and/or concentration therefore in situ sizing may provide improvements over current technologies.

Another general objective of the present invention may also provide a more homogeneous crystallization process than expected with the addition of substances outside the standard cryopreservation media substance list.

In embodiments, the goals of the invention may be achieved by structurally or physically altering the hydrophobic substances in the cryopreservation fluid in such a manner as to add surface energy to cryopreservation media before addition of cellular collections and before thermal energy removal. The drop transformation of lipids may enable addition of surface energy to the cryopreservation media in such a manner as to provide, enact and/or enable beneficial thermal energy removal during freezing. Surprisingly, the addition of energy and improved thermal energy removal may improve post-cryogenic viability of cells. For substances that form drops (through surface tension or such) there is a physical relationship between the amount of surface energy of the substance and droplet size. By increasing the number of droplets in the cryopreservation media prior to adding a cellular collection, the surface energy, perhaps measured as joules per kilogram can be increased. Of course, depending on the hydrophobic moiety to be added and the surface tension of such larger congregations, the surface energy added to the system may vary. Such variation could be between lipid compositions not within the fluidic cryopreservation composites made with the same lipid and lipid concentration assuming all other variables remain static. Surprisingly, an increase in surface energy may, among other aspects, even enable a more uniform decrease in thermal energy perhaps thereby providing an effective cryopreservation process which may also be more non-variable due to such controlled energy addition. Further, included in a broad objective it is understood that hydrophobic moieties including lipids, by their nature are immiscible in water, or water-based solutions such as cryopreservation media. The tendency of lipids in a solution is to coalesce into large droplets as such coalescence may increase the kinetic stability. Rending large droplets into smaller droplets is an unnatural state for the hydrophobic moieties and usually does not occur naturally. Small lipid droplets may generally be unstable and may coalesce perhaps quickly. In the present invention however creating unnaturally small droplets may increase the overall, general stability of the cellular system. In addition, perhaps creating substantially uniform maximum droplet size of a hydrophobic substance will provide enhanced stability both prior to, during and post-cryopreservation. In this invention the increased stability imparted by unnaturally small droplets may also affect or perhaps even enhance the shelf life stability of cryopreservation fluid.

These hydrophobic substances, rended as described, may also then be more bioavailable for cellular collection utilization. This may provide additional benefits to the post-cryogenic viability of said collection.

Another broad objective of the invention may enable the use of most water-insoluble organic molecules which may fall into such broad general classes as fats, phospholipids, waxes, sterols and steroids which may be of plant or animal origin. The addition of such a broad class of substances may enable significant improvements in cryopreservation. It should be understood that the present invention may include modifications which make allowances for the different physical properties of the different classes of lipids and lipid-products.

IV. BRIEF DESCRIPTION OF DRAWINGS

V. MODE(S) FOR CARRYING OUT THE INVENTION

Figure 1:
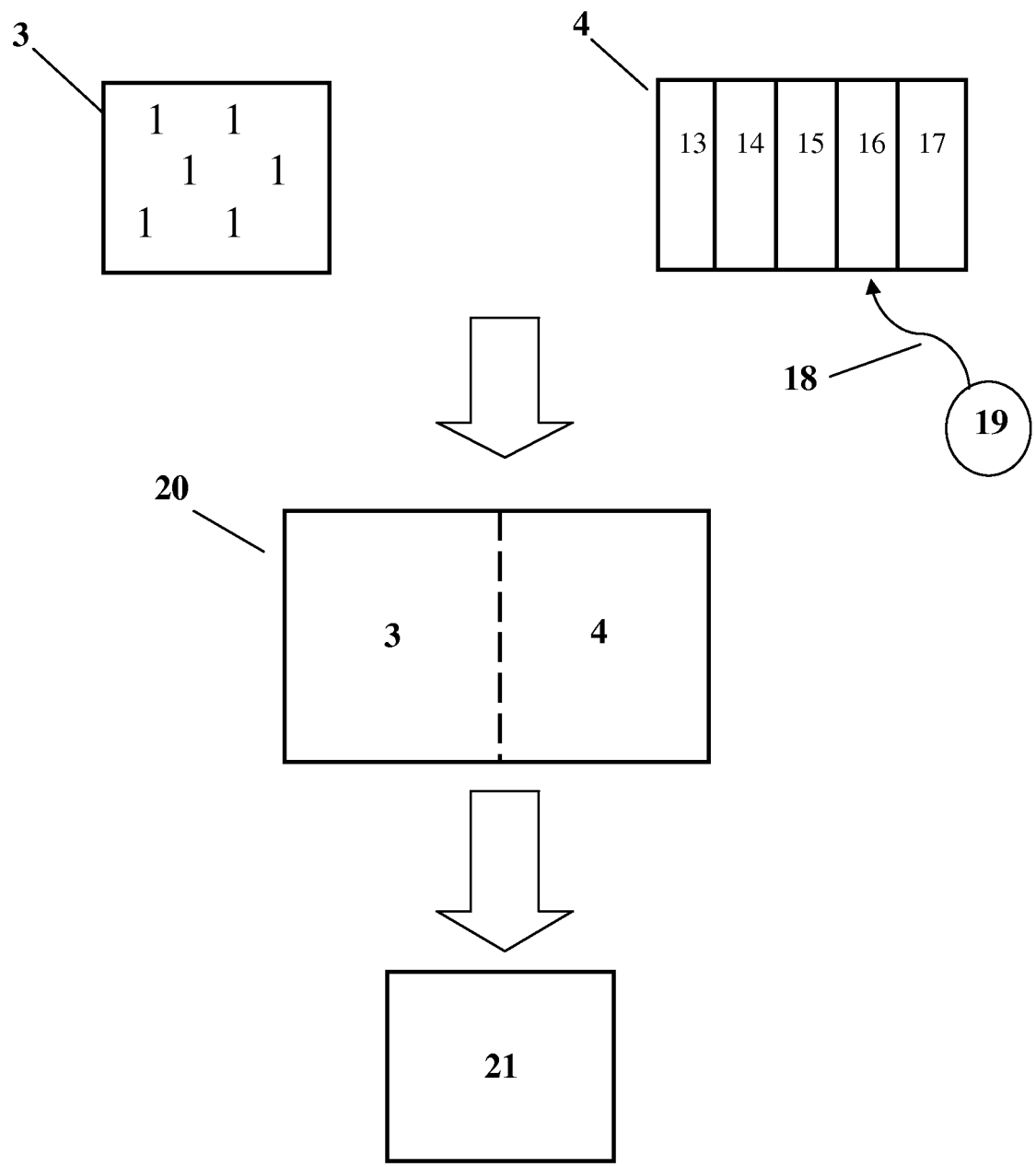
FIG. 1 represents a schematic of equipment and substances as they may be used in embodiments of the present invention.
Figure 2:
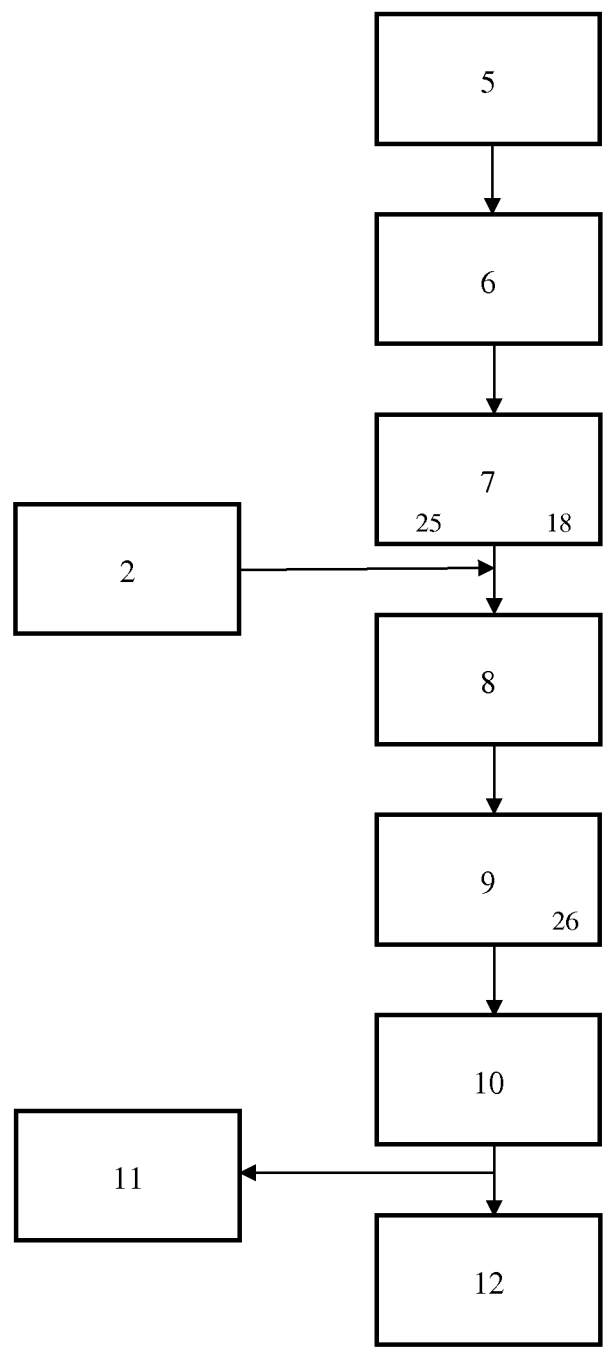
FIG. 2 represents one process flow as may exist in accomplishing processes according to embodiments of the present invention.
Figure 3:
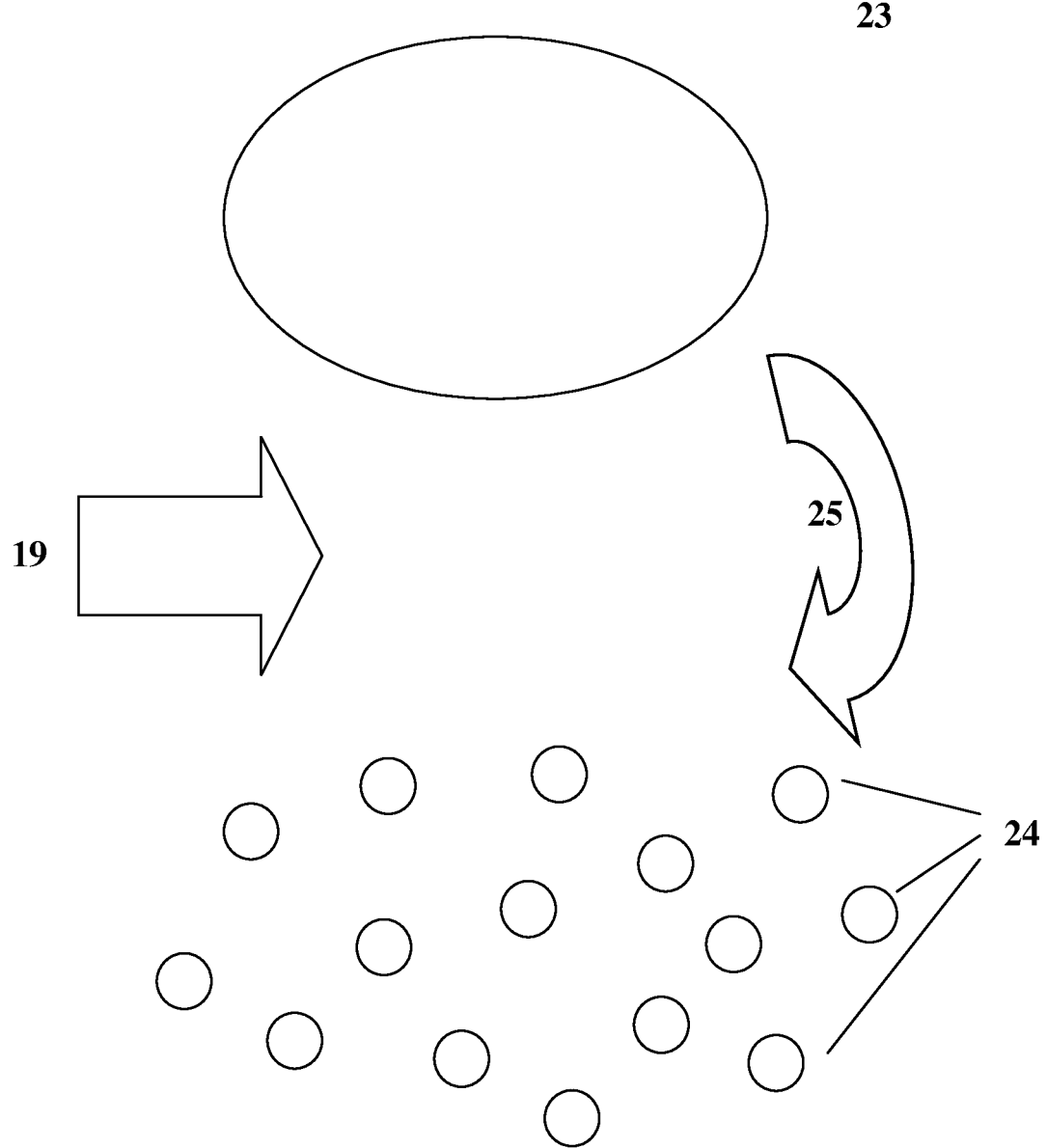
FIG. 3 represents a schematic depiction of before and after example of a conceptual substance that has been rended according to embodiments of the present invention.
Figure 4:
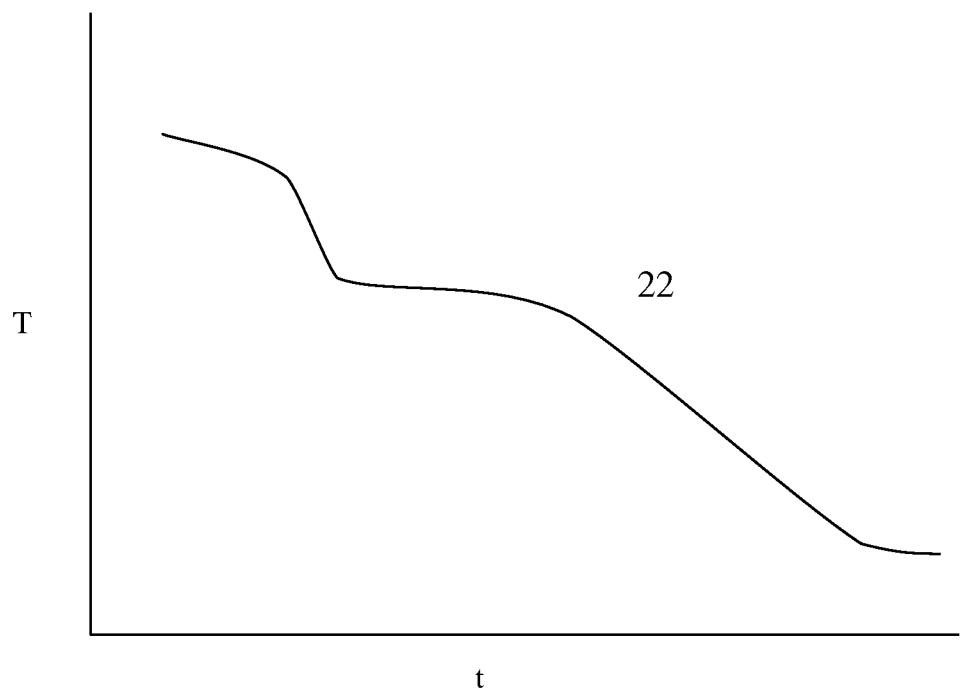
FIG. 4 represents a general cooling curve such as might be used in the cryopreservation process according to an embodiment of the present invention.
Figure 5:
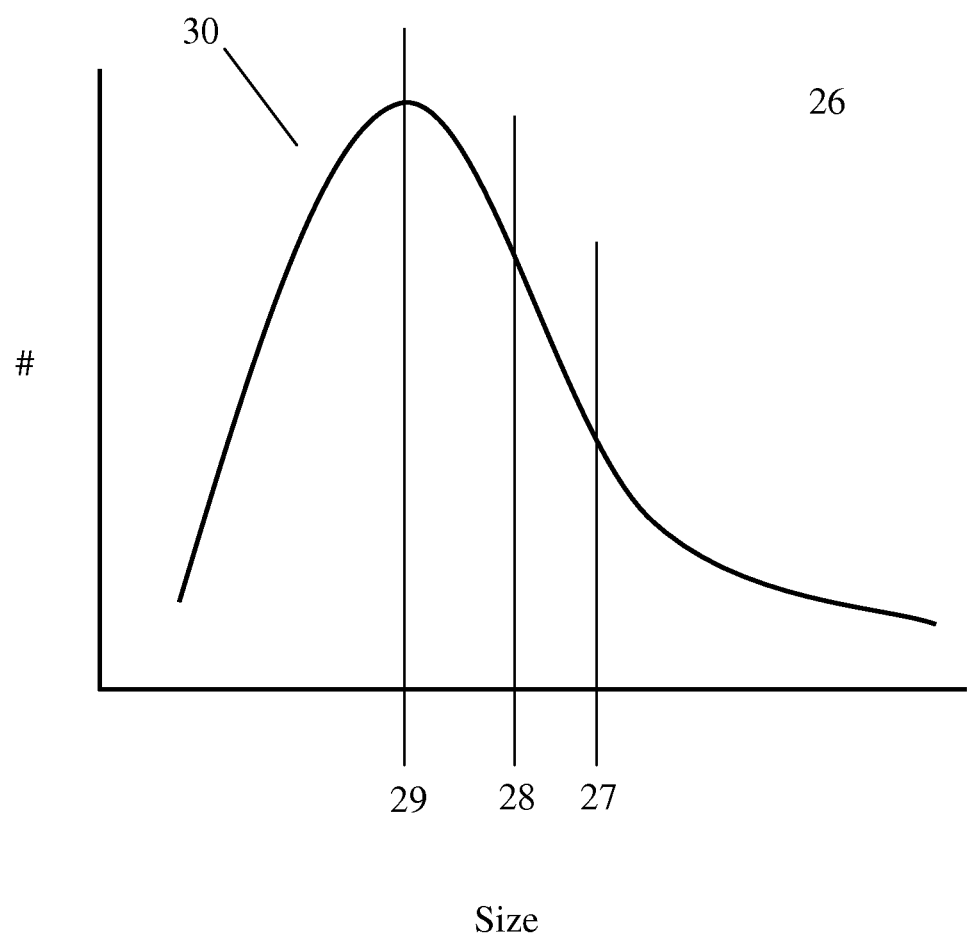
FIG. 5 represents size distribution depiction showing how distributions can be altered in an embodiment of the present invention.

The basic concepts of the present invention may be embodied in a variety of ways. It involves treatment techniques and methods, compositions and combinations of naturally derived and synthetic hydrophobic moieties, as well as equipment to accomplish the appropriate treatment. In this application, the treatment techniques and equipment are disclosed as part of the results shown to be achieved by the various devices described and as steps which are inherent to utilization. In addition, while some devices are disclosed, it would be understood that these not only accomplish certain methods but also can be varied in a number of ways. Importantly, as to all of the foregoing, all of these facts should be understood to be encompassed by this disclosure.

Cryopreservation can involve assembling (2) a subject cellular collection (1) to create an assemblage (3) of cells, tissue, seeds, or the like. In addition, a cryopreservation fluid (4) can be collected (5). Substances of this cryopreservation fluid (4) can be combined (6) to create the typical composite cryopreservation fluid (4). According to embodiments of the present invention, the cryopreservation fluid (4) may be conditioned or treated (7) to enhance the process. The subject cellular collection (1) can be mixed (8) with some type of cryopreservation fluid (4) to form a cryopreservation composite (20) and then have thermal energy removed (9) from it to accomplish freezing (26) to form a frozen cryopreservate (21). To use the cells or the like, thermal energy can be added (10) to effect thawing. The thawed composite can have items separated (11) for ultimate use (12) hopefully presenting viable, functional cells.

As mentioned earlier, the cryopreservation fluid (4) can have various elements (13)-(17). One element can be a cryoprotectant or cryoprotective agent (13). A variety of cryoprotective agents are known to those skilled in the art. These can include the following: acetamide, agaroses, alginates, alanine albumin, ammonium acetate, butanediol, chondroitin sulfate, chloroform, choline, cyclohexanediols, dextrnas, diethylene glycol, dimethyl acetamide, dimethyl formamide, dimethyl sulfoxide*, erythritol, lethanol, ethylene glycol, monomethyl ether, formamide, glucose, glycerol, glycerophosphate, glycerylmonoacetate, glycine, hydroxyethyl starch, inositol, lactose, magnesium chloride, magnesium sulfate, maltose, mannitol, mannose, methanol, methoxypropanediol, methyl acetamide, methyl formamide, methyl ureas, methyl glucose, methyl glycerol, phenol, pluronicpolyos, olyethylene glycol, polyvinylpyrrolidone, proline, propanediol, propylene glycol, pyridine N-oxide, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and xylose. Of course, each agent or the overall cryopreservation fluid (4) can be customized for the application or cellular collection (1) or individual cells involved.

The overall cryopreservation fluid (4) may also commonly contain a foundation medium (14) perhaps such as water, an energy source (15), and the cryoprotectant (13). Other ingredients (16) and (17) can be included as well and as one skilled in the art would well understand these can vary by cell type or process. For example, media may be 90% serum+10% cryoprotectant (glycerol or DMSO, dimethylsulfoxide). In general, cryoprotectant concentrations may range from 2 to 10% or 20%. Serum may include HEPES (4-(2-hydroxyethyl)-1-piperazineethanesulfonic acid), sodium bicarbonate, fetal bovine serum, bovine serum albumin, fetal serum albumin and the like. Another general media for suspension cell types can include 45% fresh medium used to grow the cells plus protein, 45% used (depleted) medium plus 10% cryopreservative. Cryopreservative concentrations may vary but, as mentioned, often range from 2-10% such as for DMSO or the like, and 2-20% for glycerol and the like, again dependent on cell type as some cryopreservatives are cytotoxic for some cells. For example, sperm freezing medium may contain serum albumin, glycerol and sucrose and may contain egg yolk or milk (20%) plus 6% to 10% glycerol (final concentration). The solution may include HEPES, sodium bicarbonate, fetal bovine serum, bovine serum albumin, fetal serum albumin and the like. Another commercial freezing medium may contain high-glucose Dulbecco's modified eagle medium (DMEM) or Earle's balanced salt solution, Hank's balanced salt solution, nutrient mixture F-12 (Ham's), Leibovitz's L-15 plus 10% serum (such as fetal bovine serum), 10% DMSO. Such solutions may also include D-glucose, L-glutamine, sodium pyruvate, phosphate buffered saline, calcium and magnesium salts. For embryos equilibration and vitrification media may include: 7.5% DMSO, 7.5% ethylene glycol, 20% DSS, 0.5M sucrose in HEPES buffered medium. For sperm cells equilibration and freezing media may include: Sodium citrate, 20% egg yolk, or 4% milk fat, fructose and/or 7% glycerol.

The principal components of lipid modified cryopreservation can be cryopreservation media customized for a specific cell, tissue, organ and/or cellular composition, the biological cellular composition, a hydrophobic extract that is not generally miscible with the water-based cryopreservation media, a method to condition or treat (7) the cryopreservation fluid (4), such method may include adding (18) energy (19) such as through surface energy, to the cryopreservation fluid (4), a method to decrease or reduce thermal energy (9) from the cryopreservation media, and a method to assess post-cryogenic viability of the cryopreserved structures. Lipids not previously considered adequately suitable for use can now be used. From one perspective, the reasons they may have been unsuitable include the inadvertent and/or unintended modification of the optimum cooling curve (22) for a specific cell type. In an embodiment of this invention the addition of energy (19) may work with a variety of commercial cooling devices and commercial freezing devices and techniques without requiring undue modification.

In another embodiment of the invention the addition of hydrophobic substances can be achieved via the addition of energy (19) to a cryopreservation fluid (4) or media. This energy input may be achieved using one or a combination of commercially available pieces of equipment designed to rend large items into smaller items. These pieces of equipment are well known to those skilled in the art.

In one embodiment of the invention the surface area of hydrophobic moieties is increased by rending (25) large drops (23) to create sufficient surface energy within the lipid containing cryopreservation fluid so as to provide enhanced post-cryogenic viability of the cryopreserved cellular collection. Rending (25) the lipids or hydrophobic moieties may include increasing the number of initial large drops (23) to droplets (24) increased in number by a multiple of perhaps 50 times or many more times. Rending (25) should be understood to be dependent on the particular hydrophobic solution and specific surface tension for said solution. Rending (25) may be achieved by a variety of methods including physically dispersing large droplets, shearing, cavitation, sonication, pressing, chemical means, relatively energetic mechanical mixing, using a detergent, salts, common emulsifying or similar methods and many other commercially available methods. The present invention is independent of the method utilized to rend and may instead focus on the apparent surface energy imparted by said rending. In one embodiment the number of droplets may be specific to a particular lipid and lipid surface tension and the same number of droplets may represent different additions of energy to the substance in the cryopreservation fluid.

In still another embodiment, the effect and a measurement of the viability can be specific for a specific cell type and in general can be understood to include at least one of a variety of attributes including reducing the amount of apoptosis, reducing the quantity of necrotic cells, decreasing damage to external membrane proteins, decreasing DNA damage, decreasing oxidative damage, decreasing membrane damage, decreasing the amount of disruption to functional areas of the cellular collection, limiting biochemical toxicity, suppressing cytoskeletal reorganization and membrane composition rearrangement. Viability improvement can be compared to traditional post-cryogenic cells of a similar character and thermal treatment. Methods of assessing viability may be known to vary also so viability assessment could optimally utilize the same methods, techniques and protocols to assess viability.

In another embodiment of the invention the addition of lipids may not cause a negative change in the kinetics of the thermal energy decrease that is necessary for said cellular collection to experience cryopreservation down to the target temperature of either about −80° C. or about −196° C. Likewise in another embodiment of the invention lipids may have a droplet size that enables appropriate rate of thermal energy input of said cellular collections to be thawed. Such enablements should be understood to not diminish or positively affect the post-cryogenic viability of the cellular collection.

In still another embodiment the addition of the lipid may comprise an antioxidant that protects said cells from oxidative damage during processing pre- and post-cryopreservation. Moreover, the lipids or hydrophobic moieties might comprise or may be selected such that they serve as antioxidants or a free-radical scavenger for the specific stresses experienced by a specific cellular composition type. Lipids might also comprise or contain membrane stabilizers such as cholesterol, lipid cryoprotectants, and other types of lipids as may be beneficial to the particular cellular composition or the particular cryopreservation media.

In still another embodiment the lipids may be derived from any number of sources including animal fats, lipids from reproductive structures such as egg or seeds, lipids from animal byproducts such as milk and other bodily fluids, plants, fruit, roots, leaves, seeds, whole plants, fruits, fruit pulp, cotyledons of plant embryo, endosperm, seeds, leaves, nuts, milk, roots, bark, algal and fungal derived lipids, and other plant parts, milk, algae, fungus, yeast cells, synthetic lipids, mixed oils and the like, and may include multiple lipid sources within one cryopreservation fluids to achieve the goals of protecting the cryopreserved cell. Lipids may also be synthetically created or be bio-identical in order to emulate naturally produced lipids or the functionality of lipids such as synthetic vitamin E versus naturally extracted vitamin E. Lipids may be any substance which can be extracted using such compounds as ether, benzene, or other nonpolar solvents. Lipids for inclusion in the present invention may also be derived using physical means such as centrifugation, pressing and other methods common to those practicing the art. Lipid droplets may be created by a sonifier, a sonicator, a mixer, a blender, a sonolator, a high pressure homogenizer, and even a microsieve emulsifier.

In one more embodiment the extracts may include lipids from the following gross classes of lipids: triacylglycerols, polyphenolics, tocopherol, ascorbic acid, poly-unsaturated fatty acids, saturated fatty acids, anthraquinones, phospholipids, sterols, sterol esters, carotenoids, liquid waxes and glycerolipids perhaps more specifically including the following: monagalactosydiacylglycerol, digalastosyldiacylglycerol, sulfoquinovosyldiacyllglycerol, triacylglycerol, phosphatidylcholine, phosphatidylethanolamine, phosphatidylinositol, phosphatidylglycerol, glycosyldiacylglycerols and others. Fatty acids may include 16:0, 18:0, 18:1, 18:2, 18:3, plus $C_{20}$-$C_{22}$ but may also include any of the other known or unknown saturated and/or unsaturated fatty acids.

In one more embodiment additional substances such as weighting agents and emulsifiers may be added to the blend of lipids to further enable a uniform population of lipid droplets and to further enable emulsion stability. Similarly the lipid droplet size may be such that it is unnaturally small. It may also be selected so it is not unstable and thus not requiring additional substances. In a similar embodiment, the emulsion may be stabilized by solid particles such as colloidal silica, latex particles or proteins such as casein (milk fat proteins) such that a pickering emulsion is formed and droplet stability is further enhanced.

In another embodiment the emulsion may be classified as an emulsifier stabilized and/or nanoemulsion indicating the small droplet size. The size distribution (26) of the numbers of droplets (24) can vary in different ways. The size value selected, desired, or resulting can present a maximum so that no substantial numbers of drops or droplets exist with significantly larger sizes, so that particular maximum percentages of droplets with larger sizes (by number or even by volume) is established. It can also represent an average, mean (27), median (28), or just a non-normal distribution as well. In one embodiment, the unnaturally small or other droplets of the lipid or other substance may also exist in a skewed size distribution (30) such as may favor smaller size droplets (24), perhaps as in a positively skewed distribution (30), as opposed to a normal Gaussian distribution of droplet size. The distribution may also be strongly unimodal, strongly favoring a mode (29) of one droplet size, perhaps a reduced mode droplet size. These, of course, can have specified values as explained below.

In one embodiment the invention may provide a method for input or use of at least one lipid into a cryopreservation fluid. Such embodiments may include methods to size, size exclude, and size limit droplets of said lipid in the cryopreservation media. These may be utilized to achieve an unnaturally small droplet size and/or distribution that provides the appropriate surface energy to the cryopreservation fluid.

In some embodiments, the method may include techniques for utilizing multiple hydrophobic substances from disparate sources including plants, animals and synthetic sources and which may easily be exemplified by egg yolk, milk lipids and soybean oil. The method may also include use of substances from multiple sources such as egg yolk and plant derived olive oil. In the next embodiment lipids may serve as an antioxidant or radical-scavenger for said cells. In another embodiment said lipids may be selected such that they may serve as a membrane stabilizer for the specific cell type being frozen. In another embodiment the combination of lipids may be selected such that they serve as both antioxidant or radical-scavenger and/or membrane protectant for the specific cell type being frozen.

In an embodiment of the invention a variety of lipids could be added to a variety of cellular compositions including, but not limited to, skin, oocytes, sperm, stem cells, embryonic stem cells, neural stem cells, epithelial stem cells, cardiac stem cells, muscle stem cells, connective stem cells, epithelial cells, cardiac cells, muscle cells, connective cells, nerve cells, umbilical cord blood, blood, histological samples, plant seeds, plant shoots, ovarian tissue, testicular tissue, embryos, tumorous tissue, yeast cells, bacterial cells, algal cells, fungal cells, mesenchymal cells, keratinocytes, melanocytes, hepatocytes, liver tissue, and the like.

Embodiments of the present invention may provide a kit for creating a stable emulsion meeting the parameters including such commercially available items such as glassware which promotes simultaneous mixing and cooling of the liquids, a method and/or equipment to disrupt the lipids to create an oil-in-water emulsion with a predictable size distribution, mean, media, and mode, a method to filter or restrict the droplet size to an acceptable range post production, a method and/or equipment to determine the resulting average lipid droplet size and range of droplet sizes, and even a method to further modify or filter the lipids if it does not meet the said criteria. A kit may also include the appropriate lipid blends, emulsifier(s), weighting agent(s), filtering methods, methods to store stabilized emulsion prior to use, cooling methodology or equipment, freezing methodology or equipment, and even thawing methodology or equipment.

An example of the benefits of embodiments of the present invention can be shown by a comparison of processes for an application to sperm cells as follows. Initially as a control, one can create a solution of Tris extender for 1000 mls (pH 6.8, osmotic pressure 322-325 mmol/kg) perhaps with the following components: 10.53 g Tris, 4.38 g fructose, 5.53 g citric acid, and 870 ml $H_2O$. To 500 mls Tris, one can add 22% egg yolk (all white removed; Part A extender) and mix by hand or using a stir bar. One can dilute concentrated ejaculate using Part A extender so sperm cells reach a final concentration of $15 \times 10^6$ cells/ml. This mixture can be cooled to about 4° C. then one may add a part B extender (Part A plus 14% glycerol) to a final concentration of 7% glycerol to cooled sperm cells. This can be allowed to equilibrate and then packaged as the cooled suspension is put into straws. These straws may be cooled over liquid nitrogen vapor at a rate of about 10-20° C./min then the straws may be plunged into the liquid nitrogen. This may be stored at the −196° C. temperature of liquid nitrogen until needed. To utilize these straws, they may be removed from the liquid nitrogen and submerged in a 37° C. water bath for about 60 seconds.

As an improvement that modifies the cryopreservation fluid (4), lipids can be added to the part A extender of the above example prior to addition of the cells. This addition may be of the 22% egg yolk with added 5% mineral oil. Energy can be added (18) wherein these lipids may then be sonicated at 30% for 2 times before using the solution to dilute the sperm cells. Other options for energy addition (18) can include mechanical mixing, physical dispersal and the like. The energy addition can rend (25) the lipid as explained.

As can be seen from the following data (Table 1, experiment 1), clearly the addition of lipids without modifying (7) to the cryopreserved cells negatively affected the viability of the cells. In this example total lipid content is 20% egg yolk plus the varying percentage of hydrophilic (lipid) extracts results in a total lipid concentration of up to 29% total lipid (v/v). This additional lipid causes a statistically significant 70% decrease in viability. With modifying (7) the addition of ≥270 j/kg or ≥330 j/kg (ex. 2 and 3) as energy additions (18) to the lipid containing cryopreservation fluid (4), the viability is equal to, or superior to 20% total lipid example. As can be seen by example 2, the type of lipid also has an effect on energy required to achieve superior viability. For example, oil A may benefit from higher energy addition. Note, the post-cryogenic viability difference from traditional post-cryogenic cells (0% extra lipid) is >29 percentage points in example 1, while in example 2, where energy is added, the difference is <5 percentage points, a significant improvement in post-cryogenic cell viability. Comparing the viability of cells with 20% total lipids in example 3, one sees an improvement in viability by adding >270 j/kg energy and increasing the total percentage of lipid is beneficial. Note, this table only reflects one measure of viability for these cells but does not reflect benefits such as a 30% increase in DNA quality when using 9% oil B as compared to traditional post-cryogenic cells of a similar character and thermal treatment.

TABLE 1

| Oil | A | B | C | A | B | C | A | B | C |
|---|---|---|---|---|---|---|---|---|---|
| Additional hydrophobic extracts (percent v/v) | | 0 | | | 3 | | | 9 | |
| Total lipid concentration (percent v/v) | | 20* | | | 23 | | | 29 | |
| EXAMPLE 1 Post-cryogenic viability (Motility) | | 41 | 30 | 30 | | 12 | 18 | | |
| EXAMPLE 2 Post-cryogenic viability (motility) with addition of ≥270 j/kg energy** | | 26 | 28 | 32 | 21 | 20 | 26 | | 26 |
| Post-cryogenic viability (motility) with addition of ≥330 j/kg energy** | | 26 | 27 | 29 | 27 | 19 | 27 | | 26 |
| EXAMPLE 3 Post-cryogenic viability (motility) with addition of ≥270 j/kg energy | 57 | 59# | | 57 | 60 | 57 | 38 | 57 | 55 |

*contains only egg yolk lipids, no additional lipids.
**No energy addition to the sample with 20% total lipid concentration.
Energy addition to sample with 20% total lipid concentration Semen from 10 production bulls (example 1, 7 production bulls (example 2) or 5 production bulls (example 3) was collected and initially evaluated using industry standard procedure. Ejaculates were extended to $56 \times 10^6$ sperm/ml in egg yolk citrate extender (part A) containing 20% egg yolk plus oil extract A, B or C at 0, 2, 6, 10, 14 or 18% and held for a minimum of 2 hours at 4° C. After equilibration at 4° C., an equal amount of part B extender (egg yolk citrate+ 14% glycerol) was then added, the sperm packaged in 0.5 cc straws at a final concentration of $28 \times 10^6$ sperm/ml resulting in a final concentration of 0, 1, 3, 5, 9 or 9% oil A, B or C. Oil A=Olive oil, Oil B=Sea buckthorn, Oil C=Mineral oil. The sperm was frozen over nitrogen vapor then plunged into liquid nitrogen using industry standard procedure.

These sperm cells were thawed by immersing in a 37° C. water bath for a minimum of 45 seconds. Three replicates of each treatment/bull were analyzed after thawing and warming for 30 minutes for motility. Motility parameters including total and progressive motility, velocity parameters were assessed by Hamilton-Thorne IVOS system with the following standard settings: Progressive cells: path velocity (VAP) 500 μm/s, straightness 70%; image capture: frames per sec 60 Hz, 40 frames. Slow cells-static: VAP cutoff 30 μm/s, ASL cutoff 15 μm/s. Cell size 5 px, cell intensity 70. 2x-CEL slides (Hamilton-throne) were used for all evaluations.

Motility above is the average of 10 bulls per treatment (ex. 1) or 7 bulls per treatment (ex. 2), 5 bulls per treatment (ex. 3) in extenders where the addition of 270 j/kg energy (ex. 1, 2 and 3) or ≥330 j/kg energy (ex. 2) was added to the extender prior to the addition of sperm cells.

As can be understood from the above examples, the modifying of the cryopreservation fluid (4) and particularly the addition of surface energy to the fluid prior to the removal of thermal energy has a very beneficial effect. While the above examples indicate some values and substances used, naturally, these can be varied to achieve the desired result in any application. For example, the variations can be accomplished to achieve set values or thresholds of cell viability improvement. Of course, embodiments can achieve as much improvement as possible, but levels of improvement in viability can provide or present a substance with at least about 5%, 10%, 15%, 20%, or even 25% higher post-cryogenic viability for the biological cell structures or the like as compared to or over traditional post-cryogenic cell structures of a similar character and thermal treatment. Similarly, embodiments can provide or present a substance with not less than about 80%, 70%, 60%, 50%, 40%, 30%, and 20% of the pre-cryogenic viability, however measured, for the biological cell structures or the like.

Another aspect that can be varied in embodiments of the invention can be the amount of energy or even surface energy added. This can be varied so that the values achieved can result in adding at least about, or result in a cryopreservation fluid (4) containing a substance having its surface energy increased by at least about 100 j/kg, 270 j/kg, 320 j/kg, 650 j/kg, 1050 j/kg, 3600 j/kg, or even 5200 j/kg. This can even be mainly the lipid in the cryopreservation fluid (4). Similarly, the surface energy of a substance in the cryopreservation fluid (4) can be increased to at least about 200 j/kg, 420 j/kg, 760 j/kg, 1200 j/kg, 3800 j/kg, or even 5400 j/kg of surface energy. From another perspective, the surface energy of a substance in the cryopreservation fluid (4) can be increased by at least about 30%, 50%, 100%, 3 times, 5 times, 10 times, 30 times, or even 50 times that of the preexisting state.

Yet another aspect that can be varied in embodiments of the invention can be the transformation in the number of drops or droplets present. This can be varied so that the values achieved can result in causing droplets that number, or presenting a substance having droplets numbering at least about 30 times, 50 times, 100 times, 500 times, 1000 times, 5000 times, 10000 times, 50000 times, and even 100000 times the number of initial drops of the substance in the cryopreservation fluid (4) or of an typical fluid of such character.

Still another aspect that can be varied in embodiments of the invention can be the size of the droplets resulting. This can be varied so that the values achieved can present a cryopreservation fluid (4) containing a substance having no substantial number of droplets with a diameter larger than about, or rending larger drops so that there are no substantial amount of droplets larger than about 1000 nm, 900 nm, 700 nm, 500 nm, 300 nm, 100 nm, 70 nm, 50 nm, or even 30 nm in that substance in the cryopreservation fluid (4). Even the distribution of these droplets of the substance in the cryopreservation fluid (4) can be a varied effect. Here, size distributions of the above sizes can be altered so that these sizes or smaller are present for, and droplets as small as exist for at least about 20%, 40%, 60%, 80%, and even 90% of the droplets of the substance in the cryopreservation fluid (4). The activity can cause droplets so that there is no substantial amount of droplets larger than the above sizes perhaps even for only a specified lipid or the like. The distribution can also be just presenting a substantially uniform sizing with or without the above sizes indicated. The distribution can be skewed toward smaller sizes as well. Here even the mode value of size distribution for a substance or even a specified lipid can be less than about the above sizes. Even sizes larger than about the above sizes can be eliminated or even rended so that there are no substantial amount of droplets larger than any of the above sizes. This can occur in situ as well so concentration remains largely unvaried.

Another aspect that can be varied in embodiments of the invention can be the composition of the substances themselves. Even concentrations can be presented that are relatively high concentrations for that substance (as compared to traditional uses and also as compared to unconditioned substances). These concentrations can be at least about 10%, 20%, 40%, 60%, and even 80% higher than traditional lipid concentration cryopreservation fluids as compared to similar fluid of similar character for similar thermal treatment perhaps with similar cells. The substances themselves can now be varied even so that substances can now include lipids, lipid soluble substances, or other substances that may not have previously worked, worked as well, worked at concentrations desired, or been combinable with other substances. Through the present invention processes can now include oils, lipids, hydrophobic substances, or lipids at appropriate concentrations or efficacies, from the following list: sea buckthorn lipids, saturated free fatty acids, unsaturated free fatty acids, lauric acid, myristic acid, palmitic acid, stearic acid, arachadonic acid, palmitoleic acid, oleic acid, linoleic acid, linolenic acid, arachadonic acid, lecithin, triglycerides, spermaceti, bees wax, carnuba wax, sphingomyelins, monoterpenes, sesquiterpenes, diterpenes, sesterterpenes, triterpenes, cholic acid, oleic acid, β-sitosterol, β-amyrin, γ-carotene, α-amyrin, β-carotene, lycopene, lutein, tocopherol, ubiquinol, tocotrienols, eugenol, phosphatidic acid, phosphatidylethanolamine, phosphatidylcholine, phosphatidylserine, phosphatidylinositol, ceramide phosphorylcholine, ceramine phosphorylglycerol, digalactosyldiacylglycerol, monogalactosymonoacylglycerol, 16:1 fatty acids, 18:1 fatty acids, 18:2 fatty acids, 18:3 fatty acids, natural rubber, and gutta-percha.

Through the present invention processes can now include substances combinable with lipids or other substances such as from the following list: thiols, ascorbic acid, polyprenols, superoxide dismutase, catalase, peroxidase, lipoic acid, uric acid, hydrophobic substances (non-lipid), silicones, fluorocarbons, glutathione, melatonin, peroxiredoxins, resveratrol, phytic acid, flavonoids, vitamin A, vitamin E, vitamin D2, vitamin K1, lipid soluable substances, and lipid soluble vitamins.

The above, and other substances can also be used alone or in combination, at different levels, from different forms, plant sources, plant components and enantiomeres such as: plants, plant components, lipids, *Hippophea*, sea buckthorn lipids, seed oil, pulp (fruit) oil, saturated fatty acids, unsaturated fatty acids, lauric acid, natural rubber, leaf alcohol extract, myristic acid, gutta-percha, palmitic acid, *Euterpe oleracea*, açai, fruit, pulp, skin, stearic acid, vitamin A, (perhaps in suspension as well), glycine, soybean, milk, arachadonic acid, vitamin E, lycium, goji/wolfberry, berry, palmitoleic acid, vitamin D2, blueberry, oleic acid, vitamin K1, carya, pecan, nut pulp, linoleic acid, raspberries, fruit pulp, linolenic acid, Rosaceae, strawberry, thiols, *Rubus*, blackberry, triglycerides, ascorbic acid, *Amelanchier* (saskatoon), *Prunus*, plum, spermaceti, polyprenols, litchi, lychee, seeds, bees wax, superoxide dismutase, *Psidium*, guava, leaves, carnuba wax, catalase, sphingomyelins, peroxidase, *Vitis*, grape, monoterpenes, lipoic acid, *Eugenia*, alcohol extract fruit, sesquiterpenes, uric acid, *Olea*, olive, oil and fruit, diterpenes, hydrophobic substances, *Persea*, avocado, *Gymnema inodorum*, australian cowplant, triterpenes, silicones, *Sechium edule*, chayote, cholic acid, fluorocarbons, Mentha, mint, oleic acid, glutathione, *Leucanea leucocephala*, lead tree, shoot tips, β-sitosterol, melatonin, piper, pepper, lecithin, β-amyrin, α-amyrin, peroxiredoxins, eryngium, coriander, carotene, resveratrol, Oenathe, celery, phytic acid, *Zingiber*, ginger, β-carotene, γ-carotene, flavonoids, *Cucrcuma longa*, turmeric, lycopene, lutein, fish, tocopherol, whale, ubiquinol, bee, tocotrienols, fowl eggs, fowl body fat, eugenol, beef body fat, phosphatidic acid, pork body fat, phosphatidylethanolamine, phosphatidylcholine, phosphatidylserine, phosphatidylinositol, ceramide phosphorylcholine, ceramine phosphorylglycerol, digalactosyldiacylglycerol, and monogalactosymonoacylglycerol. While it should be understood that each of these can have varying degrees of effect as a result of the present invention, it is anticipated that advantages for each and for combinations of each exist through the present invention. It is also expected that both particular substances and especially combinations not previously viable are now possible with positive results.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the statements of invention.

Examples of alternative claim may include:

1. A process to enhance the cryopreservation of biological cells comprising the steps of:
   assembling a cellular collection containing a plurality of biological cell structures;
   establishing a lipid containing cryopreservation fluid to be incorporated with said biological cell structures in cryopreservation;
   adding at least about 270 j/kg surface energy to at least one lipid in said lipid containing cryopreservation fluid to create a lipid surface energy increased cryopreservation fluid;
   mixing said lipid surface energy increased cryopreservation fluid and said biological cell structures to form an energy increased fluidic cryopreservation composite;
   removing thermal energy from said fluidic cryopreservation composite;
   freezing said fluidic cryopreservation composite by reducing the temperature of said fluidic cryopreservation composite below the freezing point of water; and
   providing an enhanced post-cryogenic viability for said biological cell structures.

2. A process to enhance the cryopreservation of biological cells as described in clause 1 or any other clause wherein said step of providing an enhanced post-cryogenic viability for said biological cell structures comprises the step of providing at least about 10% higher post-cryogenic viability for said biological cell structures over traditional post-cryogenic cells of a similar character and thermal treatment.

3. A process to enhance the cryopreservation of biological cells as described in clause 2 or any other clause wherein said step of adding at least about 270 j/kg surface energy to at least one lipid in said lipid containing cryopreservation fluid to create a lipid surface energy increased cryopreservation fluid comprises the step of adding at least about 650 j/kg lipid surface energy to at least one lipid in said cryopreservation fluid.
4. A process to enhance the cryopreservation of biological cells as described in clause 2 or any other clause and further comprising the step of drop transforming at least one lipid in said cryopreservation fluid into droplets numbering at least about 50 times the number of initial drops of said lipid in said cryopreservation fluid.
5. A process to enhance the cryopreservation of biological cells as described in clause 2 or 3 or any other clause and further comprising the step of drop transforming at least one lipid in said cryopreservation fluid into droplets numbering at least about 50000 times the number of initial drops of said lipid in said cryopreservation fluid.
6. A process to enhance the cryopreservation of biological cells as described in clause 2 or any other clause wherein said step of adding at least about 270 j/kg surface energy to at least one lipid in said lipid containing cryopreservation fluid to create a lipid surface energy increased cryopreservation fluid comprises the step of rending larger drops of said at least one lipid in said cryopreservation fluid to form smaller droplets of said at least one lipid in said cryopreservation fluid.
7. A process to enhance the cryopreservation of biological cells as described in clause 6 or any other clause wherein said step of rending larger drops of said at least one lipid in said cryopreservation fluid to form smaller droplets of said at least one lipid in said cryopreservation fluid comprises the step of rending larger drops of said at least one lipid in said cryopreservation fluid to contain no substantial number of droplets having a diameter larger than about 1000 nm in said at least one lipid in said cryopreservation fluid.
8. A process to enhance the cryopreservation of biological cells as described in clause 6 or any other clause wherein said step of rending larger drops of said at least one lipid in said cryopreservation fluid to form smaller droplets of said at least one lipid in said cryopreservation fluid comprises the step of rending larger drops of said at least one lipid in said cryopreservation fluid to no substantial number of droplets having a diameter larger than about 200 nm in said at least one lipid in said cryopreservation fluid.
9. A process to enhance the cryopreservation of biological cells as described in clause 2, 4, 7, or 8 or any other clause wherein said step of assembling a cellular collection containing a plurality of biological cell structures comprises a step selected from a group consisting of the steps of:
assembling a cellular collection containing a plurality of blood cell structures,
assembling a cellular collection containing a plurality of stem cell structures,
assembling a cellular collection containing a plurality of skin cells,
assembling a cellular collection containing a plurality of embryonic stem cells,
assembling a cellular collection containing a plurality of neural stem cells,
assembling a cellular collection containing a plurality of epithelial stem cells
assembling a cellular collection containing a plurality of cardiac stem cells
assembling a cellular collection containing a plurality of muscle stem cells
assembling a cellular collection containing a plurality of connective stem cells
assembling a cellular collection containing a plurality of epithelial cells
assembling a cellular collection containing a plurality of cardiac cells
assembling a cellular collection containing a plurality of muscle cells
assembling a cellular collection containing a plurality of connective cells
assembling a cellular collection containing a plurality of nerve cells
assembling a cellular collection containing a plurality of umbilical cord blood cells,
assembling a cellular collection containing a plurality of histological sample cells,
assembling a cellular collection containing a plurality of plant seed cells,
assembling a cellular collection containing a plurality of plant shoot cells,
assembling a cellular collection containing a plurality of ovarian tissue cell structures,
assembling a cellular collection containing a plurality of testicular tissue cell structures,
assembling a cellular collection containing a plurality of embryo cells,
assembling a cellular collection containing a plurality of tumorous tissue cell structures,
assembling a cellular collection containing a plurality of yeast cells,
assembling a cellular collection containing a plurality of bacterial cells,
assembling a cellular collection containing a plurality of algal cells,
assembling a cellular collection containing a plurality of fungal cells,
assembling a cellular collection containing a plurality of mesenchymal cells,
assembling a cellular collection containing a plurality of keratinocyte cells,
assembling a cellular collection containing a plurality of melanocyte cells,
assembling a cellular collection containing a plurality of hepatocyte cells,
assembling a cellular collection containing a plurality of oocyte cells,
assembling a cellular collection containing a plurality of sperm cells, and
10. A cryopreservation composition comprising:
an enhanced cryogenic viability assemblage of biological cell structures; and
an increased lipid surface energy content cryopreservation fluid mixed with said enhanced cryogenic viability assemblage of biological cell structures, containing a lipid that has had its surface energy increased by at least about 270 j/kg surface energy, and that has at some point has been frozen at temperature below the freezing point of water.
11. A cryopreservation composition as described in clause 10 or any other clause wherein said enhanced post-cryogenic viability assemblage of biological cell structures comprises an at least about 10% higher post-cryogenic viability assemblage of biological cell structures over traditional post-cryogenic cells of a similar character and thermal treatment.
12. A cryopreservation composition as described in clause 11 or any other clause wherein said increased lipid surface 17. energy content cryopreservation fluid comprises a cryopreservation fluid containing a lipid having its surface energy increased by at least about 650 j/kg surface energy.
13. A cryopreservation composition as described in clause 11 or any other clause wherein said increased lipid surface energy content cryopreservation fluid comprises a cryopreservation fluid containing a lipid having its number of drops in said cryopreservation fluid increased by at least about 50 times.
14. A cryopreservation composition as described in clause 11 or 12 or any other clause wherein said increased lipid surface energy content cryopreservation fluid comprises a cryopreservation fluid containing a substance having its number of drops in said cryopreservation fluid increased by at least about 50000 times.
15. A cryopreservation composition as described in clause 11 or any other clause wherein said increased lipid surface energy content cryopreservation fluid comprises a larger drop rended cryopreservation fluid.
16. A cryopreservation composition as described in clause 15 or any other clause wherein said larger drop rended cryopreservation fluid comprises a cryopreservation fluid containing a substance having no substantial number of droplets having a diameter larger than about 1000 nm.
17. A cryopreservation composition as described in clause 15 or any other clause wherein said larger drop rended cryopreservation fluid comprises a cryopreservation fluid containing a substance having no substantial number of droplets having a diameter larger than about 200 nm.
18. A cryopreservation composition as described in clause 11, 12, 16, or 17, or any other clause wherein said enhanced cryogenic viability assemblage of biological cell structures comprises an assemblage of biological cell structures selected from a group consisting of:
   an assemblage of enhanced cryogenic viability blood cell structures,
   an assemblage of enhanced cryogenic viability stem cell structures,
   an assemblage of enhanced cryogenic viability skin cells,
   an assemblage of enhanced cryogenic viability embryonic stem cells,
   an assemblage of enhanced cryogenic viability neural stem cells,
   an assemblage of enhanced cryogenic viability epithelial stem cells
   an assemblage of enhanced cryogenic viability cardiac stem cells
   an assemblage of enhanced cryogenic viability muscle stem cells
   an assemblage of enhanced cryogenic viability connective stem cells
   an assemblage of enhanced cryogenic viability epithelial cells
   an assemblage of enhanced cryogenic viability cardiac cells
   an assemblage of enhanced cryogenic viability muscle cells
   an assemblage of enhanced cryogenic viability connective cells
   an assemblage of enhanced cryogenic viability of nerve cells
   an assemblage of enhanced cryogenic viability umbilical cord blood cells,
   an assemblage of enhanced cryogenic viability histological sample cells,
   an assemblage of enhanced cryogenic viability plant seed cells,
   an assemblage of enhanced cryogenic viability plant shoot cells,
   an assemblage of enhanced cryogenic viability ovarian tissue cell structures,
   an assemblage of enhanced cryogenic viability testicular tissue cell structures,
   an assemblage of enhanced cryogenic viability embryo cells,
   an assemblage of enhanced cryogenic viability tumorous tissue cell structures,
   an assemblage of enhanced cryogenic viability yeast cells,
   an assemblage of enhanced cryogenic viability bacterial cells,
   an assemblage of enhanced cryogenic viability algal cells,
   an assemblage of enhanced cryogenic viability fungal cells,
   an assemblage of enhanced cryogenic viability mesenchymal cells,
   an assemblage of enhanced cryogenic viability keratinocyte cells,
   an assemblage of enhanced cryogenic viability melanocyte cells,
   an assemblage of enhanced cryogenic viability hepatocyte cells,
   an assemblage of enhanced cryogenic viability oocyte cells, and
   an assemblage of enhanced cryogenic viability sperm cell structures,
19. A process to enhance the cryopreservation of biological cells comprising the steps of:
   assembling a cellular collection containing a plurality of biological cell structures;
   establishing a cryopreservation fluid to be incorporated with said biological cell structures in cryopreservation;
   adding energy to said cryopreservation fluid to create an energy increased cryopreservation fluid;
   mixing said energy increased cryopreservation fluid and said biological cell structures to form an energy increased fluidic cryopreservation composite;
   removing thermal energy from said fluidic cryopreservation composite; and
   freezing said fluidic cryopreservation composite by reducing the temperature of said fluidic cryopreservation composite below the freezing point of water.
20. A process to enhance the cryopreservation of biological cells as described in clause 19 or any other clause and further comprising the step of providing an enhanced post-cryogenic viability for said biological cell structures.
21. A process to enhance the cryopreservation of biological cells as described in clause 19 or any other clause wherein said step of providing an enhanced post-cryogenic viability for said biological cell structures comprises the step of providing relatively high post-cryogenic viability for said biological cell structures.
22. A process to enhance the cryopreservation of biological cells as described in clause 20 or any other clause wherein said step of providing relatively high post-cryogenic viability for said biological cell structures comprises a step selected from a group consisting of the steps of:
   providing at least about 5% higher post-cryogenic viability for said biological cell structures over traditional post-cryogenic cell structures of a similar character and thermal treatment,
   providing at least about 10% higher post-cryogenic viability for said biological cell structures over traditional post-cryogenic cell structures of a similar character and thermal treatment, providing at least about 15% higher post-cryogenic viability for said biological cell structures over traditional post-cryogenic cell structures of a similar character and thermal treatment, providing at least about 20% higher post-cryogenic viability for said biological cell structures over traditional post-cryogenic cell structures of a similar character and thermal treatment, and providing at least about 25% higher post-cryogenic viability for said biological cell structures over traditional post-cryogenic cell structures of a similar character and thermal treatment.

23. A process to enhance the cryopreservation of biological cells as described in clause 21 or any other clause wherein said step of providing relatively high post-cryogenic viability for said biological cell structures comprises a step selected from a group consisting of the steps of:
providing not less than about 80% of the pre-cryogenic viability for said biological cell structures,
providing not less than about 70% of the pre-cryogenic viability for said biological cell structures,
providing not less than about 60% of the pre-cryogenic viability for said biological cell structures,
providing not less than about 50% of the pre-cryogenic viability for said biological cell structures,
providing not less than about 40% of the pre-cryogenic viability for said biological cell structures,
providing not less than about 30% of the pre-cryogenic viability for said biological cell structures, and
providing not less than about 20% of the pre-cryogenic viability for said biological cell structures.

24. A process to enhance the cryopreservation of biological cells as described in clause 21 or any other clause wherein said step of adding energy to said cryopreservation fluid to create an energy increased cryopreservation fluid comprises the step of adding surface energy to a substance in said cryopreservation fluid to create a surface energy increased cryopreservation fluid.

25. A process to enhance the cryopreservation of biological cells as described in clause 24 or any other clause wherein said step of adding surface energy to a substance in said cryopreservation fluid to create a surface energy increased cryopreservation fluid comprises the step of adding substantial surface energy to a substance in said cryopreservation fluid to create a substantially surface energy enhanced cryopreservation fluid.

26. A process to enhance the cryopreservation of biological cells as described in clause 25 or any other clause wherein said step of adding substantial surface energy to a substance in said cryopreservation fluid to create a substantially surface energy enhanced cryopreservation fluid comprises a step selected from a group consisting of the steps of:
adding at least about 100 j/kg surface energy to a substance in said cryopreservation fluid,
adding at least about 270 j/kg surface energy to a substance in said cryopreservation fluid,
adding at least about 320 j/kg surface energy to a substance in said cryopreservation fluid,
adding at least about 650 j/kg surface energy to a substance in said cryopreservation fluid,
adding at least about 1050 j/kg surface energy to a substance in said cryopreservation fluid,
adding at least about 3600 j/kg surface energy to a substance in said cryopreservation fluid, and
adding at least about 5200 j/kg surface energy to a substance in said cryopreservation fluid.

27. A process to enhance the cryopreservation of biological cells as described in clause 25 or any other clause wherein said step of adding substantial surface energy to a substance in said cryopreservation fluid to create a substantially surface energy enhanced cryopreservation fluid comprises a step selected from a group consisting of the steps of:
increasing a surface energy of a substance in said cryopreservation fluid to at least about 200 j/kg surface energy,
increasing a surface energy of a substance in said cryopreservation fluid to at least about 420 j/kg surface energy,
increasing a surface energy of a substance in said cryopreservation fluid to at least about 760 j/kg surface energy,
increasing a surface energy of a substance in said cryopreservation fluid to at least about 1200 j/kg surface energy,
increasing a surface energy of a substance in said cryopreservation fluid to at least about 3800 j/kg surface energy, and
increasing a surface energy of a substance in said cryopreservation fluid to at least about 5400 j/kg surface energy.

28. A process to enhance the cryopreservation of biological cells as described in clause 25 or any other clause wherein said step of adding substantial surface energy to a substance in said cryopreservation fluid to create a substantially surface energy enhanced cryopreservation fluid comprises a step selected from a group consisting of the steps of:
increasing the surface energy of a substance in said cryopreservation fluid by at least about 30%,
increasing the surface energy of a substance in said cryopreservation fluid by at least about 50%,
increasing the surface energy of a substance in said cryopreservation fluid by at least about 100%,
increasing the surface energy of a substance in said cryopreservation fluid by at least about 3 times,
increasing the surface energy of a substance in said cryopreservation fluid by at least about 5 times,
increasing the surface energy of a substance in said cryopreservation fluid by at least about 10 times,
increasing the surface energy of a substance in said cryopreservation fluid by at least about 30 times, and
increasing the surface energy of a substance in said cryopreservation fluid by at least about 50 times.

29. A process to enhance the cryopreservation of biological cells as described in clause 19, 25, 27, 28 or any other clause wherein said step of adding energy to said cryopreservation fluid to create an energy increased cryopreservation fluid comprises the step of structurally altering a substance in said cryopreservation fluid.

30. A process to enhance the cryopreservation of biological cells as described in clause 29 or any other clause wherein said step of structurally altering a substance in said cryopreservation fluid comprises the step of structurally storing energy in a substance in said cryopreservation fluid.

31. A process to enhance the cryopreservation of biological cells as described in clause 29 or any other clause wherein said step of structurally altering a substance in said cryopreservation fluid comprises the step of drop transforming a substance in said cryopreservation fluid.

32. A process to enhance the cryopreservation of biological cells as described in clause 31 or any other clause wherein said step of drop transforming a substance in said cryopreservation fluid comprises a step selected from a group consisting of the steps of:
  transforming a substance in said cryopreservation fluid into droplets numbering at least about 30 times the number of initial drops of said substance in said cryopreservation fluid,
  transforming a substance in said cryopreservation fluid into droplets numbering at least about 50 times the number of initial drops of said substance in said cryopreservation fluid,
  transforming a substance in said cryopreservation fluid into droplets numbering at least about 100 times the number of initial drops of said substance in said cryopreservation fluid,
  transforming a substance in said cryopreservation fluid into droplets numbering at least about 500 times the number of initial drops of said substance in said cryopreservation fluid,
  transforming a substance in said cryopreservation fluid into droplets numbering at least about 1000 times the number of initial drops of said substance in said cryopreservation fluid,
  transforming a substance in said cryopreservation fluid into droplets numbering at least about 5000 times the number of initial drops of said substance in said cryopreservation fluid,
  transforming a substance in said cryopreservation fluid into droplets numbering at least about 10000 times the number of initial drops of said substance in said cryopreservation fluid,
  transforming a substance in said cryopreservation fluid into droplets numbering at least about 50000 times the number of initial drops of said substance in said cryopreservation fluid, and
  transforming a substance in said cryopreservation fluid into droplets numbering at least about 100000 times the number of initial drops of said substance in said cryopreservation fluid.

33. A process to enhance the cryopreservation of biological cells as described in clause 24 or any other clause wherein said step of adding energy to said cryopreservation fluid to create an energy increased cryopreservation fluid comprises the step of rending larger drops of a substance in said cryopreservation fluid to form smaller droplets of said substance in said cryopreservation fluid.

34 A process to enhance the cryopreservation of biological cells as described in clause 33 or any other clause wherein said step of rending larger drops of a substance in said cryopreservation fluid to form smaller droplets of said substance in said cryopreservation fluid comprises a step selected from a group consisting of the steps of:
  rending larger drops of a substance in said cryopreservation fluid so there are no substantial amount of droplets larger than about 1000 nm in said substance in said cryopreservation fluid,
  rending larger drops of a substance in said cryopreservation fluid so there are no substantial amount of droplets larger than about 900 nm in said substance in said cryopreservation fluid,
  rending larger drops of a substance in said cryopreservation fluid so there are no substantial amount of droplets larger than about 700 nm in said substance in said cryopreservation fluid,
  rending larger drops of a substance in said cryopreservation fluid so there are no substantial amount of droplets larger than about 500 nm in said substance in said cryopreservation fluid,
  rending larger drops of a substance in said cryopreservation fluid so there are no substantial amount of droplets larger than about 300 nm in said substance in said cryopreservation fluid,
  rending larger drops of a substance in said cryopreservation fluid so there are no substantial amount of droplets larger than about 100 nm in said substance in said cryopreservation fluid,
  rending larger drops of a substance in said cryopreservation fluid so there are no substantial amount of droplets larger than about 70 nm in said substance in said cryopreservation fluid,
  rending larger drops of a substance in said cryopreservation fluid so there are no substantial amount of droplets larger than about 50 nm in said substance in said cryopreservation fluid, and
  rending larger drops of a substance in said cryopreservation fluid so there are no substantial amount of droplets larger than about 30 nm in said substance in said cryopreservation fluid.

35. A process to enhance the cryopreservation of biological cells as described in clause 34 or any other clause wherein said step of rending larger drops of a substance in said cryopreservation fluid to form smaller droplets of said substance in said cryopreservation fluid comprises a step selected from a group consisting of the steps of:
  rending said substance in said cryopreservation fluid so that at least about 20% of said droplets of said substance in said cryopreservation fluid are droplets at least about as small as said desired size,
  rending said substance in said cryopreservation fluid so that at least about 40% of said droplets of said substance in said cryopreservation fluid are droplets at least about as small as said desired size,
  rending said substance in said cryopreservation fluid so that at least about 60% of said droplets of said substance in said cryopreservation fluid are droplets at least about as small as said desired size,
  rending said substance in said cryopreservation fluid so that at least about 80% of said droplets of said substance in said cryopreservation fluid are droplets at least about as small as said desired size, and
  rending said substance in said cryopreservation fluid so that at least about 90% of said droplets of said substance in said cryopreservation fluid are droplets at least about as small as said desired size.

36. A process to enhance the cryopreservation of biological cells as described in clause 19, 24, 26, 27, 28, 34 or 35 or any other clause wherein said step of establishing a cryopreservation fluid to be incorporated with said biological cell structures in cryopreservation comprises a step selected from a group consisting of the steps of:
  establishing a sea buckthorn lipid containing cryoprotective fluid to be incorporated with said biological cell structures,
  establishing an unsaturated fatty acid containing cryoprotective fluid to be incorporated with said biological cell structures
  establishing a saturated fatty acid containing cryoprotective fluid to be incorporated with said biological cell structures establishing a palmitic acid containing cryoprotective fluid to be incorporated with said biological cell structures,
establishing a palmitoleic acid containing cryoprotective fluid to be incorporated with said biological cell structures,
establishing a oleic acid containing cryoprotective fluid to be incorporated with said biological cell structures,
establishing a linoleic acid containing cryoprotective fluid to be incorporated with said biological cell structures,
establishing a linolenic acid containing cryoprotective fluid to be incorporated with said biological cell structures,
establishing a lecithin containing cryoprotective fluid to be incorporated with said biological cell structures,
establishing a β-sitosterol containing cryoprotective fluid to be incorporated with said biological cell structures,
establishing a β-amyrin containing cryoprotective fluid to be incorporated with said biological cell structures,
establishing a γ-carotene containing cryoprotective fluid to be incorporated with said biological cell structures,
establishing a α-amyrin containing cryoprotective fluid to be incorporated with said biological cell structures,
establishing a β-carotene containing cryoprotective fluid to be incorporated with said biological cell structures,
establishing a lycopene containing cryoprotective fluid to be incorporated with said biological cell structures,
establishing a lutein containing cryoprotective fluid to be incorporated with said biological cell structures,
establishing a tocopherol containing cryoprotective fluid to be incorporated with said biological cell structures,
establishing a phosphatidylethanolamine containing cryoprotective fluid to be incorporated with said biological cell structures,
establishing a digalactosyldiacylglycerol lipid containing cryoprotective fluid to be incorporated with said biological cell structures,
establishing a monogalactosymonoacylglycerol containing cryoprotective fluid to be incorporated with said biological cell structures,
establishing a 16:1 fatty acid containing cryoprotective fluid to be incorporated with said biological cell structures,
establishing a 18:1 fatty acid containing cryoprotective fluid to be incorporated with said biological cell structures,
establishing a 18:2 fatty acid containing cryoprotective fluid to be incorporated with said biological cell structures, and
establishing a 18:3 fatty acid containing cryoprotective fluid to be incorporated with said biological cell structures.

37. A process to enhance the cryopreservation of biological cells as described in clause 36 or any other clause wherein said step of establishing a lipid containing cryoprotective fluid to be incorporated with said biological cell structures comprises the step of establishing a high lipid concentration cryopreservation fluid to be incorporated with said biological cell structures.

38. A process to enhance the cryopreservation of biological cells as described in clause 37 or any other clause wherein said step of establishing a high lipid concentration cryopreservation fluid to be incorporated with said biological cell structures comprises a step selected from a group consisting of the steps of:
establishing an at least about 10% higher than traditional lipid concentration cryopreservation fluid as compared to similar fluid of similar character for similar thermal treatment to be incorporated with said biological cell structures,
establishing an at least about 20% higher than traditional lipid concentration cryopreservation fluid as compared to similar fluid of similar character for similar thermal treatment to be incorporated with said biological cell structures,
establishing an at least about 40% higher than traditional lipid concentration cryopreservation fluid as compared to similar fluid of similar character for similar thermal treatment to be incorporated with said biological cell structures,
establishing an at least about 60% higher than traditional lipid concentration cryopreservation fluid as compared to similar fluid of similar character for similar thermal treatment to be incorporated with said biological cell structures, and
establishing an at least about 80% higher than traditional lipid concentration cryopreservation fluid as compared to similar fluid of similar character for similar thermal treatment to be incorporated with said biological cell structures.

39. A process to enhance the cryopreservation of biological cells as described in clause 37 or any other clause wherein said step of establishing a high lipid concentration cryopreservation fluid to be incorporated with said biological cell structures comprises the step of establishing a component selected from a group consisting of: a relatively high concentration sea buckthorn lipid, a relatively high concentration unsaturated fatty acid, a relatively high concentration saturated fatty acid, a relatively high concentration palmitic acid, a relatively high concentration palmitoleic acid, a relatively high concentration oleic acid, a relatively high concentration linoleic acid, a relatively high concentration linolenic acid, a relatively high concentration lecithin, a relatively high concentration β-sitosterol, a relatively high concentration β-amyrin, a relatively high concentration γ-carotene, a relatively high concentration α-amyrin, a relatively high concentration β-carotene, a relatively high concentration lycopene, a relatively high concentration lutein, a relatively high concentration tocopherol, a relatively high concentration digalactosyldiacylglycerol, a relatively high concentration monogalactosymonoacylglycerol, a relatively high concentration 16:1 fatty acids, a relatively high concentration 18:1 fatty acids, a relatively high concentration 18:2 fatty acids, and a relatively high concentration 18:3 fatty acid.

40. A process to enhance the cryopreservation of biological cells as described in clause 19 or any other clause wherein said step of assembling a cellular collection containing a plurality of biological cell structures comprises a step selected from a group consisting of the steps of:
assembling a cellular collection containing a plurality of blood cell structures,
assembling a cellular collection containing a plurality of stem cell structures,
assembling a cellular collection containing a plurality of skin cells,
assembling a cellular collection containing a plurality of embryonic stem cells,
assembling a cellular collection containing a plurality of neural stem cells,
assembling a cellular collection containing a plurality of epithelial stem cells assembling a cellular collection containing a plurality of cardiac stem cells
assembling a cellular collection containing a plurality of muscle stem cells
assembling a cellular collection containing a plurality of connective stem cells
assembling a cellular collection containing a plurality of epithelial cells
assembling a cellular collection containing a plurality of cardiac cells
assembling a cellular collection containing a plurality of muscle cells
assembling a cellular collection containing a plurality of connective cells
assembling a cellular collection containing a plurality of nerve cells
assembling a cellular collection containing a plurality of umbilical cord blood cells,
assembling a cellular collection containing a plurality of histological sample cells,
assembling a cellular collection containing a plurality of plant seed cells,
assembling a cellular collection containing a plurality of plant shoot cells,
assembling a cellular collection containing a plurality of ovarian tissue cell structures,
assembling a cellular collection containing a plurality of testicular tissue cell structures,
assembling a cellular collection containing a plurality of embryo cells,
assembling a cellular collection containing a plurality of tumorous tissue cell structures,
assembling a cellular collection containing a plurality of yeast cells,
assembling a cellular collection containing a plurality of bacterial cells,
assembling a cellular collection containing a plurality of algal cells,
assembling a cellular collection containing a plurality of fungal cells,
assembling a cellular collection containing a plurality of mesenchymal cells,
assembling a cellular collection containing a plurality of keratinocyte cells,
assembling a cellular collection containing a plurality of melanocyte cells,
assembling a cellular collection containing a plurality of hepatocyte cells,
assembling a cellular collection containing a plurality of oocyte cells, and
assembling a cellular collection containing a plurality of sperm cells.

41. A process to enhance the cryopreservation of biological cells comprising the steps of:
assembling a cellular collection containing a plurality of biological cell structures;
establishing a cryopreservation fluid to be incorporated with said biological cell structures in cryopreservation;
establishing non-naturally occurring lipid droplets within said cryopreservation fluid to create a non-natural lipid containing cryopreservation fluid;
mixing said non-natural lipid containing cryopreservation fluid and said biological cell structures to form a non-natural fluidic cryopreservation composite;
removing thermal energy from said non-natural fluidic cryopreservation composite; and
freezing said non-natural fluidic cryopreservation composite by reducing the temperature of said non-natural fluidic cryopreservation composite below the freezing point of water.

42. A process to enhance the cryopreservation of biological cells as described in clause 41 or any other clause wherein said step of said establishing non-natural lipid containing cryopreservation fluid and said biological cell structures to form a non-natural fluidic cryopreservation composite comprises the step of creating unstably sized lipid droplets within said cryopreservation fluid.

43. A cryopreservation composition as described in clause 41 or any other clause wherein said step of establishing non-natural lipid containing cryopreservation fluid and said biological cell structures to form a non-natural fluidic cryopreservation composite comprises the step of modifying the size of said lipid droplets contained within said cryopreservation fluid.

44. A cryopreservation composition as described in clause 43 or any other clause wherein said step of creating modified sized lipid droplets within said cryopreservation fluid comprises a step selected from a group consisting of the steps of:
creating a substance in said cryopreservation fluid with droplets numbering at least about 30 times the number of initial drops of said substance in said cryopreservation fluid,
creating a substance in said cryopreservation fluid with droplets numbering at least about 50 times the number of initial drops of said substance in said cryopreservation fluid,
creating a substance in said cryopreservation fluid with droplets numbering at least about 100 times the number of initial drops of said substance in said cryopreservation fluid,
creating a substance in said cryopreservation fluid with droplets numbering at least about 500 times the number of initial drops of said substance in said cryopreservation fluid,
creating a substance in said cryopreservation fluid with droplets numbering at least about 1000 times the number of initial drops of said substance in said cryopreservation fluid,
creating a substance in said cryopreservation fluid with droplets numbering at least about 5000 times the number of initial drops of said substance in said cryopreservation fluid,
creating a substance in said cryopreservation fluid with droplets numbering at least about 10000 times the number of initial drops of said substance in said cryopreservation fluid,
creating a substance in said cryopreservation fluid with droplets numbering at least about 50000 times the number of initial drops of said substance in said cryopreservation fluid, and
creating a substance in said cryopreservation fluid with droplets numbering at least about 100000 times the number of initial drops of said substance in said cryopreservation fluid.

45. A process to enhance the cryopreservation of biological cells as described in clause 41 or any other clause wherein said step of establishing non-naturally occurring lipid droplets within said cryopreservation fluid to create a non-natural lipid containing cryopreservation fluid comprises the step of creating a substantial number of relatively small lipid droplets in a substance contained within said cryopreservation fluid.

46. A process to enhance the cryopreservation of biological cells as described in clause 45 or any other clause wherein said step creating of a substantial number of relatively small lipid droplets in a substance contained within said cryopreservation fluid comprises the step of rending larger drops of a substance in said cryopreservation fluid to form smaller droplets of said substance in said cryopreservation fluid.

47. A process to enhance the cryopreservation of biological cells as described in clause 44, 45, or 46 or any other clause wherein said step of creating a substantial number of relatively small lipid droplets in a substance contained within said cryopreservation fluid comprises a step selected from a group consisting of the steps of:
   creating a substantial number of droplets of a substance contained within said cryopreservation fluid with no substantial amount of droplets larger than at least about 1000 nm,
   creating a substantial number of droplets of a substance contained within said cryopreservation fluid with no substantial amount of droplets larger than at least about 900 nm,
   creating a substantial number of droplets of a substance contained within said cryopreservation fluid with no substantial amount of droplets larger than at least about 700 nm,
   creating a substantial number of droplets of a substance contained within said cryopreservation fluid with no substantial amount of droplets larger than at least about 500 nm,
   creating a substantial number of droplets of a substance contained within said cryopreservation fluid with no substantial amount of droplets larger than at least about 300 nm,
   creating a substantial number of droplets of a substance contained within said cryopreservation fluid with no substantial amount of droplets larger than at least about 100 nm,
   creating a substantial number of droplets of a substance contained within said cryopreservation fluid with no substantial amount of droplets larger than at least about 70 nm,
   creating a substantial number of droplets of a substance contained within said cryopreservation fluid with no substantial amount of droplets larger than at least about 50 nm, and
   creating a substantial number of droplets of a substance contained within said cryopreservation fluid with no substantial amount of droplets larger than at least about 30 nm.

48. A process to enhance the cryopreservation of biological cells as described in clause 45 or 46 or any other clause wherein said step of creating a substantial number of relatively small lipid droplets in a substance contained within said cryopreservation fluid comprises a step selected from a group consisting of the steps of:
   creating said droplets in said cryopreservation fluid so that at least about 20% of said droplets of said substance in said cryopreservation fluid are droplets at least about as small as said desired size,
   creating said droplets in said cryopreservation fluid so that at least about 40% of said droplets of said substance in said cryopreservation fluid are droplets at least about as small as said desired size,
   creating said droplets in said cryopreservation fluid so that at least about 60% of said droplets of said substance in said cryopreservation fluid are droplets at least about as small as said desired size,
   creating said droplets in said cryopreservation fluid so that at least about 80% of said droplets of said substance in said cryopreservation fluid are droplets at least about as small as said desired size, and
   creating said droplets in said cryopreservation fluid so that at least about 90% of said droplets of said substance in said cryopreservation fluid are droplets at least about as small as said desired size.

49. A process to enhance the cryopreservation of biological cells as described in clause 45 or 46 or any other clause wherein said step of creating a substantial number of relatively small lipid droplets in a substance contained within said cryopreservation fluid comprises a step selected from a group consisting of the steps of:
   creating a substance in said cryopreservation fluid with droplets numbering at least about 30 times the number of initial drops of said substance in said cryopreservation fluid,
   creating a substance in said cryopreservation fluid with droplets numbering at least about 50 times the number of initial drops of said substance in said cryopreservation fluid,
   creating a substance in said cryopreservation fluid with droplets numbering at least about 100 times the number of initial drops of said substance in said cryopreservation fluid,
   creating a substance in said cryopreservation fluid with droplets numbering at least about 500 times the number of initial drops of said substance in said cryopreservation fluid,
   creating a substance in said cryopreservation fluid with droplets numbering at least about 1000 times the number of initial drops of said substance in said cryopreservation fluid,
   creating a substance in said cryopreservation fluid with droplets numbering at least about 5000 times the number of initial drops of said substance in said cryopreservation fluid,
   creating a substance in said cryopreservation fluid with droplets numbering at least about 10000 times the number of initial drops of said substance in said cryopreservation fluid,
   creating a substance in said cryopreservation fluid with droplets numbering at least about 50000 times the number of initial drops of said substance in said cryopreservation fluid, and
   creating a substance in said cryopreservation fluid with droplets numbering at least about 100000 times the number of initial drops of said substance in said cryopreservation fluid.

50. A process to enhance the cryopreservation of biological cells as described in clause 41, 44, or 46 or any other clause wherein said step of assembling a cellular collection containing a plurality of biological cell structures comprises a step selected from a group consisting of the steps of:
   assembling a cellular collection containing a plurality of blood cell structures,
   assembling a cellular collection containing a plurality of stem cell structures,
   assembling a cellular collection containing a plurality of skin cells, assembling a cellular collection containing a plurality of embryonic stem cells,
assembling a cellular collection containing a plurality of neural stem cells,
assembling a cellular collection containing a plurality of epithelial stem cells
assembling a cellular collection containing a plurality of cardiac stem cells
assembling a cellular collection containing a plurality of muscle stem cells
assembling a cellular collection containing a plurality of connective stem cells
assembling a cellular collection containing a plurality of epithelial cells
assembling a cellular collection containing a plurality of cardiac cells
assembling a cellular collection containing a plurality of muscle cells
assembling a cellular collection containing a plurality of connective cells
assembling a cellular collection containing a plurality of nerve cells
assembling a cellular collection containing a plurality of umbilical cord blood cells,
assembling a cellular collection containing a plurality of histological sample cells,
assembling a cellular collection containing a plurality of plant seed cells,
assembling a cellular collection containing a plurality of plant shoot cells,
assembling a cellular collection containing a plurality of ovarian tissue cell structures,
assembling a cellular collection containing a plurality of testicular tissue cell structures,
assembling a cellular collection containing a plurality of embryo cells,
assembling a cellular collection containing a plurality of tumorous tissue cell structures,
assembling a cellular collection containing a plurality of yeast cells,
assembling a cellular collection containing a plurality of bacterial cells,
assembling a cellular collection containing a plurality of algal cells,
assembling a cellular collection containing a plurality of fungal cells,
assembling a cellular collection containing a plurality of mesenchymal cells,
assembling a cellular collection containing a plurality of keratinocyte cells,
assembling a cellular collection containing a plurality of melanocyte cells,
assembling a cellular collection containing a plurality of hepatocyte cells,
assembling a cellular collection containing a plurality of oocyte cells, and
assembling a cellular collection containing a plurality of sperm cells.

51. A process to enhance the cryopreservation of biological cells as described in clause 41 or any other clause wherein said step of establishing non-naturally occurring lipid droplets within said cryopreservation fluid to create a non-natural lipid cryopreservation fluid comprises the step of creating a substantially uniform maximum droplet size of a substance contained within said cryopreservation fluid.

52. A process to enhance the cryopreservation of biological cells as described in clause 51 or any other clause wherein said step of creating a substantially uniform maximum droplet size of a substance contained within said cryopreservation fluid comprises the step selected from a group consisting of:
causing a substance contained within said cryopreservation fluid to have no substantial number of droplets larger than at least about 1000 nm,
causing a substance contained within said cryopreservation fluid to have no substantial number of droplets larger than at least about 900 nm,
causing a substance contained within said cryopreservation fluid to have no substantial number of droplets larger than at least about 700 nm,
causing a substance contained within said cryopreservation fluid to have no substantial number of droplets larger than at least about 500 nm,
causing a substance contained within said cryopreservation fluid to have no substantial number of droplets larger than at least about 300 nm,
causing a substance contained within said cryopreservation fluid to have no substantial number of droplets larger than at least about 100 nm,
causing a substance contained within said cryopreservation fluid to have no substantial number of droplets larger than at least about 70 nm,
causing a substance contained within said cryopreservation fluid to have no substantial number of droplets larger than at least about 50 nm, and
causing a substance contained within said cryopreservation fluid to have no substantial number of droplets larger than at least about 30 nm.

53. A process to enhance the cryopreservation of biological cells as described in clause 51 or any other clause wherein said step of creating a substantially uniform maximum droplet size of a substance contained within said cryopreservation fluid comprises a step selected from a group consisting of the steps of:
eliminating droplets of a substance contained within said cryopreservation fluid so there are no substantial amount of droplets larger than at least about 1000 nm,
eliminating droplets of a substance contained within said cryopreservation fluid so there are no substantial amount of droplets larger than at least about 900 nm,
eliminating droplets of a substance contained within said cryopreservation fluid so there are no substantial amount of droplets larger than at least about 700 nm,
eliminating droplets of a substance contained within said cryopreservation fluid so there are no substantial amount of droplets larger than at least about 500 nm,
eliminating droplets of a substance contained within said cryopreservation fluid so there are no substantial amount of droplets larger than at least about 300 nm,
eliminating droplets of a substance contained within said cryopreservation fluid so there are no substantial amount of droplets larger than at least about 100 nm,
e eliminating droplets of a substance contained within said cryopreservation fluid so there are no substantial amount of droplets larger than at least about 70 nm,
eliminating droplets of a substance contained within said cryopreservation fluid so there are no substantial amount of droplets larger than at least about 50 nm, and
eliminating droplets of a substance contained within said cryopreservation fluid so there are no substantial amount of droplets larger than at least about 30 nm.

54. A process to enhance the cryopreservation of biological cells as described in clause 41 or any other clause wherein said step of establishing non-naturally occurring lipid droplets within said cryopreservation fluid to create a non-natural lipid cryopreservation fluid comprises the step of causing a substance contained within said cryopreservation fluid to have a droplet size with a skewed size distribution that favors smaller size droplets.

55. A process to enhance the cryopreservation of biological cells as described in clause 54 or any other clause wherein the step of causing a substance contained within said cryopreservation fluid to have a droplet size with a skewed size distribution that favors smaller size droplets a step selected from a group consisting of the steps of:
    modifying a substance contained within said cryopreservation fluid to have a mode drop size of less than at least about 1000 nm,
    modifying a substance contained within said cryopreservation fluid to have a mode drop size of less than at least about 900 nm,
    modifying a substance contained within said cryopreservation fluid to have a mode drop size of less than at least about 700 nm,
    modifying a substance contained within said cryopreservation fluid to have a mode drop size of less than at least about 500 nm,
    modifying a substance contained within said cryopreservation fluid to have a mode drop size of less than at least about 300 nm,
    modifying a substance contained within said cryopreservation fluid to have a mode drop size of less than at least about 100 nm,
    modifying a substance contained within said cryopreservation fluid to have a mode drop size of less than at least about 70 nm,
    modifying a substance contained within said cryopreservation fluid to have a mode drop size of less than at least about 50 nm, and
    modifying a substance contained within said cryopreservation fluid to have a mode drop size of less than at least about 30 nm.

56. A process to enhance the cryopreservation of biological cells comprising the steps of:
    assembling a cellular collection containing a plurality of biological cell structures;
    establishing a high lipid concentration cryopreservation fluid to be incorporated with said biological cell structures in cryopreservation;
    altering at least one characteristic of a lipid substance in said high lipid concentration cryopreservation fluid in a manner that enhances cell viability;
    mixing said altered high lipid concentration cryopreservation fluid and said biological cell structures to form a vitality enhanced fluidic cryopreservation composite;
    removing thermal energy from said fluidic cryopreservation composite; and
    freezing said fluidic cryopreservation composite by reducing the temperature of said fluidic cryopreservation composite below the freezing point of water.

57. A process to enhance the cryopreservation of biological cells as described in clause 56 or any other clause wherein said step of establishing a high lipid concentration cryopreservation fluid to be incorporated with said biological cell structures in cryopreservation comprises a step selected from a group consisting of the steps of:
    establishing an at least about 10% higher than traditional lipid concentration cryopreservation fluid as compared to similar fluid of similar character for similar thermal treatment to be incorporated with said biological cell structures,
    establishing an at least about 20% higher than traditional lipid concentration cryopreservation fluid as compared to similar fluid of similar character for similar thermal treatment to be incorporated with said biological cell structures,
    establishing an at least about 40% higher than traditional lipid concentration cryopreservation fluid as compared to similar fluid of similar character for similar thermal treatment to be incorporated with said biological cell structures,
    establishing an at least about 60% higher than traditional lipid concentration cryopreservation fluid as compared to similar fluid of similar character for similar thermal treatment to be incorporated with said biological cell structures, and
    establishing an at least about 80% higher than traditional lipid concentration cryopreservation fluid as compared to similar fluid of similar character for similar thermal treatment to be incorporated with said biological cell structures.

58. A process to enhance the cryopreservation of biological cells as described in clause 56 or any other clause wherein said step of establishing a high lipid concentration cryopreservation fluid to be incorporated with said biological cell structures in cryopreservation comprises the step of establishing a component selected from a group consisting of: a relatively high concentration sea buckthorn lipid, a relatively high concentration saturated fatty acid, a relatively high concentration unsaturated fatty acid, a relatively high concentration palmitic acid, a relatively high concentration palmitoleic acid, a relatively high concentration oleic acid, a relatively high concentration linoleic acid, a relatively high concentration linolenic acid, a relatively high concentration lecithin, a relatively high concentration β-sitosterol, a relatively high concentration β-amyrin, a relatively high concentration γ-carotene, a relatively high concentration α-amyrin, a relatively high concentration β-carotene, a relatively high concentration lycopene, a relatively high concentration lutein, a relatively high concentration tocopherol, a relatively high concentration digalactosyldiacylglycerol, a relatively high concentration monogalactosymonoacylglycerol, a relatively high concentration 16:1 fatty acids, a relatively high concentration 18:1 fatty acids, a relatively high concentration 18:2 fatty acids, and a relatively high concentration 18:3 fatty acid.

59. A process to enhance the cryopreservation of biological cells as described in clause 56 or any other clause and further comprising the step of providing an enhanced post-cryogenic viability for said biological cell structures.

60. A process to enhance the cryopreservation of biological cells as described in clause 59 or any other clause wherein said step of providing an enhanced post-cryogenic viability for said biological cell structures comprises the step of providing relatively high post-cryogenic viability for said biological cell structures.

61. A process to enhance the cryopreservation of biological cells as described in clause 60 or any other clause wherein said step of providing relatively high post-cryogenic viability for said biological cell structures comprises a step selected from a group consisting of the steps of:

providing at least about 5% higher post-cryogenic viability for said biological cell structures over traditional post-cryogenic cell structures of a similar character and thermal treatment,
providing at least about 10% higher post-cryogenic viability for said biological cell structures over traditional post-cryogenic cell structures of a similar character and thermal treatment,
providing at least about 15% higher post-cryogenic viability for said biological cell structures over traditional post-cryogenic cell structures of a similar character and thermal treatment,
providing at least about 20% higher post-cryogenic viability for said biological cell structures over traditional post-cryogenic cell structures of a similar character and thermal treatment, and
providing at least about 25% higher post-cryogenic viability for said biological cell structures over traditional post-cryogenic cell structures of a similar character and thermal treatment.

62. A process to enhance the cryopreservation of biological cells as described in clause 60 or any other clause wherein said step of providing relatively high post-cryogenic viability for said biological cell structures comprises a step selected from a group consisting of the steps of:
providing not less than about 80% of the pre-cryogenic viability for said biological cell structures,
providing not less than about 70% of the pre-cryogenic viability for said biological cell structures,
providing not less than about 60% of the pre-cryogenic viability for said biological cell structures,
providing not less than about 50% of the pre-cryogenic viability for said biological cell structures,
providing not less than about 40% of the pre-cryogenic viability for said biological cell structures,
providing not less than about 30% of the pre-cryogenic viability for said biological cell structures, and
providing not less than about 20% of the pre-cryogenic viability for said biological cell structures.

63. A process to enhance the cryopreservation of biological cells as described in clause 56, 57, 60, or 62 or any other clause wherein said step of altering at least one characteristic of a lipid substance in said high lipid concentration cryopreservation fluid in a manner that enhances cell viability comprises the step of rending larger drops of a substance in said cryopreservation fluid to form smaller droplets of said substance in said cryopreservation fluid.

64 A process to enhance the cryopreservation of biological cells as described in clause 63 or any other clause wherein said step of rending larger drops of a substance in said cryopreservation fluid to form smaller droplets of said substance in said cryopreservation fluid comprises a step selected from a group consisting of the steps of:
rending larger drops of a substance in said cryopreservation fluid so there are no substantial amount of droplets larger than about 1000 nm for said substance in said cryopreservation fluid,
rending larger drops of a substance in said cryopreservation fluid so there are no substantial amount of droplets larger than about 900 nm for said substance in said cryopreservation fluid,
rending larger drops of a substance in said cryopreservation fluid so there are no substantial amount of droplets larger than about 700 nm for said substance in said cryopreservation fluid,
rending larger drops of a substance in said cryopreservation fluid so there are no substantial amount of droplets larger than about 500 nm for said substance in said cryopreservation fluid,
rending larger drops of a substance in said cryopreservation fluid so there are no substantial amount of droplets larger than about 300 nm for said substance in said cryopreservation fluid,
rending larger drops of a substance in said cryopreservation fluid so there are no substantial amount of droplets larger than about 100 nm for said substance in said cryopreservation fluid,
rending larger drops of a substance in said cryopreservation fluid so there are no substantial amount of droplets larger than about 70 nm for said substance in said cryopreservation fluid,
rending larger drops of a substance in said cryopreservation fluid so there are no substantial amount of droplets larger than about 50 nm for said substance in said cryopreservation fluid, and
rending larger drops of a substance in said cryopreservation fluid so there are no substantial amount of droplets larger than about 30 nm for said substance in said cryopreservation fluid.

65. A process to enhance the cryopreservation of biological cells as described in clause 56 or any other clause wherein said step of assembling a cellular collection containing a plurality of biological cell structures comprises a step selected from a group consisting of the steps of:
assembling a cellular collection containing a plurality of blood cell structures,
assembling a cellular collection containing a plurality of stem cell structures,
assembling a cellular collection containing a plurality of skin cells,
assembling a cellular collection containing a plurality of embryonic stem cells,
assembling a cellular collection containing a plurality of neural stem cells,
assembling a cellular collection containing a plurality of umbilical cord blood cells,
assembling a cellular collection containing a plurality of epithelial stem cells
assembling a cellular collection containing a plurality of cardiac stem cells
assembling a cellular collection containing a plurality of muscle stem cells
assembling a cellular collection containing a plurality of connective stem cells
assembling a cellular collection containing a plurality of epithelial cells
assembling a cellular collection containing a plurality of cardiac cells
assembling a cellular collection containing a plurality of muscle cells
assembling a cellular collection containing a plurality of connective cells
assembling a cellular collection containing a plurality of nerve cells
assembling a cellular collection containing a plurality of histological sample cells,
assembling a cellular collection containing a plurality of plant seed cells,
assembling a cellular collection containing a plurality of plant shoot cells,
assembling a cellular collection containing a plurality of ovarian tissue cell structures, assembling a cellular collection containing a plurality of testicular tissue cell structures,
assembling a cellular collection containing a plurality of embryo cells,
assembling a cellular collection containing a plurality of tumorous tissue cell structures,
assembling a cellular collection containing a plurality of yeast cells,
assembling a cellular collection containing a plurality of bacterial cells,
assembling a cellular collection containing a plurality of algal cells,
assembling a cellular collection containing a plurality of fungal cells,
assembling a cellular collection containing a plurality of mesenchymal cells,
assembling a cellular collection containing a plurality of keratinocyte cells,
assembling a cellular collection containing a plurality of melanocyte cells,
assembling a cellular collection containing a plurality of hepatocyte cells,
assembling a cellular collection containing a plurality of oocyte cells, and
assembling a cellular collection containing a plurality of sperm cells.

66. A process to enhance the cryopreservation of biological cells as described in clause 64 wherein the step of assembling a cellular collection containing a plurality of biological cell structures comprises a step selected from a group consisting of the steps of:
assembling a cellular collection containing a plurality of blood cell structures,
assembling a cellular collection containing a plurality of stem cell structures,
assembling a cellular collection containing a plurality of skin cells,
assembling a cellular collection containing a plurality of embryonic stem cells,
assembling a cellular collection containing a plurality of neural stem cells,
assembling a cellular collection containing a plurality of umbilical cord blood cells,
assembling a cellular collection containing a plurality of epithelial stem cells
assembling a cellular collection containing a plurality of cardiac stem cells
assembling a cellular collection containing a plurality of muscle stem cells
assembling a cellular collection containing a plurality of connective stem cells
assembling a cellular collection containing a plurality of epithelial cells
assembling a cellular collection containing a plurality of cardiac cells
assembling a cellular collection containing a plurality of muscle cells
assembling a cellular collection containing a plurality of connective cells
assembling a cellular collection containing a plurality of nerve cells
assembling a cellular collection containing a plurality of histological sample cells,
assembling a cellular collection containing a plurality of plant seed cells,
assembling a cellular collection containing a plurality of plant shoot cells,
assembling a cellular collection containing a plurality of ovarian tissue cell structures,
assembling a cellular collection containing a plurality of testicular tissue cell structures,
assembling a cellular collection containing a plurality of embryo cells,
assembling a cellular collection containing a plurality of tumorous tissue cell structures,
assembling a cellular collection containing a plurality of yeast cells,
assembling a cellular collection containing a plurality of bacterial cells,
assembling a cellular collection containing a plurality of algal cells,
assembling a cellular collection containing a plurality of fungal cells,
assembling a cellular collection containing a plurality of mesenchymal cells,
assembling a cellular collection containing a plurality of keratinocyte cells,
assembling a cellular collection containing a plurality of melanocyte cells,
assembling a cellular collection containing a plurality of hepatocyte cells,
assembling a cellular collection containing a plurality of oocyte cells, and
assembling a cellular collection containing a plurality of sperm cells.

67. A process to enhance the cryopreservation of biological cells comprising the steps of:
assembling a cellular collection containing a plurality of biological cell structures;
establishing a cryopreservation fluid to be incorporated with said biological cell structures in cryopreservation;
mixing said cryopreservation fluid and said biological cell structures to form a fluidic cryopreservation composite;
subjecting said biological cell structures to said cryopreservation fluid in said fluidic cryopreservation composite in a manner that reduces cryogenic damage to said biological cell structures;
removing thermal energy from said fluidic cryopreservation composite; and
freezing said fluidic cryopreservation composite by reducing the temperature of said fluidic cryopreservation composite below the freezing point of water while reducing cryogenic damage to said biological cell structures.

68. A process to enhance the cryopreservation of biological cells as described in clause 67 or any other clause wherein said step of subjecting said biological cell structures to said cryopreservation fluid in said fluidic cryopreservation composite in a manner that reduces cryogenic damage to said biological cell structures comprises the step of configuring at least one lipid contained within said cryopreservation fluid.

69. A process to enhance the cryopreservation of biological cells as described in clause 67 or any other clause wherein said step of subjecting said biological cell structures to said cryopreservation fluid in said fluidic cryopreservation composite in a manner that reduces cryogenic damage to said biological cell structures comprises the step of altering at least one lipid contained within said cryopreservation fluid.

70. A process to enhance the cryopreservation of biological cells as described in clause 69 or any other clause said step of altering at least one lipid contained within said cryopreservation fluid comprises the step of physically altering at least one lipid contained within said cryopreservation fluid.
71. A process to enhance the cryopreservation of biological cells as described in clause 69 or any other clause said step of altering at least one lipid contained within said cryopreservation fluid comprises the step of in situ physically altering at least one lipid contained within said cryopreservation fluid.
72. A process to enhance the cryopreservation of biological cells as described in clause 71 or any other clause wherein said step of physically altering at least one lipid contained within said cryopreservation fluid comprises the step of rending larger drops of a substance in said cryopreservation fluid to form smaller droplets of said substance in said cryopreservation fluid.
73. A process to enhance the cryopreservation of biological cells as described in clause 67 or any other clause and further comprising the step of thawing said cryopreservation fluid by increasing its temperature above the freezing point of water
74. A process to enhance the cryopreservation of biological cells as described in clause 67 or any other clause and further comprising the step of providing an enhanced post-cryogenic viability for said biological cell structures.
75. A process to enhance the cryopreservation of biological cells as described in clause 74 or any other clause wherein said step of providing an enhanced post-cryogenic viability for said biological cell structures comprises the step of providing relatively high post-cryogenic viability for said biological cell structures.
76. A process to enhance the cryopreservation of biological cells as described in clause 75 or any other clause wherein said step of providing relatively high post-cryogenic viability for said biological cell structures comprises a step selected from a group consisting of the steps of:
    providing at least about 5% higher post-cryogenic viability for said biological cell structures over traditional post-cryogenic cell structures of a similar character and thermal treatment,
    providing at least about 10% higher post-cryogenic viability for said biological cell structures over traditional post-cryogenic cell structures of a similar character and thermal treatment,
    providing at least about 15% higher post-cryogenic viability for said biological cell structures over traditional post-cryogenic cell structures of a similar character and thermal treatment,
    providing at least about 20% higher post-cryogenic viability for said biological cell structures over traditional post-cryogenic cell structures of a similar character and thermal treatment, and
    providing at least about 25% higher post-cryogenic viability for said biological cell structures over traditional post-cryogenic cell structures of a similar character and thermal treatment.
77. A process to enhance the cryopreservation of biological cells as described in clause 75 or any other clause wherein said step of providing relatively high post-cryogenic viability for said biological cell structures comprises a step selected from a group consisting of the steps of:
    providing not less than about 80% of the pre-cryogenic viability for said biological cell structures,
    providing not less than about 70% of the pre-cryogenic viability for said biological cell structures,
    providing not less than about 60% of the pre-cryogenic viability for said biological cell structures,
    providing not less than about 50% of the pre-cryogenic viability for said biological cell structures,
    providing not less than about 40% of the pre-cryogenic viability for said biological cell structures,
    providing not less than about 30% of the pre-cryogenic viability for said biological cell structures, and
    providing not less than about 20% of the pre-cryogenic viability for said biological cell structures.
78. A process to enhance the cryopreservation of biological cells as described in clause 67, 75, or 77 or any other clause wherein said step of subjecting said biological cell structures to said cryopreservation fluid in said fluidic cryopreservation composite in a manner that reduces cryogenic damage to said biological cell structures comprises the step of rending larger drops of a substance in said cryopreservation fluid to form smaller droplets of said substance in said cryopreservation fluid.
79. A process to enhance the cryopreservation of biological cells as described in clause 78 or any other clause wherein said step of rending larger drops of a substance in said cryopreservation fluid to form smaller droplets of said substance in said cryopreservation fluid comprises a step selected from a group consisting of the steps of:
    rending larger drops of a substance in said cryopreservation fluid so there are no substantial amount of droplets larger than about 1000 nm in said substance in said cryopreservation fluid,
    rending larger drops of a substance in said cryopreservation fluid so there are no substantial amount of droplets larger than about 900 nm in said substance in said cryopreservation fluid,
    rending larger drops of a substance in said cryopreservation fluid so there are no substantial amount of droplets larger than about 700 nm in said substance in said cryopreservation fluid,
    rending larger drops of a substance in said cryopreservation fluid so there are no substantial amount of droplets larger than about 500 nm in said substance in said cryopreservation fluid,
    rending larger drops of a substance in said cryopreservation fluid so there are no substantial amount of droplets larger than about 300 nm in said substance in said cryopreservation fluid,
    rending larger drops of a substance in said cryopreservation fluid so there are no substantial amount of droplets larger than about 100 nm in said substance in said cryopreservation fluid,
    rending larger drops of a substance in said cryopreservation fluid so there are no substantial amount of droplets larger than about 70 nm in said substance in said cryopreservation fluid,
    rending larger drops of a substance in said cryopreservation fluid so there are no substantial amount of droplets larger than about 50 nm in said substance in said cryopreservation fluid, and
    rending larger drops of a substance in said cryopreservation fluid so there are no substantial amount of droplets larger than about 30 nm in said substance in said cryopreservation fluid.
80. A process to enhance the cryopreservation of biological cells as described in clause 67 or any other clause wherein said step of assembling a cellular collection containing a plurality of biological cell structures comprises a step selected from a group consisting of the steps of:
    assembling a cellular collection containing a plurality of blood cell structures, assembling a cellular collection containing a plurality of stem cell structures,
assembling a cellular collection containing a plurality of skin cells,
assembling a cellular collection containing a plurality of embryonic stem cells,
assembling a cellular collection containing a plurality of neural stem cells,
assembling a cellular collection containing a plurality of umbilical cord blood cells,
assembling a cellular collection containing a plurality of epithelial stem cells
assembling a cellular collection containing a plurality of cardiac stem cells
assembling a cellular collection containing a plurality of muscle stem cells
assembling a cellular collection containing a plurality of connective stem cells
assembling a cellular collection containing a plurality of epithelial cells
assembling a cellular collection containing a plurality of cardiac cells
assembling a cellular collection containing a plurality of muscle cells
assembling a cellular collection containing a plurality of connective cells
assembling a cellular collection containing a plurality of nerve cells
assembling a cellular collection containing a plurality of histological sample cells,
assembling a cellular collection containing a plurality of plant seed cells,
assembling a cellular collection containing a plurality of plant shoot cells,
assembling a cellular collection containing a plurality of ovarian tissue cell structures,
assembling a cellular collection containing a plurality of testicular tissue cell structures,
assembling a cellular collection containing a plurality of embryo cells,
assembling a cellular collection containing a plurality of tumorous tissue cell structures,
assembling a cellular collection containing a plurality of yeast cells,
assembling a cellular collection containing a plurality of bacterial cells,
assembling a cellular collection containing a plurality of algal cells,
assembling a cellular collection containing a plurality of fungal cells,
assembling a cellular collection containing a plurality of mesenchymal cells,
assembling a cellular collection containing a plurality of keratinocyte cells,
assembling a cellular collection containing a plurality of melanocyte cells,
assembling a cellular collection containing a plurality of hepatocyte cells,
assembling a cellular collection containing a plurality of oocyte cells, and
assembling a cellular collection containing a plurality of sperm cells.

81. A process to enhance the cryopreservation of biological cells as described in clause 79 wherein the step of assembling a cellular collection containing a plurality of biological cell structures comprises a step selected from a group consisting of the steps of:

assembling a cellular collection containing a plurality of blood cell structures,
assembling a cellular collection containing a plurality of stem cell structures,
assembling a cellular collection containing a plurality of skin cells,
assembling a cellular collection containing a plurality of embryonic stem cells,
assembling a cellular collection containing a plurality of neural stem cells,
assembling a cellular collection containing a plurality of umbilical cord blood cells,
assembling a cellular collection containing a plurality of epithelial stem cells
assembling a cellular collection containing a plurality of cardiac stem cells
assembling a cellular collection containing a plurality of muscle stem cells
assembling a cellular collection containing a plurality of connective stem cells
assembling a cellular collection containing a plurality of epithelial cells
assembling a cellular collection containing a plurality of cardiac cells
assembling a cellular collection containing a plurality of muscle cells
assembling a cellular collection containing a plurality of connective cells
assembling a cellular collection containing a plurality of nerve cells
assembling a cellular collection containing a plurality of histological sample cells,
assembling a cellular collection containing a plurality of plant seed cells,
assembling a cellular collection containing a plurality of plant shoot cells,
assembling a cellular collection containing a plurality of ovarian tissue cell structures,
assembling a cellular collection containing a plurality of testicular tissue cell structures,
assembling a cellular collection containing a plurality of embryo cells,
assembling a cellular collection containing a plurality of tumorous tissue cell structures,
assembling a cellular collection containing a plurality of yeast cells,
assembling a cellular collection containing a plurality of bacterial cells,
assembling a cellular collection containing a plurality of algal cells,
assembling a cellular collection containing a plurality of fungal cells,
assembling a cellular collection containing a plurality of mesenchymal cells,
assembling a cellular collection containing a plurality of keratinocyte cells,
assembling a cellular collection containing a plurality of melanocyte cells,
assembling a cellular collection containing a plurality of hepatocyte cells,
assembling a cellular collection containing a plurality of oocyte cells, and
assembling a cellular collection containing a plurality of sperm cells.

82. A process to enhance the cryopreservation of biological cells comprising the steps of:

assembling a cellular collection containing a plurality of biological cell structures;

establishing a cryopreservation fluid to be incorporated with said biological cell structures in cryopreservation;

sizing droplets of at least one substance within said cryopreservation fluid;

mixing said cryopreservation fluid and said biological cell structures to form a fluidic cryopreservation composite;

removing thermal energy from said fluidic cryopreservation composite;

freezing said fluidic cryopreservation composite by reducing the temperature of said fluidic cryopreservation composite below the freezing point of water; and providing an enhanced post-cryogenic viability for said biological cell structures.

83. A process to enhance the cryopreservation of biological cells as described in clause 82 or any other clause wherein said step of sizing droplets of at least one substance within said cryopreservation fluid comprises the step of rending at least some drops of at least one substance in said cryopreservation fluid.

84. A process to enhance the cryopreservation of biological cells as described in clause 83 or any other clause wherein said step of sizing droplets of at least one substance within said cryopreservation fluid comprises the step of rending at least some lipid drops of at least one substance in said cryopreservation fluid.

85. A process to enhance the cryopreservation of biological cells as described in clause 82 or any other clause wherein said step of sizing droplets of at least one substance within said cryopreservation fluid comprises a step selected from a group consisting of the steps of:

creating a substance in said cryopreservation fluid with droplets numbering at least about 30 times the number of initial drops of said substance in said cryopreservation fluid, creating a substance in said cryopreservation fluid with droplets numbering at least about 50 times the number of initial drops of said substance in said cryopreservation fluid, creating a substance in said cryopreservation fluid with droplets numbering at least about 100 times the number of initial drops of said substance in said cryopreservation fluid, creating a substance in said cryopreservation fluid with droplets numbering at least about 500 times the number of initial drops of said substance in said cryopreservation fluid, creating a substance in said cryopreservation fluid with droplets numbering at least about 1000 times the number of initial drops of said substance in said cryopreservation fluid, creating a substance in said cryopreservation fluid with droplets numbering at least about 5000 times the number of initial drops of said substance in said cryopreservation fluid, creating a substance in said cryopreservation fluid with droplets numbering at least about 10000 times the number of initial drops of said substance in said cryopreservation fluid, creating a substance in said cryopreservation fluid with droplets numbering at least about 50000 times the number of initial drops of said substance in said cryopreservation fluid, and creating a substance in said cryopreservation fluid with droplets numbering at least about 100000 times the number of initial drops of said substance in said cryopreservation fluid.

86. A process to enhance the cryopreservation of biological cells as described in clause 82 or any other clause wherein said step of sizing droplets of at least one substance within said cryopreservation fluid comprises the step of creating a substantial number of relatively small droplets in a substance contained within said cryopreservation fluid.

87. A process to enhance the cryopreservation of biological cells as described in clause 82 or any other clause wherein said step of sizing droplets of at least one substance within said cryopreservation fluid comprises the step of in situ creating a substantial number of relatively small droplets in a substance contained within said cryopreservation fluid.

88. A process to enhance the cryopreservation of biological cells as described in clause 86 or any other clause wherein said step creating of a substantial number of relatively small droplets in a substance contained within said cryopreservation fluid comprises the step of rending larger drops of a substance in said cryopreservation fluid to form smaller droplets of said substance in said cryopreservation fluid.

89. A process to enhance the cryopreservation of biological cells as described in clause 85, 86, 87, or 88 or any other clause wherein said step of sizing droplets of at least one substance within said cryopreservation fluid comprises a step selected from a group consisting of the steps of:

creating a substantial number of droplets of a substance contained within said cryopreservation fluid with no substantial amount of droplets larger than at least about 1000 nm, creating a substantial number of droplets of a substance contained within said cryopreservation fluid with no substantial amount of droplets larger than at least about 900 nm, creating a substantial number of droplets of a substance contained within said cryopreservation fluid with no substantial amount of droplets larger than at least about 700 nm, creating a substantial number of droplets of a substance contained within said cryopreservation fluid with no substantial amount of droplets larger than at least about 500 nm, creating a substantial number of droplets of a substance contained within said cryopreservation fluid with no substantial amount of droplets larger than at least about 300 nm, creating a substantial number of droplets of a substance contained within said cryopreservation fluid with no substantial amount of droplets larger than at least about 100 nm, creating a substantial number of droplets of a substance contained within said cryopreservation fluid with no substantial amount of droplets larger than at least about 70 nm, creating a substantial number of droplets of a substance contained within said cryopreservation fluid with no substantial amount of droplets larger than at least about 50 nm, and creating a substantial number of droplets of a substance contained within said cryopreservation fluid with no substantial amount of droplets larger than at least about 30 nm.

90. A process to enhance the cryopreservation of biological cells as described in clause 89 or any other clause said step of sizing droplets of at least one substance within said cryopreservation fluid comprises a step selected from a group consisting of the steps of:
creating said substance in said cryopreservation fluid so that at least about 20% of said droplets of said substance in said cryopreservation fluid are droplets at least about as small as said desired size,
creating said substance in said cryopreservation fluid so that at least about 40% of said droplets of said substance in said cryopreservation fluid are droplets at least about as small as said desired size,
creating said substance in said cryopreservation fluid so that at least about 60% of said droplets of said substance in said cryopreservation fluid are droplets at least about as small as said desired size,
creating said substance in said cryopreservation fluid so that at least about 80% of said droplets of said substance in said cryopreservation fluid are droplets at least about as small as said desired size, and
creating said substance in said cryopreservation fluid so that at least about 90% of said droplets of said substance in said cryopreservation fluid are droplets at least about as small as said desired size.

91. A process to enhance the cryopreservation of biological cells as described in clause 86, 87, or 88 or any other clause wherein said step of sizing droplets of at least one substance contained within said cryopreservation fluid comprises a step selected from a group consisting of the steps of:
creating a substance in said cryopreservation fluid with droplets numbering at least about 30 times the number of initial drops of said substance in said cryopreservation fluid,
creating a substance in said cryopreservation fluid with droplets numbering at least about 50 times the number of initial drops of said substance in said cryopreservation fluid,
creating a substance in said cryopreservation fluid with droplets numbering at least about 100 times the number of initial drops of said substance in said cryopreservation fluid,
creating a substance in said cryopreservation fluid with droplets numbering at least about 500 times the number of initial drops of said substance in said cryopreservation fluid,
creating a substance in said cryopreservation fluid with droplets numbering at least about 1000 times the number of initial drops of said substance in said cryopreservation fluid,
creating a substance in said cryopreservation fluid with droplets numbering at least about 5000 times the number of initial drops of said substance in said cryopreservation fluid,
creating a substance in said cryopreservation fluid with droplets numbering at least about 10000 times the number of initial drops of said substance in said cryopreservation fluid,
creating a substance in said cryopreservation fluid with droplets numbering at least about 50000 times the number of initial drops of said substance in said cryopreservation fluid, and
creating a substance in said cryopreservation fluid with droplets numbering at least about 100000 times the number of initial drops of said substance in said cryopreservation fluid.

92. A process to enhance the cryopreservation of biological cells as described in clause 82, 85, 88 or any other clause wherein said step of assembling a cellular collection containing a plurality of biological cell structures comprises a step selected from a group consisting of the steps of:
assembling a cellular collection containing a plurality of blood cell structures,
assembling a cellular collection containing a plurality of stem cell structures,
assembling a cellular collection containing a plurality of skin cells,
assembling a cellular collection containing a plurality of embryonic stem cells,
assembling a cellular collection containing a plurality of neural stem cells,
assembling a cellular collection containing a plurality of umbilical cord blood cells,
assembling a cellular collection containing a plurality of epithelial stem cells
assembling a cellular collection containing a plurality of cardiac stem cells
assembling a cellular collection containing a plurality of muscle stem cells
assembling a cellular collection containing a plurality of connective stem cells
assembling a cellular collection containing a plurality of epithelial cells
assembling a cellular collection containing a plurality of cardiac cells
assembling a cellular collection containing a plurality of muscle cells
assembling a cellular collection containing a plurality of connective cells
assembling a cellular collection containing a plurality of nerve cells
assembling a cellular collection containing a plurality of histological sample cells,
assembling a cellular collection containing a plurality of plant seed cells,
assembling a cellular collection containing a plurality of plant shoot cells,
assembling a cellular collection containing a plurality of ovarian tissue cell structures,
assembling a cellular collection containing a plurality of testicular tissue cell structures,
assembling a cellular collection containing a plurality of embryo cells,
assembling a cellular collection containing a plurality of tumorous tissue cell structures,
assembling a cellular collection containing a plurality of yeast cells,
assembling a cellular collection containing a plurality of bacterial cells,
assembling a cellular collection containing a plurality of algal cells,
assembling a cellular collection containing a plurality of fungal cells,
assembling a cellular collection containing a plurality of mesenchymal cells,
assembling a cellular collection containing a plurality of keratinocyte cells,
assembling a cellular collection containing a plurality of melanocyte cells,
assembling a cellular collection containing a plurality of hepatocyte cells, assembling a cellular collection containing a plurality of oocyte cells, and
assembling a cellular collection containing a plurality of sperm cells.

93. A process to enhance the cryopreservation of biological cells as described in clause 82 or any other clause wherein said step of sizing droplets of at least one substance within said cryopreservation fluid comprises the step of creating a substantially uniform maximum droplet size of a substance contained within said cryopreservation fluid.

94. A process to enhance the cryopreservation of biological cells as described in clause 93 or any other clause wherein said step of creating a substantially uniform maximum droplet size of a substance contained within said cryopreservation fluid comprises the step selected from a group consisting of:
  causing a substance contained within said cryopreservation fluid to have no substantial number of droplets larger than at least about 1000 nm,
  causing a substance contained within said cryopreservation fluid to have no substantial number of droplets larger than at least about 900 nm,
  causing a substance contained within said cryopreservation fluid to have no substantial number of droplets larger than at least about 700 nm,
  causing a substance contained within said cryopreservation fluid to have no substantial number of droplets larger than at least about 500 nm,
  causing a substance contained within said cryopreservation fluid to have no substantial number of droplets larger than at least about 300 nm,
  causing a substance contained within said cryopreservation fluid to have no substantial number of droplets larger than at least about 100 nm,
  causing a substance contained within said cryopreservation fluid to have no substantial number of droplets larger than at least about 70 nm,
  causing a substance contained within said cryopreservation fluid to have no substantial number of droplets larger than at least about 50 nm, and
  causing a substance contained within said cryopreservation fluid to have no substantial number of droplets larger than at least about 30 nm.

95. A process to enhance the cryopreservation of biological cells as described in clause 93 or any other clause wherein said step of creating a substantially uniform maximum droplet size of a substance contained within said cryopreservation fluid comprises a step selected from a group consisting of the steps of:
  establishing droplets of a substance contained within said cryopreservation fluid so there is no substantial amount of droplets larger than at least about 1000 nm,
  establishing droplets of a substance contained within said cryopreservation fluid so there is no substantial amount of droplets larger than at least about 900 nm,
  establishing droplets of a substance contained within said cryopreservation fluid so there is no substantial amount of droplets larger than at least about 700 nm,
  establishing droplets of a substance contained within said cryopreservation fluid so there is no substantial amount of droplets larger than at least about 500 nm,
  establishing droplets of a substance contained within said cryopreservation fluid so there is no substantial amount of droplets larger than at least about 300 nm,
  establishing droplets of a substance contained within said cryopreservation fluid so there is no substantial amount of droplets larger than at least about 100 nm,
  establishing droplets of a substance contained within said cryopreservation fluid so there is no substantial amount of droplets larger than at least about 70 nm,
  establishing droplets of a substance contained within said cryopreservation fluid so there is no substantial amount of droplets larger than at least about 50 nm, and
  establishing droplets of a substance contained within said cryopreservation fluid so there is no substantial amount of droplets larger than at least about 30 nm.

96. A process to enhance the cryopreservation of biological cells as described in clause 82 or any other clause wherein said step of sizing droplets of at least one substance within said cryopreservation fluid comprises the step of causing a substance contained within said cryopreservation fluid to have a droplet size with a skewed size distribution that favors smaller size droplets.

97. A process to enhance the cryopreservation of biological cells as described in clause 96 or any other clause wherein the step of causing a substance contained within said cryopreservation fluid having a droplet size with a skewed size distribution that favors smaller size droplets a step selected from a group consisting of the steps of:
  modifying a substance contained within said cryopreservation fluid to have a mode drop size of less than at least about 1000 nm,
  modifying a substance contained within said cryopreservation fluid to have a mode drop size of less than at least about 900 nm,
  modifying a substance contained within said cryopreservation fluid to have a mode drop size of less than at least about 700 nm,
  modifying a substance contained within said cryopreservation fluid to have a mode drop size of less than at least about 500 nm,
  modifying a substance contained within said cryopreservation fluid to have a mode drop size of less than at least about 300 nm,
  modifying a substance contained within said cryopreservation fluid to have a mode drop size of less than at least about 100 nm,
  modifying a substance contained within said cryopreservation fluid to have a mode drop size of less than at least about 70 nm,
  modifying a substance contained within said cryopreservation fluid to have a mode drop size of less than at least about 50 nm, and
  modifying a substance contained within said cryopreservation fluid to have a mode drop size of less than at least about 30 nm.

98. A process to enhance the cryopreservation of biological cells as described in clause 82 or any other clause wherein said step of sizing droplets of at least one substance within said cryopreservation fluid comprises the step of eliminating droplets from said cryopreservation fluid.

99. A process to enhance the cryopreservation of biological cells as described in clause 98 or any other clause wherein said step of eliminating droplets from said cryopreservation fluid comprises the step of size eliminating droplets from said cryopreservation fluid.

100. A process to enhance the cryopreservation of biological cells as described in clause 99 or any other clause wherein said step of size eliminating droplets from said cryopreservation fluid comprises the step of size eliminating at least some lipid droplets of said cryopreservation fluid.

101. A process to enhance the cryopreservation of biological cells as described in clause 100 or any other clause wherein said step of eliminating at least some lipid droplets of said cryopreservation fluid comprises a step selected from a group consisting of the steps of:
  eliminating droplets of a lipid contained within said cryopreservation fluid so there is no substantial amount of droplets larger than at least about 1000 nm,
  eliminating droplets of a lipid contained within said cryopreservation fluid so there is no substantial amount of droplets larger than at least about 900 nm,
  eliminating droplets of a lipid contained within said cryopreservation fluid so there is no substantial amount of droplets larger than at least about 700 nm,
  eliminating droplets of a lipid contained within said cryopreservation fluid so there is no substantial amount of droplets larger than at least about 500 nm,
  eliminating droplets of a lipid contained within said cryopreservation fluid so there is no substantial amount of droplets larger than at least about 300 nm,
  eliminating droplets of a lipid contained within said cryopreservation fluid so there is no substantial amount of droplets larger than at least about 100 nm,
  eliminating droplets of a lipid contained within said cryopreservation fluid so there is no substantial amount of droplets larger than at least about 70 nm,
  eliminating droplets of a lipid contained within said cryopreservation fluid so there is no substantial amount of droplets larger than at least about 50 nm, and
  eliminating droplets of a lipid contained within said cryopreservation fluid so there is no substantial amount of droplets larger than at least about 30 nm.

102. A process to enhance the cryopreservation of biological cells comprising the steps of:
  assembling a cellular collection containing a plurality of biological cell structures;
  establishing a cryopreservation fluid to be incorporated with said biological cell structures in cryopreservation;
  in situ sizing droplets of at least one substance within said cryopreservation fluid;
  mixing said cryopreservation fluid and said biological cell structures to form a fluidic cryopreservation composite;
  removing thermal energy from said fluidic cryopreservation composite; and
  freezing said fluidic cryopreservation composite by reducing the temperature of said fluidic cryopreservation composite below the freezing point of water.

103. A process to enhance the cryopreservation of biological cells as described in clause 102 or any other clause wherein said step of in situ sizing droplets of at least one substance within said cryopreservation fluid comprises the step of in situ rending at least some drops of at least one substance in said cryopreservation fluid 104. A process to enhance the cryopreservation of biological cells as described in clause 103 or any other clause wherein said step of in situ sizing droplets of at least one substance within said cryopreservation fluid comprises the step of in situ rending at least some lipid drops of at least one substance in said cryopreservation fluid.

105. A process to enhance the cryopreservation of biological cells as described in clause 102 or any other clause wherein said step of in situ sizing droplets of at least one substance within said cryopreservation fluid comprises a step selected from a group consisting of the steps of:
  in situ creating a substance in said cryopreservation fluid with droplets numbering at least about 30 times the number of initial drops of said substance in said cryopreservation fluid,
  in situ creating a substance in said cryopreservation fluid with droplets numbering at least about 50 times the number of initial drops of said substance in said cryopreservation fluid,
  in situ creating a substance in said cryopreservation fluid with droplets numbering at least about 100 times the number of initial drops of said substance in said cryopreservation fluid,
  in situ creating a substance in said cryopreservation fluid with droplets numbering at least about 500 times the number of initial drops of said substance in said cryopreservation fluid,
  in situ creating a substance in said cryopreservation fluid with droplets numbering at least about 1000 times the number of initial drops of said substance in said cryopreservation fluid,
  in situ creating a substance in said cryopreservation fluid with droplets numbering at least about 5000 times the number of initial drops of said substance in said cryopreservation fluid,
  in situ creating a substance in said cryopreservation fluid with droplets numbering at least about 10000 times the number of initial drops of said substance in said cryopreservation fluid,
  in situ creating a substance in said cryopreservation fluid with droplets numbering at least about 50000 times the number of initial drops of said substance in said cryopreservation fluid, and
  in situ creating a substance in said cryopreservation fluid with droplets numbering at least about 100000 times the number of initial drops of said substance in said cryopreservation fluid.

106. A process to enhance the cryopreservation of biological cells as described in clause 102 or any other clause wherein said step of in situ sizing droplets of at least one substance within said cryopreservation fluid comprises the step of in situ creating a substantial number of relatively small droplets in a substance contained within said cryopreservation fluid.

107. A process to enhance the cryopreservation of biological cells as described in clause 106 or any other clause wherein said step in situ creating of a substantial number of relatively small droplets in a substance contained within said cryopreservation fluid comprises the step of in situ rending larger drops of a substance in said cryopreservation fluid to form smaller droplets of said substance in said cryopreservation fluid.

108. A process to enhance the cryopreservation of biological cells as described in clause 129, 106, or 107 or any other clause wherein said step of in situ sizing droplets of at least one substance within said cryopreservation fluid comprises a step selected from a group consisting of the steps of:
  in situ creating a substantial number of droplets of a substance contained within said cryopreservation fluid with no substantial amount of droplets larger than at least about 1000 nm,
  in situ creating a substantial number of droplets of a substance contained within said cryopreservation fluid with no substantial amount of droplets larger than at least about 900 nm,
  in situ creating a substantial number of droplets of a substance contained within said cryopreservation fluid with no substantial amount of droplets larger than at least about 700 nm, in situ creating a substantial number of droplets of a substance contained within said cryopreservation fluid with no substantial amount of droplets larger than at least about 500 nm, in situ creating a substantial number of droplets of a substance contained within said cryopreservation fluid with no substantial amount of droplets larger than at least about 300 nm, in situ creating a substantial number of droplets of a substance contained within said cryopreservation fluid with no substantial amount of droplets larger than at least about 100 nm, in situ creating a substantial number of droplets of a substance contained within said cryopreservation fluid with no substantial amount of droplets larger than at least about 70 nm, in situ creating a substantial number of droplets of a substance contained within said cryopreservation fluid with no substantial amount of droplets larger than at least about 50 nm, and in situ creating a substantial number of droplets of a substance contained within said cryopreservation fluid with no substantial amount of droplets larger than at least about 30 nm.

109. A process to enhance the cryopreservation of biological cells as described in clause 108 or any other clause said step of in situ sizing droplets of at least one substance within said cryopreservation fluid comprises a step selected from a group consisting of the steps of:

in situ creating said substance in said cryopreservation fluid so that at least about 20% of said droplets of said substance in said cryopreservation fluid are droplets at least about as small as said desired size, in situ creating said substance in said cryopreservation fluid so that at least about 40% of said droplets of said substance in said cryopreservation fluid are droplets at least about as small as said desired size, in situ creating said substance in said cryopreservation fluid so that at least about 60% of said droplets of said substance in said cryopreservation fluid are droplets at least about as small as said desired size, in situ creating said substance in said cryopreservation fluid so that at least about 80% of said droplets of said substance in said cryopreservation fluid are droplets at least about as small as said desired size, and in situ creating said substance in said cryopreservation fluid so that at least about 90% of said droplets of said substance in said cryopreservation fluid are droplets at least about as small as said desired size.

110. A process to enhance the cryopreservation of biological cells as described in clause 106 or 107 or any other clause wherein said step of in situ sizing droplets of at least one substance contained within said cryopreservation fluid comprises a step selected from a group consisting of the steps of:

in situ creating a substance in said cryopreservation fluid with droplets numbering at least about 30 times the number of initial drops of said substance in said cryopreservation fluid, in situ creating a substance in said cryopreservation fluid with droplets numbering at least about 50 times the number of initial drops of said substance in said cryopreservation fluid, in situ creating a substance in said cryopreservation fluid with droplets numbering at least about 100 times the number of initial drops of said substance in said cryopreservation fluid, in situ creating a substance in said cryopreservation fluid with droplets numbering at least about 500 times the number of initial drops of said substance in said cryopreservation fluid, in situ creating a substance in said cryopreservation fluid with droplets numbering at least about 1000 times the number of initial drops of said substance in said cryopreservation fluid, in situ creating a substance in said cryopreservation fluid with droplets numbering at least about 5000 times the number of initial drops of said substance in said cryopreservation fluid, in situ creating a substance in said cryopreservation fluid with droplets numbering at least about 10000 times the number of initial drops of said substance in said cryopreservation fluid, in situ creating a substance in said cryopreservation fluid with droplets numbering at least about 50000 times the number of initial drops of said substance in said cryopreservation fluid, and in situ creating a substance in said cryopreservation fluid with droplets numbering at least about 100000 times the number of initial drops of said substance in said cryopreservation fluid.

111. A process to enhance the cryopreservation of biological cells as described in clause 102, 105, or 107 or any other clause wherein said step of assembling a cellular collection containing a plurality of biological cell structures comprises a step selected from a group consisting of the steps of:

assembling a cellular collection containing a plurality of blood cell structures, assembling a cellular collection containing a plurality of stem cell structures, assembling a cellular collection containing a plurality of skin cells, assembling a cellular collection containing a plurality of embryonic stem cells, assembling a cellular collection containing a plurality of neural stem cells, assembling a cellular collection containing a plurality of umbilical cord blood cells, assembling a cellular collection containing a plurality of epithelial stem cells assembling a cellular collection containing a plurality of cardiac stem cells assembling a cellular collection containing a plurality of muscle stem cells assembling a cellular collection containing a plurality of connective stem cells assembling a cellular collection containing a plurality of epithelial cells assembling a cellular collection containing a plurality of cardiac cells assembling a cellular collection containing a plurality of muscle cells assembling a cellular collection containing a plurality of connective cells assembling a cellular collection containing a plurality of nerve cells assembling a cellular collection containing a plurality of histological sample cells, assembling a cellular collection containing a plurality of plant seed cells, assembling a cellular collection containing a plurality of plant shoot cells, assembling a cellular collection containing a plurality of ovarian tissue cell structures,
assembling a cellular collection containing a plurality of testicular tissue cell structures,
assembling a cellular collection containing a plurality of embryo cells,
assembling a cellular collection containing a plurality of tumorous tissue cell structures,
assembling a cellular collection containing a plurality of yeast cells,
assembling a cellular collection containing a plurality of bacterial cells,
assembling a cellular collection containing a plurality of algal cells,
assembling a cellular collection containing a plurality of fungal cells,
assembling a cellular collection containing a plurality of mesenchymal cells,
assembling a cellular collection containing a plurality of keratinocyte cells,
assembling a cellular collection containing a plurality of melanocyte cells,
assembling a cellular collection containing a plurality of hepatocyte cells,
assembling a cellular collection containing a plurality of oocyte cells, and
assembling a cellular collection containing a plurality of sperm cells.

112. A process to enhance the cryopreservation of biological cells as described in clause 102 or any other clause wherein said step of in situ sizing droplets of at least one substance within said cryopreservation fluid comprises the step of creating a substantially uniform maximum droplet size of a substance contained within said cryopreservation fluid.

113. A process to enhance the cryopreservation of biological cells as described in clause 112 or any other clause wherein said step of in situ creating a substantially uniform maximum droplet size of a substance contained within said cryopreservation fluid comprises the step selected from a group consisting of:
in situ causing a substance contained within said cryopreservation fluid to have no substantial number of droplets larger than at least about 1000 nm,
in situ causing a substance contained within said cryopreservation fluid to have no substantial number of droplets larger than at least about 900 nm,
in situ causing a substance contained within said cryopreservation fluid to have no substantial number of droplets larger than at least about 700 nm,
in situ causing a substance contained within said cryopreservation fluid to have no substantial number of droplets larger than at least about 500 nm,
in situ causing a substance contained within said cryopreservation fluid to have no substantial number of droplets larger than at least about 300 nm,
in situ causing a substance contained within said cryopreservation fluid to have no substantial number of droplets larger than at least about 100 nm,
in situ causing a substance contained within said cryopreservation fluid to have no substantial number of droplets larger than at least about 70 nm,
in situ causing a substance contained within said cryopreservation fluid to have no substantial number of droplets larger than at least about 50 nm, and
in situ causing a substance contained within said cryopreservation fluid to have no substantial number of droplets larger than at least about 30 nm.

114. A process to enhance the cryopreservation of biological cells as described in clause 112 or any other clause wherein said step of in situ creating a substantially uniform maximum droplet size of a substance contained within said cryopreservation fluid comprises a step selected from a group consisting of the steps of:
in situ establishing droplets of a substance contained within said cryopreservation fluid so there is no substantial amount of droplets larger than at least about 1000 nm,
in situ establishing droplets of a substance contained within said cryopreservation fluid so there is no substantial amount of droplets larger than at least about 900 nm,
in situ establishing droplets of a substance contained within said cryopreservation fluid so there is no substantial amount of droplets larger than at least about 700 nm,
in situ establishing droplets of a substance contained within said cryopreservation fluid so there is no substantial amount of droplets larger than at least about 500 nm,
in situ establishing droplets of a substance contained within said cryopreservation fluid so there is no substantial amount of droplets larger than at least about 300 nm,
in situ establishing droplets of a substance contained within said cryopreservation fluid so there is no substantial amount of droplets larger than at least about 100 nm,
in situ establishing droplets of a substance contained within said cryopreservation fluid so there is no substantial amount of droplets larger than at least about 70 nm,
in situ establishing droplets of a substance contained within said cryopreservation fluid so there is no substantial amount of droplets larger than at least about 50 nm, and
in situ establishing droplets of a substance contained within said cryopreservation fluid so there is no substantial amount of droplets larger than at least about 30 nm.

115. A process to enhance the cryopreservation of biological cells as described in clause 102 or any other clause wherein said step of in situ sizing droplets of at least one substance within said cryopreservation fluid comprises the step of in situ causing a substance contained within said cryopreservation fluid to have a droplet size with a skewed size distribution that favors smaller size droplets.

116. A process to enhance the cryopreservation of biological cells as described in clause 115 or any other clause wherein the step of in situ causing a substance contained within said cryopreservation fluid having a droplet size with a skewed size distribution that favors smaller size droplets a step selected from a group consisting of the steps of:
in situ modifying a substance contained within said cryopreservation fluid to have a mode drop size of less than at least about 1000 nm,
in situ modifying a substance contained within said cryopreservation fluid to have a mode drop size of less than at least about 900 nm, in situ modifying a substance contained within said cryopreservation fluid to have a mode drop size of less than at least about 700 nm,
in situ modifying a substance contained within said cryopreservation fluid to have a mode drop size of less than at least about 500 nm,
in situ modifying a substance contained within said cryopreservation fluid to have a mode drop size of less than at least about 300 nm,
in situ modifying a substance contained within said cryopreservation fluid to have a mode drop size of less than at least about 100 nm,
in situ modifying a substance contained within said cryopreservation fluid to have a mode drop size of less than at least about 70 nm,
in situ modifying a substance contained within said cryopreservation fluid to have a mode drop size of less than at least about 50 nm, and
in situ modifying a substance contained within said cryopreservation fluid to have a mode drop size of less than at least about 30 nm.

117. A process to enhance the cryopreservation of biological cells as described in clause 102 or any other clause wherein said step of in situ sizing droplets of at least one substance within said cryopreservation fluid comprises the step of in situ eliminating droplets from said cryopreservation fluid.

118. A process to enhance the cryopreservation of biological cells as described in clause 117 or any other clause wherein said step of in situ eliminating droplets from said cryopreservation fluid comprises the step of in situ size eliminating droplets from said cryopreservation fluid.

119. A process to enhance the cryopreservation of biological cells as described in clause 118 or any other clause wherein said step of in situ size eliminating droplets from said cryopreservation fluid comprises the step of in situ size eliminating at least some lipid droplets of said cryopreservation fluid.

120. A process to enhance the cryopreservation of biological cells as described in clause 119 or any other clause wherein said step of in situ eliminating at least some lipid droplets of said cryopreservation fluid comprises a step selected from a group consisting of the steps of:
in situ eliminating droplets of a lipid contained within said cryopreservation fluid so there is no substantial amount of droplets larger than at least about 1000 nm,
in situ eliminating droplets of a lipid contained within said cryopreservation fluid so there is no substantial amount of droplets larger than at least about 900 nm,
in situ eliminating droplets of a lipid contained within said cryopreservation fluid so there is no substantial amount of droplets larger than at least about 700 nm,
in situ eliminating droplets of a lipid contained within said cryopreservation fluid so there is no substantial amount of droplets larger than at least about 500 nm,
in situ eliminating droplets of a lipid contained within said cryopreservation fluid so there is no substantial amount of droplets larger than at least about 300 nm,
in situ eliminating droplets of a lipid contained within said cryopreservation fluid so there is no substantial amount of droplets larger than at least about 100 nm,
in situ eliminating droplets of a lipid contained within said cryopreservation fluid so there is no substantial amount of droplets larger than at least about 70 nm,
in situ eliminating droplets of a lipid contained within said cryopreservation fluid so there is no substantial amount of droplets larger than at least about 50 nm, and
in situ eliminating droplets of a lipid contained within said cryopreservation fluid so there is no substantial amount of droplets larger than at least about 30 nm.

121. A cryopreservation composition comprising:
an assemblage of biological cell structures; and
an increased surface energy content cryopreservation fluid mixed with said biological cell structures.

122. A cryopreservation composition as described in clause 121 or any other clause wherein said increased surface energy content cryopreservation fluid comprises an increased surface energy content cryopreservation fluid that has been frozen at temperature below the freezing point of water.

123. A cryopreservation composition as described in clause 122 or any other clause wherein said increased surface energy content cryopreservation fluid comprises an increased surface energy content cryopreservation fluid that has been thawed by increasing its temperature above the freezing point of water.

124. A cryopreservation composition as described in clause 122 or 123 or any other clause wherein said assemblage of biological cell structures comprises an enhanced post-cryogenic viability assemblage of biological cell structures.

125. A cryopreservation composition as described in clause 124 or any other clause wherein said enhanced post-cryogenic viability assemblage of biological cell structures comprises a relatively high post-cryogenic viability assemblage of biological cell structures.

126. A cryopreservation composition as described in clause 125 or any other clause wherein said relatively high post-cryogenic viability assemblage of biological cell structures comprises an assemblage of biological cell structures selected from a group consisting of:
an at least about 5% higher post-cryogenic viability assemblage of biological cell structures over traditional post-cryogenic cell structures of a similar character and thermal treatment,
an at least about 10% higher post-cryogenic viability assemblage of biological cell structures over traditional post-cryogenic cell structures of a similar character and thermal treatment,
an at least about 15% higher post-cryogenic viability assemblage of biological cell structures over traditional post-cryogenic cell structures of a similar character and thermal treatment,
an at least about 20% higher post-cryogenic viability assemblage of biological cell structures over traditional post-cryogenic cell structures of a similar character and thermal treatment, and
an at least about 25% higher post-cryogenic viability assemblage of biological cell structures over traditional post-cryogenic cell structures of a similar character and thermal treatment.

127. A cryopreservation composition as described in clause 125 or any other clause wherein said relatively high post-cryogenic viability assemblage of biological cell structures comprises an assemblage of biological cell structures selected from a group consisting of:
an assemblage of biological cell structures having not less than about 80% of the pre-cryogenic viability for said biological cell structures,
an assemblage of biological cell structures having not less than about 70% of the pre-cryogenic viability for said biological cell structures, an assemblage of biological cell structures having not less than about 60% of the pre-cryogenic viability for said biological cell structures,
an assemblage of biological cell structures having not less than about 50% of the pre-cryogenic viability for said biological cell structures,
an assemblage of biological cell structures having not less than about 40% of the pre-cryogenic viability for said biological cell structures,
an assemblage of biological cell structures having not less than about 30% of the pre-cryogenic viability for said biological cell structures, and
an assemblage of biological cell structures having not less than about 20% of the pre-cryogenic viability for said biological cell structures.

128. A cryopreservation composition as described in clause 121 or any other clause wherein said increased surface energy content cryopreservation fluid comprises a substantially increased surface energy cryopreservation fluid.

129. A cryopreservation composition as described in clause 128 or any other clause wherein said substantially increased surface energy cryopreservation fluid comprises a substantially increased surface energy cryopreservation fluid selected from a group consisting of:
a cryopreservation fluid containing a substance having its surface energy increased by at least about 100 j/kg surface energy,
a cryopreservation fluid containing a substance having its surface energy increased by at least about 270 j/kg surface energy,
a cryopreservation fluid containing a substance having its surface energy increased by at least about 320 j/kg surface energy,
a cryopreservation fluid containing a substance having its surface energy increased by at least about 650 j/kg surface energy,
a cryopreservation fluid containing a substance having its surface energy increased by at least about 1050 j/kg surface energy,
a cryopreservation fluid containing a substance having its surface energy increased by at least about 3600 j/kg surface energy, and
a cryopreservation fluid containing a substance having its surface energy increased by at least about 5200 j/kg surface energy.

130. A cryopreservation composition as described in clause 128 or any other clause wherein said substantially increased surface energy cryopreservation fluid comprises a substantially increased surface energy cryopreservation fluid selected from a group consisting of:
a cryopreservation fluid having a surface energy of a substance in said cryopreservation fluid increased to at least about 200 j/kg surface energy,
a cryopreservation fluid having a surface energy of a substance in said cryopreservation fluid increased to at least about 420 j/kg surface energy,
a cryopreservation fluid having a surface energy of a substance in said cryopreservation fluid increased to at least about 760 j/kg surface energy,
a cryopreservation fluid having a surface energy of a substance in said cryopreservation fluid increased to at least about 1200 j/kg surface energy,
a cryopreservation fluid having a surface energy of a substance in said cryopreservation fluid increased to at least about 3800 j/kg surface energy, and
a cryopreservation fluid having a surface energy of a substance in said cryopreservation fluid increased to at least about 5400 j/kg surface energy.

131. A cryopreservation composition as described in clause 128 or any other clause wherein said substantially increased surface energy cryopreservation fluid comprises a substantially increased surface energy cryopreservation fluid selected from a group consisting of:
a cryopreservation fluid containing a substance having its surface energy increased by at least about 30%,
a cryopreservation fluid containing a substance having its surface energy increased by at least about 50%,
a cryopreservation fluid containing a substance having its surface energy increased by at least about 100%,
a cryopreservation fluid containing a substance having its surface energy increased by at least about 3 times,
a cryopreservation fluid containing a substance having its surface energy increased by at least about 5 times,
a cryopreservation fluid containing a substance having its surface energy increased by at least about 10 times,
a cryopreservation fluid containing a substance having its surface energy increased by at least about 30 times, and
a cryopreservation fluid containing a substance having its surface energy increased by at least about 50 times.

132. A cryopreservation composition as described in clause 121, 101.1, 130, or 131 or any other clause wherein said increased surface energy content cryopreservation fluid comprises a structurally altered cryopreservation fluid.

133. A cryopreservation composition as described in clause 132 or any other clause wherein said structurally altered cryopreservation fluid comprises an increased structurally stored energy cryopreservation fluid.

134. A cryopreservation composition as described in clause 132 or any other clause wherein said structurally altered cryopreservation fluid comprises a drop transformed cryopreservation fluid.

135. A cryopreservation composition as described in clause 134 or any other clause wherein said drop transformed cryopreservation fluid comprises a drop transformed cryopreservation fluid selected from a group consisting of:
a cryopreservation fluid containing a substance having its number of drops in said cryopreservation fluid increased by at least about 30 times,
a cryopreservation fluid containing a substance having its number of drops in said cryopreservation fluid increased by at least about 50 times,
a cryopreservation fluid containing a substance having its number of drops in said cryopreservation fluid increased by at least about 100 times,
a cryopreservation fluid containing a substance having its number of drops in said cryopreservation fluid increased by at least about 500 times,
a cryopreservation fluid containing a substance having its number of drops in said cryopreservation fluid increased by at least about 1000 times,
a cryopreservation fluid containing a substance having its number of drops in said cryopreservation fluid increased by at least about 5000 times,
a cryopreservation fluid containing a substance having its number of drops in said cryopreservation fluid increased by at least about 10000 times,
a cryopreservation fluid containing a substance having its number of drops in said cryopreservation fluid increased by at least about 50000 times, and a cryopreservation fluid containing a substance having its number of drops in said cryopreservation fluid increased by at least about 100000 times.

136. A cryopreservation composition as described in clause 128 or any other clause wherein said increased surface energy content cryopreservation fluid comprises a larger drop rended cryopreservation fluid.

137. A cryopreservation composition as described in clause 136 or any other clause wherein said larger drop rended cryopreservation fluid comprises a larger drop rended cryopreservation fluid selected from a group consisting of:
a cryopreservation fluid containing a substance having no substantial number of droplets with a diameter larger than about 1000 nm,
a cryopreservation fluid containing a substance having no substantial number of droplets with a diameter larger than about 900 nm,
a cryopreservation fluid containing a substance having no substantial number of droplets with a diameter larger than about 700 nm,
a cryopreservation fluid containing a substance having no substantial number of droplets with a diameter larger than about 500 nm,
a cryopreservation fluid containing a substance having no substantial number of droplets with a diameter larger than about 300 nm,
a cryopreservation fluid containing a substance having no substantial number of droplets with a diameter larger than about 100 nm,
a cryopreservation fluid containing a substance having no substantial number of droplets with a diameter larger than about 70 nm,
a cryopreservation fluid containing a substance having no substantial number of droplets with a diameter larger than about 50 nm, and
a cryopreservation fluid containing a substance having no substantial number of droplets with a diameter larger than about 30 nm.

138. A cryopreservation composition as described in clause 137 or any other clause wherein said larger drop rended cryopreservation fluid comprises a larger drop rended cryopreservation fluid selected from a group consisting of:
a cryopreservation fluid containing a substance having at least about 20% of said droplets of said substance in said cryopreservation fluid at least about as small as said desired size,
a cryopreservation fluid containing a substance having at least about 40% of said droplets of said substance in said cryopreservation fluid at least about as small as said desired size,
a cryopreservation fluid containing a substance having at least about 60% of said droplets of said substance in said cryopreservation fluid at least about as small as said desired size,
a cryopreservation fluid containing a substance having at least about 80% of said droplets of said substance in said cryopreservation fluid at least about as small as said desired size, and
a cryopreservation fluid containing a substance having at least about 90% of said droplets of said substance in said cryopreservation fluid at least about as small as said desired size.

139. A cryopreservation composition as described in clause 121, 128, 129, 130, 131, 137, or 138 or any other clause wherein said increased surface energy content cryopreservation fluid comprises a lipid containing cryoprotective fluid selected from a group consisting of:
a sea buckthorn lipid containing cryoprotective fluid incorporated with said biological cell structures,
an unsaturated fatty acid containing cryoprotective fluid with said biological cell structures
a saturated fatty acid containing cryoprotective fluid with said biological cell structures
a palmitic acid containing cryoprotective fluid incorporated with said biological cell structures,
a palmitoleic acid containing cryoprotective fluid incorporated with said biological cell structures,
an oleic acid containing cryoprotective fluid incorporated with said biological cell structures,
a linoleic acid containing cryoprotective fluid incorporated with said biological cell structures,
a linolenic acid containing cryoprotective fluid incorporated with said biological cell structures,
a lecithin containing cryoprotective fluid incorporated with said biological cell structures,
a β-sitosterol containing cryoprotective fluid incorporated with said biological cell structures,
a β-amyrin containing cryoprotective fluid incorporated with said biological cell structures,
a γ-carotene containing cryoprotective fluid incorporated with said biological cell structures,
an α-amyrin containing cryoprotective fluid incorporated with said biological cell structures,
a β-carotene containing cryoprotective fluid incorporated with said biological cell structures,
a lycopene containing cryoprotective fluid incorporated with said biological cell structures,
a lutein containing cryoprotective fluid incorporated with said biological cell structures,
a tocopherol containing cryoprotective fluid incorporated with said biological cell structures,
a phosphatidylethanolamine containing cryoprotective fluid incorporated with said biological cell structures,
a digalactosyldiacylglycerol lipid containing cryoprotective fluid incorporated with said biological cell structures,
a monogalactosymonoacylglycerol containing cryoprotective fluid incorporated with said biological cell structures,
a 16:1 fatty acid containing cryoprotective fluid incorporated with said biological cell structures,
a 18:1 fatty acid containing cryoprotective fluid incorporated with said biological cell structures,
a 18:2 fatty acid containing cryoprotective fluid incorporated with said biological cell structures, and
a 18:3 fatty acid containing cryoprotective fluid incorporated with said biological cell structures.

140. A cryopreservation composition as described in clause 139 or any other clause wherein said lipid containing cryoprotective fluid incorporated with said biological cell structures comprises a high lipid concentration cryopreservation fluid incorporated with said biological cell structures.

141. A cryopreservation composition as described in clause 140 or any other clause wherein said high lipid concentration cryopreservation fluid incorporated with said biological cell structures comprises a high lipid concentration cryopreservation fluid incorporated with said biological cell structures selected from a group consisting of:

an at least about 10% higher than traditional lipid concentration cryopreservation fluid as compared to similar fluid of similar character for similar thermal treatment, an at least about 20% higher than traditional lipid concentration cryopreservation fluid as compared to similar fluid of similar character for similar thermal treatment, an at least about 40% higher than traditional lipid concentration cryopreservation fluid as compared to similar fluid of similar character for similar thermal treatment, an at least about 60% higher than traditional lipid concentration cryopreservation fluid as compared to similar fluid of similar character for similar thermal treatment, and an at least about 80% higher than traditional lipid concentration cryopreservation fluid as compared to similar fluid of similar character for similar thermal treatment.

142. A cryopreservation composition as described in clause 140 or any other clause wherein said high lipid concentration cryopreservation fluid incorporated with biological cell structures comprises a high lipid concentration cryopreservation fluid incorporated with said biological cell structures having a component selected from a group consisting of: a relatively high concentration sea buckthorn lipid, a relatively high saturated fatty acid concentration, a relatively high concentration unsaturated fatty acid concentration, a relatively high concentration palmitic acid, a relatively high concentration palmitoleic acid, a relatively high concentration oleic acid, a relatively high concentration linoleic acid, a relatively high concentration linolenic acid, a relatively high concentration lecithin, a relatively high concentration β-sitosterol, a relatively high concentration β-amyrin, a relatively high concentration γ-carotene, a relatively high concentration α-amyrin, a relatively high concentration β-carotene, a relatively high concentration lycopene, a relatively high concentration lutein, a relatively high concentration tocopherol, a relatively high concentration digalactosyldiacylglycerol, a relatively high concentration monogalactosymonoacylglycerol, a relatively high concentration 16:1 fatty acids, a relatively high concentration 18:1 fatty acids, a relatively high concentration 18:2 fatty acids, and a relatively high concentration 18:3 fatty acid.

143. A cryopreservation composition as described in clause 121 or any other clause wherein said assemblage of biological cell structures comprises an assemblage of biological cell structures selected from a group consisting of:
an assemblage of enhanced cryogenic viability blood cell structures,
an assemblage of enhanced cryogenic viability stem cell structures,
an assemblage of enhanced cryogenic viability skin cells,
an assemblage of enhanced cryogenic viability embryonic stem cells,
an assemblage of enhanced cryogenic viability neural stem cells,
an assemblage of enhanced cryogenic viability umbilical cord blood cells,
an assemblage of enhanced cryogenic viability epithelial stem cells
an assemblage of enhanced cryogenic viability cardiac stem cells
an assemblage of enhanced cryogenic viability muscle stem cells
an assemblage of enhanced cryogenic viability connective stem cells
an assemblage of enhanced cryogenic viability epithelial cells
an assemblage of enhanced cryogenic viability cardiac cells
an assemblage of enhanced cryogenic viability of muscle cells
an assemblage of enhanced cryogenic viability connective cells
an assemblage of enhanced cryogenic viability nerve cells
an assemblage of enhanced cryogenic viability histological sample cells,
an assemblage of enhanced cryogenic viability plant seed cells,
an assemblage of enhanced cryogenic viability plant shoot cells,
an assemblage of enhanced cryogenic viability ovarian tissue cell structures,
an assemblage of enhanced cryogenic viability testicular tissue cell structures,
an assemblage of enhanced cryogenic viability embryo cells,
an assemblage of enhanced cryogenic viability tumorous tissue cell structures,
an assemblage of enhanced cryogenic viability yeast cells,
an assemblage of enhanced cryogenic viability bacterial cells,
an assemblage of enhanced cryogenic viability algal cells,
an assemblage of enhanced cryogenic viability fungal cells,
an assemblage of enhanced cryogenic viability mesenchymal cells,
an assemblage of enhanced cryogenic viability keratinocyte cells,
an assemblage of enhanced cryogenic viability melanocyte cells,
an assemblage of enhanced cryogenic viability hepatocyte cells,
an assemblage of enhanced cryogenic viability oocyte cells, and
an assemblage of enhanced cryogenic viability sperm cell structures.

144. A cryopreservation composition comprising:
an assemblage of biological cell structures; and
a collection of non-naturally occurring lipid droplets contained within a cryopreservation fluid and mixed with said biological cell structures.

145. A cryopreservation composition as described in clause 144 or any other clause wherein said collection of non-naturally occurring lipid droplets contained within a cryopreservation fluid and mixed with said biological cell structures comprises unstably sized lipid droplets contained within said cryopreservation fluid 146. A cryopreservation composition as described in clause 144 or any other clause wherein said collection of non-naturally occurring lipid droplets contained within a cryopreservation fluid and mixed with said biological cell structures comprises size-modified lipid droplets contained within said cryopreservation fluid.

147. A cryopreservation composition as described in clause 146 wherein said size-modified lipid droplets contained within said cryopreservation fluid comprises a drop transformed cryopreservation fluid selected from a group consisting of:

a cryopreservation fluid containing a substance having its number of drops in said cryopreservation fluid increased by at least about 30 times,
a cryopreservation fluid containing a substance having its number of drops in said cryopreservation fluid increased by at least about 50 times,
a cryopreservation fluid containing a substance having its number of drops in said cryopreservation fluid increased by at least about 100 times,
a cryopreservation fluid containing a substance having its number of drops in said cryopreservation fluid increased by at least about 500 times,
a cryopreservation fluid containing a substance having its number of drops in said cryopreservation fluid increased by at least about 1000 times,
a cryopreservation fluid containing a substance having its number of drops in said cryopreservation fluid increased by at least about 5000 times,
a cryopreservation fluid containing a substance having its number of drops in said cryopreservation fluid increased by at least about 10000 times,
a cryopreservation fluid containing a substance having its number of drops in said cryopreservation fluid increased by at least about 50000 times, and
a cryopreservation fluid containing a substance having its number of drops in said cryopreservation fluid increased by at least about 100000 times.

148. A cryopreservation composition as described in clause 144 or any other clause wherein said collection of non-naturally occurring lipid droplets contained within a cryopreservation fluid and mixed with said biological cell structures comprises a cryopreservation fluid containing a lipid having a substantial number of relatively small droplets.

149. A cryopreservation composition as described in clause 148 or any other clause wherein said cryopreservation fluid containing a lipid having a substantial number of relatively small droplets comprises a larger drop rended cryopreservation fluid.

150. A cryopreservation composition as described in clause 147, 148, or 149 or any other clause wherein said cryopreservation fluid containing a lipid having a substantial number of relatively small droplets comprises a lipid selected from a group consisting of:
a lipid contained within said cryopreservation fluid having no substantial number of droplets larger than at least about 1000 nm,
a lipid contained within said cryopreservation fluid having no substantial number of droplets larger than at least about 900 nm,
a lipid contained within said cryopreservation fluid having no substantial number of droplets larger than at least about 700 nm,
a lipid contained within said cryopreservation fluid having no substantial number of droplets larger than at least about 500 nm,
a lipid contained within said cryopreservation fluid having no substantial number of droplets larger than at least about 300 nm,
a lipid contained within said cryopreservation fluid having no substantial number of droplets larger than at least about 100 nm,
a lipid contained within said cryopreservation fluid having no substantial number of droplets larger than at least about 70 nm,
a lipid contained within said cryopreservation fluid having no substantial number of droplets larger than at least about 50 nm, and
a lipid contained within said cryopreservation fluid having no substantial number of droplets larger than at least about 30 nm.

151. A cryopreservation composition as described in clause 150 or any other clause wherein said cryopreservation fluid containing a lipid having a substantial number of relatively small droplets comprises a fluid selected from a group consisting of:
a cryopreservation fluid containing a substance having at least about 20% of said droplets of said substance in said cryopreservation fluid at least about as small as said desired size,
a cryopreservation fluid containing a substance having at least about 40% of said droplets of said substance in said cryopreservation fluid at least about as small as said desired size,
a cryopreservation fluid containing a substance having at least about 60% of said droplets of said substance in said cryopreservation fluid at least about as small as said desired size,
a cryopreservation fluid containing a substance having at least about 80% of said droplets of said substance in said cryopreservation fluid at least about as small as said desired size, and
a cryopreservation fluid containing a substance having at least about 90% of said droplets of said substance in said cryopreservation fluid at least about as small as said desired size.

152. A cryopreservation composition as described in clause 148 or 149 or any other clause wherein said cryopreservation fluid containing a lipid having a substantial number of relatively small droplets comprises a fluid selected from a group consisting of:
a cryopreservation fluid containing a substance having its number of drops in said cryopreservation fluid increased by at least about 30 times,
a cryopreservation fluid containing a substance having its number of drops in said cryopreservation fluid increased by at least about 50 times,
a cryopreservation fluid containing a substance having its number of drops in said cryopreservation fluid increased by at least about 100 times,
a cryopreservation fluid containing a substance having its number of drops in said cryopreservation fluid increased by at least about 500 times,
a cryopreservation fluid containing a substance having its number of drops in said cryopreservation fluid increased by at least about 1000 times,
a cryopreservation fluid containing a substance having its number of drops in said cryopreservation fluid increased by at least about 5000 times,
a cryopreservation fluid containing a substance having its number of drops in said cryopreservation fluid increased by at least about 10000 times,
a cryopreservation fluid containing a substance having its number of drops in said cryopreservation fluid increased by at least about 50000 times, and
a cryopreservation fluid containing a substance having its number of drops in said cryopreservation fluid increased by at least about 100000 times.

153. A cryopreservation composition as described in clause 144, 147, or 149 or any other clause wherein said assemblage of biological cell structures comprises an assemblage of biological cell structures selected from a group consisting of:
- an assemblage of enhanced cryogenic viability blood cell structures,
- an assemblage of enhanced cryogenic viability stem cell structures,
- an assemblage of enhanced cryogenic viability skin cells,
- an assemblage of enhanced cryogenic viability embryonic stem cells,
- an assemblage of enhanced cryogenic viability neural stem cells,
- an assemblage of enhanced cryogenic viability umbilical cord blood cells,
- an assemblage of enhanced cryogenic viability epithelial stem cells
- an assemblage of enhanced cryogenic viability cardiac stem cells
- an assemblage of enhanced cryogenic viability muscle stem cells
- an assemblage of enhanced cryogenic viability connective stem cells
- an assemblage of enhanced cryogenic viability epithelial cells
- an assemblage of enhanced cryogenic viability cardiac cells
- an assemblage of enhanced cryogenic viability of muscle cells
- an assemblage of enhanced cryogenic viability connective cells
- an assemblage of enhanced cryogenic viability nerve cells
- an assemblage of enhanced cryogenic viability histological sample cells,
- an assemblage of enhanced cryogenic viability plant seed cells,
- an assemblage of enhanced cryogenic viability plant shoot cells,
- an assemblage of enhanced cryogenic viability ovarian tissue cell structures,
- an assemblage of enhanced cryogenic viability testicular tissue cell structures,
- an assemblage of enhanced cryogenic viability embryo cells,
- an assemblage of enhanced cryogenic viability tumorous tissue cell structures,
- an assemblage of enhanced cryogenic viability yeast cells,
- an assemblage of enhanced cryogenic viability bacterial cells,
- an assemblage of enhanced cryogenic viability algal cells,
- an assemblage of enhanced cryogenic viability fungal cells,
- an assemblage of enhanced cryogenic viability mesenchymal cells,
- an assemblage of enhanced cryogenic viability keratinocyte cells,
- an assemblage of enhanced cryogenic viability melanocyte cells,
- an assemblage of enhanced cryogenic viability hepatocyte cells,
- an assemblage of enhanced cryogenic viability oocyte cells, and
- an assemblage of enhanced cryogenic viability sperm cell structures.

154. A cryopreservation composition as described in clause 144 wherein said collection of non-naturally occurring lipid droplets contained within a cryopreservation fluid and mixed with said biological cell structures comprises a substance having a substantially uniform maximum size of droplets while contained within said cryopreservation fluid.

155. A cryopreservation composition as described in clause 154 wherein said substance having a substantially uniform maximum size of droplets while contained within said cryopreservation fluid comprises a substance selected from a group consisting of:
- a substance contained within said cryopreservation fluid having no substantial number of droplets larger than at least about 1000 nm,
- a substance contained within said cryopreservation fluid having no substantial number of droplets larger than at least about 900 nm,
- a substance contained within said cryopreservation fluid having no substantial number of droplets larger than at least about 700 nm,
- a substance contained within said cryopreservation fluid having no substantial number of droplets larger than at least about 500 nm,
- a substance contained within said cryopreservation fluid having no substantial number of droplets larger than at least about 300 nm,
- a substance contained within said cryopreservation fluid having no substantial number of droplets larger than at least about 100 nm,
- a substance contained within said cryopreservation fluid having no substantial number of droplets larger than at least about 70 nm,
- a substance contained within said cryopreservation fluid having no substantial number of droplets larger than at least about 50 nm, and
- a substance contained within said cryopreservation fluid having no substantial number of droplets larger than at least about 30 nm.

156. A cryopreservation composition as described in clause 154 or any other clause wherein said substance having a substantially uniform maximum size of droplets while contained within said cryopreservation fluid comprises a lipid selected from a group consisting of:
- a lipid contained within said cryopreservation fluid having no substantial number of droplets larger than at least about 1000 nm,
- a lipid contained within said cryopreservation fluid having no substantial number of droplets larger than at least about 900 nm,
- a lipid contained within said cryopreservation fluid having no substantial number of droplets larger than at least about 700 nm,
- a lipid contained within said cryopreservation fluid having no substantial number of droplets larger than at least about 500 nm,
- a lipid contained within said cryopreservation fluid having no substantial number of droplets larger than at least about 300 nm,
- a lipid contained within said cryopreservation fluid having no substantial number of droplets larger than at least about 100 nm,
- a lipid contained within said cryopreservation fluid having no substantial number of droplets larger than at least about 70 nm,
- a lipid contained within said cryopreservation fluid having no substantial number of droplets larger than at least about 50 nm, and
- a lipid contained within said cryopreservation fluid having no substantial number of droplets larger than at least about 30 nm.

157. A cryopreservation composition as described in clause 144 wherein said collection of non-naturally occurring lipid droplets contained within a cryopreservation fluid and mixed with said biological cell structures comprises a substance contained within said cryopreservation fluid having a droplet size with a skewed size distribution that favors smaller size droplets.

158. A cryopreservation composition as described in clause 157 or any other clause wherein said substance contained within said cryopreservation fluid having a droplet size with a skewed size distribution that favors smaller size droplets comprises a substance selected from a group consisting of:
- a substance contained within said cryopreservation fluid having a mode drop size of less than at least about 1000 nm,
- a substance contained within said cryopreservation fluid having a mode drop size of less than at least about 900 nm,
- a substance contained within said cryopreservation fluid having a mode drop size of less than at least about 700 nm,
- a substance contained within said cryopreservation fluid having a mode drop size of less than at least about 500 nm,
- a substance contained within said cryopreservation fluid having a mode drop size of less than at least about 300 nm,
- a substance contained within said cryopreservation fluid having a mode drop size of less than at least about 100 nm,
- a substance contained within said cryopreservation fluid having a mode drop size of less than at least about 70 nm,
- a substance contained within said cryopreservation fluid having a mode drop size of less than at least about 50 nm, and
- a substance contained within said cryopreservation fluid having a mode drop size of less than at least about 30 nm.

159. A cryopreservation composition comprising:
- an assemblage of enhanced post-cryogenic viability biological cell structures; and
- a high lipid concentration cryopreservation fluid mixed with said enhanced post-cryogenic viability biological cell structures.

160. A cryopreservation composition as described in clause 159 or any other clause wherein said high lipid concentration cryopreservation fluid incorporated with said biological cell structures comprises a high lipid concentration cryopreservation fluid incorporated with said biological cell structures selected from a group consisting of:
- an at least about 10% higher than traditional lipid concentration cryopreservation fluid as compared to similar fluid of similar character for similar thermal treatment,
- an at least about 20% higher than traditional lipid concentration cryopreservation fluid as compared to similar fluid of similar character for similar thermal treatment,
- an at least about 40% higher than traditional lipid concentration cryopreservation fluid as compared to similar fluid of similar character for similar thermal treatment,
- an at least about 60% higher than traditional lipid concentration cryopreservation fluid as compared to similar fluid of similar character for similar thermal treatment, and
- an at least about 80% higher than traditional lipid concentration cryopreservation fluid as compared to similar fluid of similar character for similar thermal treatment.

161. A cryopreservation composition as described in clause 159 or any other clause wherein said high lipid concentration cryopreservation fluid incorporated with said biological cell structures comprises a high lipid concentration cryopreservation fluid incorporated with said biological cell structures having a component selected from a group consisting of: a relatively high concentration sea buckthorn lipid, a relatively high concentration unsaturated fatty acid, a relatively high concentration saturated fatty acid, a relatively high concentration palmitic acid, a relatively high concentration palmitoleic acid, a relatively high concentration oleic acid, a relatively high concentration linoleic acid, a relatively high concentration linolenic acid, a relatively high concentration lecithin, a relatively high concentration β-sitosterol, a relatively high concentration β-amyrin, a relatively high concentration γ-carotene, a relatively high concentration α-amyrin, a relatively high concentration β-carotene, a relatively high concentration lycopene, a relatively high concentration lutein, a relatively high concentration tocopherol, a relatively high concentration digalactosyldiacylglycerol, a relatively high concentration monogalactosymonoacylglycerol, a relatively high concentration 16:1 fatty acids, a relatively high concentration 18:1 fatty acids, a relatively high concentration 18:2 fatty acids, and a relatively high concentration 18:3 fatty acid.

162. A cryopreservation composition as described in clause 159 or any other clause wherein said enhanced post-cryogenic viability assemblage of biological cell structures comprises a relatively high post-cryogenic viability assemblage of biological cell structures.

163. A cryopreservation composition as described in clause 162 or any other clause wherein said relatively high post-cryogenic viability assemblage of biological cell structures comprises an assemblage of biological cell structures selected from a group consisting of:
- an at least about 5% higher post-cryogenic viability assemblage of biological cell structures over traditional post-cryogenic cell structures of a similar character and thermal treatment,
- an at least about 10% higher post-cryogenic viability assemblage of biological cell structures over traditional post-cryogenic cell structures of a similar character and thermal treatment,
- an at least about 15% higher post-cryogenic viability assemblage of biological cell structures over traditional post-cryogenic cell structures of a similar character and thermal treatment,
- an at least about 20% higher post-cryogenic viability assemblage of biological cell structures over traditional post-cryogenic cell structures of a similar character and thermal treatment, and
- an at least about 25% higher post-cryogenic viability assemblage of biological cell structures over traditional post-cryogenic cell structures of a similar character and thermal treatment.

164. A cryopreservation composition as described in clause 162 or any other clause wherein said relatively high post-cryogenic viability assemblage of biological cell structures comprises an assemblage of biological cell structures selected from a group consisting of:
- an assemblage of biological cell structures having not less than about 80% of the pre-cryogenic viability for said biological cell structures,
- an assemblage of biological cell structures having not less than about 70% of the pre-cryogenic viability for said biological cell structures,
- an assemblage of biological cell structures having not less than about 60% of the pre-cryogenic viability for said biological cell structures,
- an assemblage of biological cell structures having not less than about 50% of the pre-cryogenic viability for said biological cell structures,
- an assemblage of biological cell structures having not less than about 40% of the pre-cryogenic viability for said biological cell structures,
- an assemblage of biological cell structures having not less than about 30% of the pre-cryogenic viability for said biological cell structures, and
- an assemblage of biological cell structures having not less than about 20% of the pre-cryogenic viability for said biological cell structures.

165. A cryopreservation composition as described in clause 159, 160, 162, or 164 or any other clause wherein said increased surface energy content cryopreservation fluid comprises a larger drop rended cryopreservation fluid.

166. A cryopreservation composition as described in clause 165 or any other clause wherein said larger drop rended cryopreservation fluid comprises a larger drop rended cryopreservation fluid selected from a group consisting of:
- a cryopreservation fluid containing a substance having no substantial number of droplets with a diameter larger than about 1000 nm,
- a cryopreservation fluid containing a substance having no substantial number of droplets with a diameter larger than about 900 nm,
- a cryopreservation fluid containing a substance having no substantial number of droplets with a diameter larger than about 700 nm,
- a cryopreservation fluid containing a substance having no substantial number of droplets with a diameter larger than about 500 nm,
- a cryopreservation fluid containing a substance having no substantial number of droplets with a diameter larger than about 300 nm,
- a cryopreservation fluid containing a substance having no substantial number of droplets with a diameter larger than about 100 nm,
- a cryopreservation fluid containing a substance having no substantial number of droplets with a diameter larger than about 70 nm,
- a cryopreservation fluid containing a substance having no substantial number of droplets with a diameter larger than about 50 nm, and
- a cryopreservation fluid containing a substance having no substantial number of droplets with a diameter larger than about 30 nm.

167. A cryopreservation composition as described in clause 159 or any other clause wherein said assemblage of biological cell structures comprises an assemblage of biological cell structures selected from a group consisting of:
- an assemblage of enhanced cryogenic viability blood cell structures,
- an assemblage of enhanced cryogenic viability stem cell structures,
- an assemblage of enhanced cryogenic viability skin cells,
- an assemblage of enhanced cryogenic viability embryonic stem cells,
- an assemblage of enhanced cryogenic viability neural stem cells,
- an assemblage of enhanced cryogenic viability umbilical cord blood cells,
- an assemblage of enhanced cryogenic viability epithelial stem cells
- an assemblage of enhanced cryogenic viability cardiac stem cells
- an assemblage of enhanced cryogenic viability muscle stem cells
- an assemblage of enhanced cryogenic viability connective stem cells
- an assemblage of enhanced cryogenic viability epithelial cells
- an assemblage of enhanced cryogenic viability cardiac cells
- an assemblage of enhanced cryogenic viability of muscle cells
- an assemblage of enhanced cryogenic viability connective cells
- an assemblage of enhanced cryogenic viability nerve cells
- an assemblage of enhanced cryogenic viability histological sample cells,
- an assemblage of enhanced cryogenic viability plant seed cells,
- an assemblage of enhanced cryogenic viability plant shoot cells,
- an assemblage of enhanced cryogenic viability ovarian tissue cell structures,
- an assemblage of enhanced cryogenic viability testicular tissue cell structures,
- an assemblage of enhanced cryogenic viability embryo cells,
- an assemblage of enhanced cryogenic viability tumorous tissue cell structures,
- an assemblage of enhanced cryogenic viability yeast cells,
- an assemblage of enhanced cryogenic viability bacterial cells,
- an assemblage of enhanced cryogenic viability algal cells,
- an assemblage of enhanced cryogenic viability fungal cells,
- an assemblage of enhanced cryogenic viability mesenchymal cells,
- an assemblage of enhanced cryogenic viability keratinocyte cells,
- an assemblage of enhanced cryogenic viability melanocyte cells,
- an assemblage of enhanced cryogenic viability hepatocyte cells,
- an assemblage of enhanced cryogenic viability oocyte cells, and
- an assemblage of enhanced cryogenic viability sperm cell structures.

168. A cryopreservation composition as described in clause 166 or any other clause wherein said assemblage of biological cell structures comprises an assemblage of biological cell structures selected from a group consisting of:
- an assemblage of enhanced cryogenic viability blood cell structures,
- an assemblage of enhanced cryogenic viability stem cell structures, an assemblage of enhanced cryogenic viability skin cells,
an assemblage of enhanced cryogenic viability embryonic stem cells,
an assemblage of enhanced cryogenic viability neural stem cells,
an assemblage of enhanced cryogenic viability umbilical cord blood cells,
an assemblage of enhanced cryogenic viability epithelial stem cells
an assemblage of enhanced cryogenic viability cardiac stem cells
an assemblage of enhanced cryogenic viability muscle stem cells
an assemblage of enhanced cryogenic viability connective stem cells
an assemblage of enhanced cryogenic viability epithelial cells
an assemblage of enhanced cryogenic viability cardiac cells
an assemblage of enhanced cryogenic viability of muscle cells
an assemblage of enhanced cryogenic viability connective cells
an assemblage of enhanced cryogenic viability nerve cells
an assemblage of enhanced cryogenic viability histological sample cells,
an assemblage of enhanced cryogenic viability plant seed cells,
an assemblage of enhanced cryogenic viability plant shoot cells,
an assemblage of enhanced cryogenic viability ovarian tissue cell structures,
an assemblage of enhanced cryogenic viability testicular tissue cell structures,
an assemblage of enhanced cryogenic viability embryo cells,
an assemblage of enhanced cryogenic viability tumorous tissue cell structures,
an assemblage of enhanced cryogenic viability yeast cells,
an assemblage of enhanced cryogenic viability bacterial cells,
an assemblage of enhanced cryogenic viability algal cells,
an assemblage of enhanced cryogenic viability fungal cells,
an assemblage of enhanced cryogenic viability mesenchymal cells,
an assemblage of enhanced cryogenic viability keratinocyte cells,
an assemblage of enhanced cryogenic viability melanocyte cells,
an assemblage of enhanced cryogenic viability hepatocyte cells,
an assemblage of enhanced cryogenic viability oocyte cells, and
an assemblage of enhanced cryogenic viability sperm cell structures.

169. A cryopreservation composition comprising:
an assemblage of biological cell structures; and
a reduced damage lipid content cryopreservation fluid mixed with said biological cell structures.

170. A cryopreservation composition as described in clause 169 or any other clause wherein said reduced damage lipid content cryopreservation fluid mixed with said biological cell structures comprises a configured lipid content cryopreservation fluid.

171. A cryopreservation composition as described in clause 169 or any other clause wherein reduced damage lipid content cryopreservation fluid mixed with said biological cell structures comprises an altered lipid content cryopreservation fluid.

172. A cryopreservation composition as described in clause 171 or any other clause wherein said altered lipid content cryopreservation fluid comprises a physically altered lipid content cryopreservation fluid.

173. A cryopreservation composition as described in clause 172 or any other clause wherein said physically altered lipid content cryopreservation fluid comprises a drop rended cryopreservation fluid.

174. A cryopreservation composition as described in clause 169 or any other clause wherein said reduced damage lipid content cryopreservation fluid comprises a cryopreservation fluid that has been frozen by reducing its temperature below the freezing point of water.

175. A cryopreservation composition as described in clause 174 or any other clause wherein said reduced damage lipid content cryopreservation fluid comprises a cryopreservation fluid that has been thawed by increasing its temperature above the freezing point of water.

176. A cryopreservation composition as described in clause 169, 404 or any other clause wherein said assemblage of biological cell structures comprises an enhanced post-cryogenic viability assemblage of biological cell structures.

177. A cryopreservation composition as described in clause 176 or any other clause wherein said enhanced post-cryogenic viability assemblage of biological cell structures comprises a relatively high post-cryogenic viability assemblage of biological cell structures.

178. A cryopreservation composition as described in clause 177 or any other clause wherein said relatively high post-cryogenic viability assemblage of biological cell structures comprises an assemblage of biological cell structures selected from a group consisting of:
an at least about 5% higher post-cryogenic viability assemblage of biological cell structures over traditional post-cryogenic cell structures of a similar character and thermal treatment,
an at least about 10% higher post-cryogenic viability assemblage of biological cell structures over traditional post-cryogenic cell structures of a similar character and thermal treatment,
an at least about 15% higher post-cryogenic viability assemblage of biological cell structures over traditional post-cryogenic cell structures of a similar character and thermal treatment,
an at least about 20% higher post-cryogenic viability assemblage of biological cell structures over traditional post-cryogenic cell structures of a similar character and thermal treatment, and
an at least about 25% higher post-cryogenic viability assemblage of biological cell structures over traditional post-cryogenic cell structures of a similar character and thermal treatment.

179. A cryopreservation composition as described in clause 177 or any other clause wherein said relatively high post-cryogenic viability assemblage of biological cell structures comprises an assemblage of biological cell structures selected from a group consisting of:
an assemblage of biological cell structures having not less than about 80% of the pre-cryogenic viability for said biological cell structures,
an assemblage of biological cell structures having not less than about 70% of the pre-cryogenic viability for said biological cell structures, an assemblage of biological cell structures having not less than about 60% of the pre-cryogenic viability for said biological cell structures,
an assemblage of biological cell structures having not less than about 50% of the pre-cryogenic viability for said biological cell structures,
an assemblage of biological cell structures having not less than about 40% of the pre-cryogenic viability for said biological cell structures,
an assemblage of biological cell structures having not less than about 30% of the pre-cryogenic viability for said biological cell structures, and
an assemblage of biological cell structures having not less than about 20% of the pre-cryogenic viability for said biological cell structures.
180. A cryopreservation composition as described in clause 169, 412, 417 or any other clause wherein said reduced damage lipid content cryopreservation fluid comprises a larger drop rended cryopreservation fluid.
181. A cryopreservation composition as described in clause 180 or any other clause wherein said larger drop rended cryopreservation fluid comprises a larger drop rended cryopreservation fluid selected from a group consisting of:
a cryopreservation fluid containing a substance having no substantial number of droplets with a diameter larger than about 1000 nm,
a cryopreservation fluid containing a substance having no substantial number of droplets with a diameter larger than about 900 nm,
a cryopreservation fluid containing a substance having no substantial number of droplets with a diameter larger than about 700 nm,
a cryopreservation fluid containing a substance having no substantial number of droplets with a diameter larger than about 500 nm,
a cryopreservation fluid containing a substance having no substantial number of droplets with a diameter larger than about 300 nm,
a cryopreservation fluid containing a substance having no substantial number of droplets with a diameter larger than about 100 nm,
a cryopreservation fluid containing a substance having no substantial number of droplets with a diameter larger than about 70 nm,
a cryopreservation fluid containing a substance having no substantial number of droplets with a diameter larger than about 50 nm, and
a cryopreservation fluid containing a substance having no substantial number of droplets with a diameter larger than about 30 nm.
182. A cryopreservation composition as described in clause 169 or any other clause wherein said assemblage of biological cell structures comprises an assemblage of biological cell structures selected from a group consisting of:
an assemblage of enhanced cryogenic viability blood cell structures,
an assemblage of enhanced cryogenic viability stem cell structures,
an assemblage of enhanced cryogenic viability skin cells,
an assemblage of enhanced cryogenic viability embryonic stem cells,
an assemblage of enhanced cryogenic viability neural stem cells,
an assemblage of enhanced cryogenic viability umbilical cord blood cells,
an assemblage of enhanced cryogenic viability epithelial stem cells
an assemblage of enhanced cryogenic viability cardiac stem cells
an assemblage of enhanced cryogenic viability muscle stem cells
an assemblage of enhanced cryogenic viability connective stem cells
an assemblage of enhanced cryogenic viability epithelial cells
an assemblage of enhanced cryogenic viability cardiac cells
an assemblage of enhanced cryogenic viability of muscle cells
an assemblage of enhanced cryogenic viability connective cells
an assemblage of enhanced cryogenic viability nerve cells
an assemblage of enhanced cryogenic viability histological sample cells,
an assemblage of enhanced cryogenic viability plant seed cells,
an assemblage of enhanced cryogenic viability plant shoot cells,
an assemblage of enhanced cryogenic viability ovarian tissue cell structures,
an assemblage of enhanced cryogenic viability testicular tissue cell structures,
an assemblage of enhanced cryogenic viability embryo cells,
an assemblage of enhanced cryogenic viability tumorous tissue cell structures,
an assemblage of enhanced cryogenic viability yeast cells,
an assemblage of enhanced cryogenic viability bacterial cells,
an assemblage of enhanced cryogenic viability algal cells,
an assemblage of enhanced cryogenic viability fungal cells,
an assemblage of enhanced cryogenic viability mesenchymal cells,
an assemblage of enhanced cryogenic viability keratinocyte cells,
an assemblage of enhanced cryogenic viability melanocyte cells,
an assemblage of enhanced cryogenic viability hepatocyte cells,
an assemblage of enhanced cryogenic viability oocyte cells, and
an assemblage of enhanced cryogenic viability sperm cell structures.
183. A cryopreservation composition as described in clause 181 or any other clause wherein said assemblage of biological cell structures comprises an assemblage of biological cell structures selected from a group consisting of:
an assemblage of enhanced cryogenic viability blood cell structures,
an assemblage of enhanced cryogenic viability stem cell structures,
an assemblage of enhanced cryogenic viability skin cells,
an assemblage of enhanced cryogenic viability embryonic stem cells,
an assemblage of enhanced cryogenic viability neural stem cells,
an assemblage of enhanced cryogenic viability umbilical cord blood cells,
an assemblage of enhanced cryogenic viability epithelial stem cells an assemblage of enhanced cryogenic viability cardiac stem cells an assemblage of enhanced cryogenic viability muscle stem cells an assemblage of enhanced cryogenic viability connective stem cells an assemblage of enhanced cryogenic viability epithelial cells an assemblage of enhanced cryogenic viability cardiac cells an assemblage of enhanced cryogenic viability of muscle cells an assemblage of enhanced cryogenic viability connective cells an assemblage of enhanced cryogenic viability nerve cells an assemblage of enhanced cryogenic viability histological sample cells, an assemblage of enhanced cryogenic viability plant seed cells, an assemblage of enhanced cryogenic viability plant shoot cells, an assemblage of enhanced cryogenic viability ovarian tissue cell structures, an assemblage of enhanced cryogenic viability testicular tissue cell structures, an assemblage of enhanced cryogenic viability embryo cells, an assemblage of enhanced cryogenic viability tumorous tissue cell structures, an assemblage of enhanced cryogenic viability yeast cells, an assemblage of enhanced cryogenic viability bacterial cells, an assemblage of enhanced cryogenic viability algal cells, an assemblage of enhanced cryogenic viability fungal cells, an assemblage of enhanced cryogenic viability mesenchymal cells, an assemblage of enhanced cryogenic viability keratinocyte cells, an assemblage of enhanced cryogenic viability melanocyte cells, an assemblage of enhanced cryogenic viability hepatocyte cells, an assemblage of enhanced cryogenic viability oocyte cells, and an assemblage of enhanced cryogenic viability sperm cell structures.

184. A cryopreservation composition comprising:
an enhanced post-cryogenic viability assemblage of biological cell structures; and
a sized droplet cryopreservation fluid mixed with said biological cell structures.

185. A cryopreservation composition as described in clause 184 or any other clause wherein said sized droplet cryopreservation fluid mixed with said biological cell structures comprises a drop rended cryopreservation fluid.

186. A cryopreservation composition as described in clause 185 or any other clause wherein said sized droplet cryopreservation fluid mixed with said biological cell structures comprises a lipid drop rended cryopreservation fluid.

187. A cryopreservation composition as described in clause 184 or any other clause wherein said fluid comprises a sized droplet cryopreservation fluid that has been frozen by reducing its temperature below the freezing point of water.

188. A cryopreservation composition as described in clause 187 or any other clause wherein said sized droplet cryopreservation fluid comprises a sized droplet cryopreservation fluid that has been thawed by increasing its temperature above the freezing point of water.

189. A cryopreservation composition as described in clause 184 or 185 or any other clause wherein said sized droplet cryopreservation fluid mixed with said biological cell structures comprises a cryopreservation fluid selected from a group consisting of:
a cryopreservation fluid containing a substance having no substantial number of droplets with a diameter larger than about 1000 nm,
a cryopreservation fluid containing a substance having no substantial number of droplets with a diameter larger than about 900 nm,
a cryopreservation fluid containing a substance having no substantial number of droplets with a diameter larger than about 700 nm,
a cryopreservation fluid containing a substance having no substantial number of droplets with a diameter larger than about 500 nm,
a cryopreservation fluid containing a substance having no substantial number of droplets with a diameter larger than about 300 nm,
a cryopreservation fluid containing a substance having no substantial number of droplets with a diameter larger than about 100 nm,
a cryopreservation fluid containing a substance having no substantial number of droplets with a diameter larger than about 70 nm,
a cryopreservation fluid containing a substance having no substantial number of droplets with a diameter larger than about 50 nm, and
a cryopreservation fluid containing a substance having no substantial number of droplets with a diameter larger than about 30 nm.

190. A cryopreservation composition as described in clause 185 or any other clause wherein said sized droplet cryopreservation fluid comprises a cryopreservation fluid selected from a group consisting of:
a cryopreservation fluid containing a substance having its number of drops in said cryopreservation fluid increased by at least about 30 times,
a cryopreservation fluid containing a substance having its number of drops in said cryopreservation fluid increased by at least about 50 times,
a cryopreservation fluid containing a substance having its number of drops in said cryopreservation fluid increased by at least about 100 times,
a cryopreservation fluid containing a substance having its number of drops in said cryopreservation fluid increased by at least about 500 times,
a cryopreservation fluid containing a substance having its number of drops in said cryopreservation fluid increased by at least about 1000 times,
a cryopreservation fluid containing a substance having its number of drops in said cryopreservation fluid increased by at least about 5000 times,
a cryopreservation fluid containing a substance having its number of drops in said cryopreservation fluid increased by at least about 10000 times,
a cryopreservation fluid containing a substance having its number of drops in said cryopreservation fluid increased by at least about 50000 times, and a cryopreservation fluid containing a substance having its number of drops in said cryopreservation fluid increased by at least about 100000 times.

191. A cryopreservation composition as described in clause 184 or any other clause wherein said sized droplet cryopreservation fluid mixed with said biological cell structures comprises a cryopreservation fluid containing a lipid having a substantial number of relatively small droplets.

192. A cryopreservation composition as described in clause USa230 or any other clause wherein said cryopreservation fluid containing a lipid having a substantial number of relatively small droplets comprises a larger drop rended cryopreservation fluid.

193. A cryopreservation composition as described in clause 190, 191 or 192 or any other clause wherein said cryopreservation fluid containing a lipid having a substantial number of relatively small droplets comprises a cryopreservation fluid selected from a group consisting of:
  a lipid containing cryopreservation fluid having no substantial number of droplets larger than at least about 1000 nm,
  a lipid containing cryopreservation fluid having no substantial number of droplets larger than at least about 900 nm,
  a lipid containing cryopreservation fluid having no substantial number of droplets larger than at least about 700 nm,
  a lipid containing cryopreservation fluid having no substantial number of droplets larger than at least about 500 nm,
  a lipid containing cryopreservation fluid having no substantial number of droplets larger than at least about 300 nm,
  a lipid containing cryopreservation fluid having no substantial number of droplets larger than at least about 100 nm,
  a lipid containing cryopreservation fluid having no substantial number of droplets larger than at least about 70 nm,
  a lipid containing cryopreservation fluid having no substantial number of droplets larger than at least about 50 nm, and
  a lipid containing cryopreservation fluid having no substantial number of droplets larger than at least about 30 nm.

194. A cryopreservation composition as described in clause 193 or any other clause wherein said lipid containing cryopreservation fluid comprises a cryopreservation fluid selected from a group consisting of:
  a cryopreservation fluid containing a substance having at least about 20% of said droplets of said substance in said cryopreservation fluid at least about as small as said desired size,
  a cryopreservation fluid containing a substance having at least about 40% of said droplets of said substance in said cryopreservation fluid at least about as small as said desired size,
  a cryopreservation fluid containing a substance having at least about 60% of said droplets of said substance in said cryopreservation fluid at least about as small as said desired size,
  a cryopreservation fluid containing a substance having at least about 80% of said droplets of said substance in said cryopreservation fluid at least about as small as said desired size, and
  a cryopreservation fluid containing a substance having at least about 90% of said droplets of said substance in said cryopreservation fluid at least about as small as said desired size.

195. A cryopreservation composition as described in clause 191 or 192 or any other clause wherein said lipid containing cryopreservation fluid comprises a cryopreservation fluid selected from a group consisting of:
  a cryopreservation fluid containing a lipid having its number of drops in said cryopreservation fluid increased by at least about 30 times,
  a cryopreservation fluid containing a lipid having its number of drops in said cryopreservation fluid increased by at least about 50 times,
  a cryopreservation fluid containing a lipid having its number of drops in said cryopreservation fluid increased by at least about 100 times,
  a cryopreservation fluid containing a lipid having its number of drops in said cryopreservation fluid increased by at least about 500 times,
  a cryopreservation fluid containing a lipid having its number of drops in said cryopreservation fluid increased by at least about 1000 times,
  a cryopreservation fluid containing a lipid having its number of drops in said cryopreservation fluid increased by at least about 5000 times,
  a cryopreservation fluid containing a lipid having its number of drops in said cryopreservation fluid increased by at least about 10000 times,
  a cryopreservation fluid containing a lipid having its number of drops in said cryopreservation fluid increased by at least about 50000 times, and
  a cryopreservation fluid containing a lipid having its number of drops in said cryopreservation fluid increased by at least about 100000 times.

196. A cryopreservation composition as described in clause 184 or any other clause wherein said assemblage of biological cell structures comprises an assemblage of biological cell structures selected from a group consisting of:
  an assemblage of enhanced cryogenic viability blood cell structures,
  an assemblage of enhanced cryogenic viability stem cell structures,
  an assemblage of enhanced cryogenic viability skin cells,
  an assemblage of enhanced cryogenic viability embryonic stem cells,
  an assemblage of enhanced cryogenic viability neural stem cells,
  an assemblage of enhanced cryogenic viability umbilical cord blood cells,
  an assemblage of enhanced cryogenic viability epithelial stem cells
  an assemblage of enhanced cryogenic viability cardiac stem cells
  an assemblage of enhanced cryogenic viability muscle stem cells
  an assemblage of enhanced cryogenic viability connective stem cells
  an assemblage of enhanced cryogenic viability epithelial cells
  an assemblage of enhanced cryogenic viability cardiac cells
  an assemblage of enhanced cryogenic viability of muscle cells
  an assemblage of enhanced cryogenic viability connective cells an assemblage of enhanced cryogenic viability nerve cells
an assemblage of enhanced cryogenic viability histological sample cells,
an assemblage of enhanced cryogenic viability plant seed cells,
an assemblage of enhanced cryogenic viability plant shoot cells,
an assemblage of enhanced cryogenic viability ovarian tissue cell structures,
an assemblage of enhanced cryogenic viability testicular tissue cell structures,
an assemblage of enhanced cryogenic viability embryo cells,
an assemblage of enhanced cryogenic viability tumorous tissue cell structures,
an assemblage of enhanced cryogenic viability yeast cells,
an assemblage of enhanced cryogenic viability bacterial cells,
an assemblage of enhanced cryogenic viability algal cells,
an assemblage of enhanced cryogenic viability fungal cells,
an assemblage of enhanced cryogenic viability mesenchymal cells,
an assemblage of enhanced cryogenic viability keratinocyte cells,
an assemblage of enhanced cryogenic viability melanocyte cells,
an assemblage of enhanced cryogenic viability hepatocyte cells,
an assemblage of enhanced cryogenic viability oocyte cells, and
an assemblage of enhanced cryogenic viability sperm cell structures.

197. A cryopreservation composition as described in clause 193 or any other clause wherein said assemblage of biological cell structures comprises an assemblage of biological cell structures selected from a group consisting of:
an assemblage of enhanced cryogenic viability blood cell structures,
an assemblage of enhanced cryogenic viability stem cell structures,
an assemblage of enhanced cryogenic viability skin cells,
an assemblage of enhanced cryogenic viability embryonic stem cells,
an assemblage of enhanced cryogenic viability neural stem cells,
an assemblage of enhanced cryogenic viability umbilical cord blood cells,
an assemblage of enhanced cryogenic viability epithelial stem cells
an assemblage of enhanced cryogenic viability cardiac stem cells
an assemblage of enhanced cryogenic viability muscle stem cells
an assemblage of enhanced cryogenic viability connective stem cells
an assemblage of enhanced cryogenic viability epithelial cells
an assemblage of enhanced cryogenic viability cardiac cells
an assemblage of enhanced cryogenic viability of muscle cells
an assemblage of enhanced cryogenic viability connective cells
an assemblage of enhanced cryogenic viability nerve cells
an assemblage of enhanced cryogenic viability histological sample cells,
an assemblage of enhanced cryogenic viability plant seed cells,
an assemblage of enhanced cryogenic viability plant shoot cells,
an assemblage of enhanced cryogenic viability ovarian tissue cell structures,
an assemblage of enhanced cryogenic viability testicular tissue cell structures,
an assemblage of enhanced cryogenic viability embryo cells,
an assemblage of enhanced cryogenic viability tumorous tissue cell structures,
an assemblage of enhanced cryogenic viability yeast cells,
an assemblage of enhanced cryogenic viability bacterial cells,
an assemblage of enhanced cryogenic viability algal cells,
an assemblage of enhanced cryogenic viability fungal cells,
an assemblage of enhanced cryogenic viability mesenchymal cells,
an assemblage of enhanced cryogenic viability keratinocyte cells,
an assemblage of enhanced cryogenic viability melanocyte cells,
an assemblage of enhanced cryogenic viability hepatocyte cells,
an assemblage of enhanced cryogenic viability oocyte cells, and
an assemblage of enhanced cryogenic viability sperm cell structures.

198. A cryopreservation composition as described in clause 184 wherein said sized droplet cryopreservation fluid mixed with said biological cell structures comprises a cryopreservation fluid containing a substance having a substantially uniform maximum size of droplets while contained within said cryopreservation fluid.

199. A cryopreservation composition as described in clause 198 wherein said cryopreservation fluid containing a substance having a substantially uniform maximum size of droplets while contained within said cryopreservation fluid comprises a substance selected from a group consisting of:
a substance contained within said cryopreservation fluid having no substantial number of droplets larger than at least about 1000 nm,
a substance contained within said cryopreservation fluid having no substantial number of droplets larger than at least about 900 nm,
a substance contained within said cryopreservation fluid having no substantial number of droplets larger than at least about 700 nm,
a substance contained within said cryopreservation fluid having no substantial number of droplets larger than at least about 500 nm,
a substance contained within said cryopreservation fluid having no substantial number of droplets larger than at least about 300 nm,
a substance contained within said cryopreservation fluid having no substantial number of droplets larger than at least about 100 nm,
a substance contained within said cryopreservation fluid having no substantial number of droplets larger than at least about 70 nm, a substance contained within said cryopreservation fluid having no substantial number of droplets larger than at least about 50 nm, and
a substance contained within said cryopreservation fluid having no substantial number of droplets larger than at least about 30 nm.

200. A cryopreservation composition as described in clause 198 or any other clause wherein said cryopreservation fluid containing a substance having a substantially uniform maximum size of droplets while contained within said cryopreservation fluid comprises a cryopreservation fluid containing a lipid selected from a group consisting of:
a lipid contained within said cryopreservation fluid having no substantial number of droplets larger than at least about 1000 nm,
a lipid contained within said cryopreservation fluid having no substantial number of droplets larger than at least about 900 nm,
a lipid contained within said cryopreservation fluid having no substantial number of droplets larger than at least about 700 nm,
a lipid contained within said cryopreservation fluid having no substantial number of droplets larger than at least about 500 nm,
a lipid contained within said cryopreservation fluid having no substantial number of droplets larger than at least about 300 nm,
a lipid contained within said cryopreservation fluid having no substantial number of droplets larger than at least about 100 nm,
a lipid contained within said cryopreservation fluid having no substantial number of droplets larger than at least about 70 nm,
a lipid contained within said cryopreservation fluid having no substantial number of droplets larger than at least about 50 nm, and
a lipid contained within said cryopreservation fluid having no substantial number of droplets larger than at least about 30 nm.

201. A cryopreservation composition as described in clause 184 wherein said sized droplet cryopreservation fluid mixed with said biological cell structures comprises a substance contained within said cryopreservation fluid having a droplet size with a skewed size distribution that favors smaller size droplets.

202. A cryopreservation composition as described in clause 201 or any other clause wherein said substance contained within said cryopreservation fluid having a droplet size with a skewed size distribution that favors smaller size droplets comprises a lipid selected from a group consisting of:
a lipid contained within said cryopreservation fluid having a mode drop size of less than at least about 1000 nm,
a lipid contained within said cryopreservation fluid having a mode drop size of less than at least about 900 nm,
a lipid contained within said cryopreservation fluid having a mode drop size of less than at least about 700 nm,
a lipid contained within said cryopreservation fluid having a mode drop size of less than at least about 500 nm,
a lipid contained within said cryopreservation fluid having a mode drop size of less than at least about 300 nm,
a lipid contained within said cryopreservation fluid having a mode drop size of less than at least about 100 nm,
a lipid contained within said cryopreservation fluid having a mode drop size of less than at least about 70 nm,
a lipid contained within said cryopreservation fluid having a mode drop size of less than at least about 50 nm, and
a lipid contained within said cryopreservation fluid having a mode drop size of less than at least about 30 nm.

203. A cryopreservation composition comprising:
an assemblage of biological cell structures;
a foundation medium; and
a cryopreservation fluid component selected from a group consisting of: sea buckthorn lipids, saturated fatty acids, unsaturated fatty acids, lauric acid, myristic acid, palmitic acid, stearic acid, arachadonic acid, palmitoleic acid, oleic acid, linoleic acid, linolenic acid, arachadonic acid, lecithin, triglycerides, spermaceti, bees wax, carnuba wax, sphingomyelins, monoterpenes, sesquiterpenes, diterpenes, sesterterpenes, triterpenes, cholic acid, oleic acid, β-sitosterol, β-amyrin, γ-carotene, α-amyrin, β-carotene, lycopene, lutein, tocopherol, ubiquinol, tocotrienols, eugenol, phosphatidic acid, phosphatidylethanolamine, phosphatidylcholine, phosphatidylserine, phosphatidylinositol, ceramide phosphorylcholine, ceramine phosphorylglycerol, digalactosyldiacylglycerol, monogalactosymonoacylglycerol, 16:1 fatty acids, 18:1 fatty acids, 18:2 fatty acids, 18:3 fatty acids, natural rubber, and gutta-percha.

204. A cryopreservation composition comprising:
an assemblage of biological cell structures;
a foundation medium;
a lipid cryoprotectant; and
a cryopreservation fluid component selected from a group consisting of: thiols, ascorbic acid, polyprenols, superoxide dismutase, catalase, peroxidase, lipoic acid, uric acid, hydrophobic substances (non-lipid), silicones, fluorocarbons, glutathione, melatonin, peroxiredoxins, resveratrol, phytic acid, flavonoids, vitamin A, vitamin E, vitamin D2, vitamin K1, lipid soluble substances, and lipid soluble vitamins.

205. A cryopreservation composition as described in clause 203 or 204 or any other clause wherein said assemblage of biological cell structures comprises an enhanced post-cryogenic viability assemblage of biological cell structures.

206. A cryopreservation composition as described in clause 205 or any other clause wherein said enhanced post-cryogenic viability assemblage of biological cell structures comprises a relatively high post-cryogenic viability assemblage of biological cell structures.

207. A cryopreservation composition as described in clause 206 or any other clause wherein said relatively high post-cryogenic viability assemblage of biological cell structures comprises an assemblage of biological cell structures selected from a group consisting of:
an at least about 5% higher post-cryogenic viability assemblage of biological cell structures over traditional post-cryogenic cell structures of a similar character and thermal treatment,
an at least about 10% higher post-cryogenic viability assemblage of biological cell structures over traditional post-cryogenic cell structures of a similar character and thermal treatment,
an at least about 15% higher post-cryogenic viability assemblage of biological cell structures over traditional post-cryogenic cell structures of a similar character and thermal treatment, an at least about 20% higher post-cryogenic viability assemblage of biological cell structures over traditional post-cryogenic cell structures of a similar character and thermal treatment, and an at least about 25% higher post-cryogenic viability assemblage of biological cell structures over traditional post-cryogenic cell structures of a similar character and thermal treatment.

208. A cryopreservation composition as described in clause 206 or any other clause wherein said relatively high post-cryogenic viability assemblage of biological cell structures comprises an assemblage of biological cell structures selected from a group consisting of:
an assemblage of biological cell structures having not less than about 80% of the pre-cryogenic viability for said biological cell structures,
an assemblage of biological cell structures having not less than about 70% of the pre-cryogenic viability for said biological cell structures,
an assemblage of biological cell structures having not less than about 60% of the pre-cryogenic viability for said biological cell structures,
an assemblage of biological cell structures having not less than about 50% of the pre-cryogenic viability for said biological cell structures,
an assemblage of biological cell structures having not less than about 40% of the pre-cryogenic viability for said biological cell structures,
an assemblage of biological cell structures having not less than about 30% of the pre-cryogenic viability for said biological cell structures, and
an assemblage of biological cell structures having not less than about 20% of the pre-cryogenic viability for said biological cell structures.

209. A cryopreservation composition as described in clause 205 or any other clause wherein said cryopreservation fluid comprises a substantially increased surface energy cryopreservation fluid.

210. A cryopreservation composition as described in clause 209 or any other clause wherein said substantially increased surface energy cryopreservation fluid comprises a substantially increased surface energy cryopreservation fluid selected from a group consisting of:
a cryopreservation fluid containing a substance having its surface energy increased by at least about 100 j/kg surface energy,
a cryopreservation fluid containing a substance having its surface energy increased by at least about 270 j/kg surface energy,
a cryopreservation fluid containing a substance having its surface energy increased by at least about 320 j/kg surface energy,
a cryopreservation fluid containing a substance having its surface energy increased by at least about 650 j/kg surface energy,
a cryopreservation fluid containing a substance having its surface energy increased by at least about 1050 j/kg surface energy,
a cryopreservation fluid containing a substance having its surface energy increased by at least about 3600 j/kg surface energy, and
a cryopreservation fluid containing a substance having its surface energy increased by at least about 5200 j/kg surface energy.

211. A cryopreservation composition as described in clause 209 or any other clause wherein said substantially increased surface energy cryopreservation fluid comprises a substantially increased surface energy cryopreservation fluid selected from a group consisting of:
a cryopreservation fluid having a surface energy of a substance in said cryopreservation fluid increased to at least about 200 j/kg surface energy,
a cryopreservation fluid having a surface energy of a substance in said cryopreservation fluid increased to at least about 420 j/kg surface energy,
a cryopreservation fluid having a surface energy of a substance in said cryopreservation fluid increased to at least about 760 j/kg surface energy,
a cryopreservation fluid having a surface energy of a substance in said cryopreservation fluid increased to at least about 1200 j/kg surface energy,
a cryopreservation fluid having a surface energy of a substance in said cryopreservation fluid increased to at least about 3800 j/kg surface energy, and
a cryopreservation fluid having a surface energy of a substance in said cryopreservation fluid increased to at least about 5400 j/kg surface energy.

212. A cryopreservation composition as described in clause 209 or any other clause wherein said substantially increased surface energy cryopreservation fluid comprises a substantially increased surface energy cryopreservation fluid selected from a group consisting of:
a cryopreservation fluid containing a substance having its surface energy increased by at least about 30%,
a cryopreservation fluid containing a substance having its surface energy increased by at least about 50%,
a cryopreservation fluid containing a substance having its surface energy increased by at least about 100%,
a cryopreservation fluid containing a substance having its surface energy increased by at least about 3 times,
a cryopreservation fluid containing a substance having its surface energy increased by at least about 5 times,
a cryopreservation fluid containing a substance having its surface energy increased by at least about 10 times,
a cryopreservation fluid containing a substance having its surface energy increased by at least about 30 times, and
a cryopreservation fluid containing a substance having its surface energy increased by at least about 50 times.

213. A cryopreservation composition as described in clause 205 or any other clause wherein said cryopreservation composition comprises a drop transformed cryopreservation fluid.

214. A cryopreservation composition as described in clause 213 or any other clause wherein said drop transformed cryopreservation fluid comprises a drop transformed cryopreservation fluid selected from a group consisting of:
a cryopreservation fluid containing a substance having its number of drops in said cryopreservation fluid increased by at least about 30 times,
a cryopreservation fluid containing a substance having its number of drops in said cryopreservation fluid increased by at least about 50 times,
a cryopreservation fluid containing a substance having its number of drops in said cryopreservation fluid increased by at least about 100 times,
a cryopreservation fluid containing a substance having its number of drops in said cryopreservation fluid increased by at least about 500 times,
a cryopreservation fluid containing a substance having its number of drops in said cryopreservation fluid increased by at least about 1000 times, a cryopreservation fluid containing a substance having its number of drops in said cryopreservation fluid increased by at least about 5000 times, a cryopreservation fluid containing a substance having its number of drops in said cryopreservation fluid increased by at least about 10000 times, a cryopreservation fluid containing a substance having its number of drops in said cryopreservation fluid increased by at least about 50000 times, and a cryopreservation fluid containing a substance having its number of drops in said cryopreservation fluid increased by at least about 100000 times.

215. A cryopreservation composition as described in clause 205 or any other clause wherein said cryopreservation composition comprises a larger drop rended cryopreservation fluid.

216. A cryopreservation composition as described in clause 215 or any other clause wherein said larger drop rended cryopreservation fluid comprises a larger drop rended cryopreservation fluid selected from a group consisting of:

a cryopreservation fluid containing a substance having no substantial number of droplets with a diameter larger than about 1000 nm, a cryopreservation fluid containing a substance having no substantial number of droplets with a diameter larger than about 900 nm, a cryopreservation fluid containing a substance having no substantial number of droplets with a diameter larger than about 700 nm, a cryopreservation fluid containing a substance having no substantial number of droplets with a diameter larger than about 500 nm, a cryopreservation fluid containing a substance having no substantial number of droplets with a diameter larger than about 300 nm, a cryopreservation fluid containing a substance having no substantial number of droplets with a diameter larger than about 100 nm, a cryopreservation fluid containing a substance having no substantial number of droplets with a diameter larger than about 70 nm, a cryopreservation fluid containing a substance having no substantial number of droplets with a diameter larger than about 50 nm, and a cryopreservation fluid containing a substance having no substantial number of droplets with a diameter larger than about 30 nm.

217. A cryopreservation composition as described in clause 205 or any other clause wherein said cryopreservation composition comprises a cryopreservation fluid that has been frozen by reducing its temperature below the freezing point of water.

218. A cryopreservation composition as described in clause CSa657.06 or any other clause wherein said cryopreservation composition comprises a cryopreservation fluid that has been thawed by increasing its temperature above the freezing point of water.

219. A cryopreservation composition as described in clause 203 or 204 or any other clause wherein said assemblage of biological cell structures comprises an assemblage of biological cell structures selected from a group consisting of:

an assemblage of enhanced cryogenic viability blood cell structures, an assemblage of enhanced cryogenic viability stem cell structures, an assemblage of enhanced cryogenic viability skin cells, an assemblage of enhanced cryogenic viability embryonic stem cells, an assemblage of enhanced cryogenic viability neural stem cells, an assemblage of enhanced cryogenic viability umbilical cord blood cells, an assemblage of enhanced cryogenic viability epithelial stem cells an assemblage of enhanced cryogenic viability cardiac stem cells an assemblage of enhanced cryogenic viability muscle stem cells an assemblage of enhanced cryogenic viability connective stem cells an assemblage of enhanced cryogenic viability epithelial cells an assemblage of enhanced cryogenic viability cardiac cells an assemblage of enhanced cryogenic viability of muscle cells an assemblage of enhanced cryogenic viability connective cells an assemblage of enhanced cryogenic viability nerve cells an assemblage of enhanced cryogenic viability histological sample cells, an assemblage of enhanced cryogenic viability plant seed cells, an assemblage of enhanced cryogenic viability plant shoot cells, an assemblage of enhanced cryogenic viability ovarian tissue cell structures, an assemblage of enhanced cryogenic viability testicular tissue cell structures, an assemblage of enhanced cryogenic viability embryo cells, an assemblage of enhanced cryogenic viability tumorous tissue cell structures, an assemblage of enhanced cryogenic viability yeast cells, an assemblage of enhanced cryogenic viability bacterial cells, an assemblage of enhanced cryogenic viability algal cells, an assemblage of enhanced cryogenic viability fungal cells, an assemblage of enhanced cryogenic viability mesenchymal cells, an assemblage of enhanced cryogenic viability keratinocyte cells, an assemblage of enhanced cryogenic viability melanocyte cells, an assemblage of enhanced cryogenic viability hepatocyte cells, an assemblage of enhanced cryogenic viability oocyte cells, and an assemblage of enhanced cryogenic viability sperm cell structures.

220. A cryopreservation composition as described in clause 205 or any other clause wherein said assemblage of biological cell structures comprises an assemblage of biological cell structures selected from a group consisting of:

an assemblage of enhanced cryogenic viability blood cell structures, an assemblage of enhanced cryogenic viability stem cell structures, an assemblage of enhanced cryogenic viability skin cells, an assemblage of enhanced cryogenic viability embryonic stem cells,
an assemblage of enhanced cryogenic viability neural stem cells,
an assemblage of enhanced cryogenic viability umbilical cord blood cells,
an assemblage of enhanced cryogenic viability epithelial stem cells
an assemblage of enhanced cryogenic viability cardiac stem cells
an assemblage of enhanced cryogenic viability muscle stem cells
an assemblage of enhanced cryogenic viability connective stem cells
an assemblage of enhanced cryogenic viability epithelial cells
an assemblage of enhanced cryogenic viability cardiac cells
an assemblage of enhanced cryogenic viability of muscle cells
an assemblage of enhanced cryogenic viability connective cells
an assemblage of enhanced cryogenic viability nerve cells
an assemblage of enhanced cryogenic viability histological sample cells,
an assemblage of enhanced cryogenic viability plant seed cells,
an assemblage of enhanced cryogenic viability plant shoot cells,
an assemblage of enhanced cryogenic viability ovarian tissue cell structures,
an assemblage of enhanced cryogenic viability testicular tissue cell structures,
an assemblage of enhanced cryogenic viability embryo cells,
an assemblage of enhanced cryogenic viability tumorous tissue cell structures,
an assemblage of enhanced cryogenic viability yeast cells,
an assemblage of enhanced cryogenic viability bacterial cells,
an assemblage of enhanced cryogenic viability algal cells,
an assemblage of enhanced cryogenic viability fungal cells,
an assemblage of enhanced cryogenic viability mesenchymal cells,
an assemblage of enhanced cryogenic viability keratinocyte cells,
an assemblage of enhanced cryogenic viability melanocyte cells,
an assemblage of enhanced cryogenic viability hepatocyte cells,
an assemblage of enhanced cryogenic viability oocyte cells, and
an assemblage of enhanced cryogenic viability sperm cell structures.

As can be easily understood from the foregoing, the basic concepts of the present invention may be embodied in a variety of ways. It involves both cryopreservation techniques and processes as well as substances and devices to accomplish the appropriate cryopreservation. In this application, the cryopreservation devices are often disclosed as part of the explanation of the process. The invention includes both methods and apparatus with apparatus shown to be the inherent equipment needed to achieve the various steps explained and visa versa. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully enumerate all generic aspects of the invention and may not explicitly show how each feature or element can actually be representative of a broader function or of a great variety of alternative or equivalent elements. Again, these are implicitly included in this disclosure. Where the invention is described in device- or substance-oriented terminology, each element of the device or substance implicitly performs a function. Both method and process claims should be understood as included to address the functions the invention and each element performs. Neither the description nor the terminology is intended to limit the scope of the claims that may be included in this or any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that language changes and broader or more detailed claiming may be accomplished at a later date. With this understanding, the reader should be aware that this disclosure is to be understood to support a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically associated. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of the act of "mixing" should be understood to encompass disclosure of a "mixer"—whether explicitly discussed or not—and, conversely, were there effectively disclosure of a "mixer, such a disclosure should be understood to encompass disclosure of the act of "mixing" and even a "means for mixing." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any priority case(s) referenced by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

REFERENCES TO BE INCORPORATED BY REFERENCE

U.S. PATENTS

| Pat. No. | Kind Code | Issue Date | Name of Patentee or Applicant of cited Document |
|---|---|---|---|
| 7,622,143 | B2 | 2009-11-24 | Herickhoff et al. |
| 8,202,558 | B2 | 2012-06-19 | Herickhoff et al. |

U.S. PATENTS

| Pat. No. | Kind Code | Issue Date | Name of Patentee or Applicant of cited Document |
|---|---|---|---|
| 7,820,425 | B2 | 2010-10-26 | Schenk |
| 7,838,210 | B2 | 2010-11-23 | Ludwig et al. |
| 7,892,725 | XX | 2011-02-22 | Graham et al. |

U.S. PATENT APPLICATION PUBLICATIONS

| Publication Number | Kind Code | Publication Date | Name of Patentee or Applicant of cited Document |
|---|---|---|---|
| 20110086336 | A1 | 2011-04-14 | Herickhoff et al. |
| 20060222724 | A1 | 2006-10-05 | Herickhoff et al. |
| 20090123906 | A1 | 2009-05-14 | Herickhoff |
| 20100311036 |  | 2010-06-09 | He |

FOREIGN PATENT DOCUMENTS

| Foreign Document Number | Country Code | Kind Code | Publication Date | Name of Patentee or Applicant of cited Document |
|---|---|---|---|---|
| 2009109550 | WO | A1 | 2009-09-11 | Sanofi Pasteur |

NON-PATENT LITERATURE DOCUMENTS

Tcholakova, Slavka et al; "Role of Surfactant Type and Concentration for the Mean Drop Size during Emulsification in Turbulent Flow;" Langmuir 2004, 20, 7444-7458

Adiga, K. C.; "Droplet Breakup Energies and Formation of Ultra-fine Mist"; NanoMist Systems, LLC; The Navy Technology Center for Safety and Survivability; Chemistry Division, Naval Research Laboratory; Washington D.C.; 14 pages Seidel Jr., George; "Modifying oocytes and embryos to improve their cryopreservation;" Theriogenology 65 (2006) 228-235; Animal Reproduction and Biotechnology Laboratory, Colorado State University Smith, Lloyd M et al; "Stability of Milk Fat Emulsions. I. Preparation of Model Oil-in-Water Emulsions and Evaluation of Their Stability;" Department of Food Science and Technology; University of California, Davis; Journal of Dairy Science; Vol. 58 No. 9; 1249-1252.

Pillet, Elodie et al; "Liposomes as an alternative to egg yolk in stallion freezing extender;" Theriogenology 77 (2012) 268-279.

Zeron, Y, et al; "The effect of liposomes on thermotropic membrane phase transitions of bovine spermatozoa and oocytes: implications for reducing chilling sensitivity;" Cryobiology 45 (2002 143-152.

Barnes, D. and G. Sato (1980) Methods for growth of cultured cells in serum-free medium. Anal. Biochem. 102: 255-270.

Foote, R. H., C. C. Brockett and M. T. Kaproth (2002). Motility and fertility of bull sperm in 5 whole milk extender containing antioxidants. An Repro Sci 71: 13-23

Pickett, B. W. and Amann, R. P. (1992). Cryopreservation of Semen, ch 83 in Equine Reproduction A. McKinnon and J. L. Voss, eds. pp. 769-789

Thompson, J. et al. Rate-controlled cryopreservation and thawing of mammalian cells, 2011 Protocol Exchange Shalfer, M, Pharmacological considerations in cryopreservation. In Karow AM (ed). Organ Preservation for Transplantation. 2nd edition. New York: Marcel Dekker 1981: 177-212 and modified and expanded by biocor.umn.edu/listing-of-protective-agents D. Barnes and G. Sato 1980, Analytical Biochemistry 102, p 255

Provisional Application Number 61/685,224, filed 14 Mar. 2012, entitled Lipophilic protection of cryopreserved cells.

Thus, the applicant(s) should be understood to have support to claim and make a statement of invention to at least: i) each of the cryopreservation substances and devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC,* 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 20 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The invention claimed is:

1. A process to enhance the cryopreservation of biological cells comprising the steps of:
   assembling a cellular collection containing a plurality of biological cells;
   establishing a lipid containing cryopreservation fluid to be later incorporated with said biological cells in cryopreservation;
   after said step of establishing a lipid containing cryopreservation fluid to be later incorporated with said biological cells in cryopreservation, adding at least 270 j/kg surface energy to substantially all of said lipid in said lipid containing cryopreservation fluid without filtering said lipid containing cryopreservation fluid to create a lipid surface energy increased cryopreservation fluid by the multiplication in the number of discrete lipid droplets in the fluid without changing the total concentration (v/v or w/v) of the lipid relative to the remaining cryopreservation fluid components;

after said step of adding said at least 270 j/kg surface energy to substantially all of said lipid in said lipid containing cryopreservation fluid to create said lipid surface energy increased cryopreservation fluid, mixing substantially all of said lipid surface energy increased cryopreservation fluid and said biological cells to form an energy increased fluidic cryopreservation composite;

removing thermal energy from said fluidic cryopreservation composite;

freezing said fluidic cryopreservation composite by reducing the temperature of said fluidic cryopreservation composite below the freezing point of water; and providing an enhanced post-cryogenic viability for said biological cells as a result from said above steps.

2. A process to enhance the cryopreservation of biological cells as described in claim 1 wherein said step of adding at least 270 j/kg surface energy to said substantially all of said lipid in said lipid containing cryopreservation fluid to create a lipid surface energy increased cryopreservation fluid comprises the step of adding at least 650 j/kg lipid surface energy to said substantially all of said lipid in said lipid containing cryopreservation fluid.

3. A process to enhance the cryopreservation of biological cells as described in claim 1 further comprising the step of drop transforming said lipid in said cryopreservation fluid into droplets numbering at least 50000 times the number of initial drops of said lipids in said lipid containing cryopreservation fluid.

4. A process to enhance the cryopreservation of biological cells as described in claim 1 wherein said step of assembling a cellular collection containing a plurality of biological cells comprises a step chosen from:

assembling a cellular collection containing a plurality of blood cells, assembling a cellular collection containing a plurality of stem cells, assembling a cellular collection containing a plurality of skin cells, assembling a cellular collection containing a plurality of embryonic stem cells, assembling a cellular collection containing a plurality of neural stem cells, assembling a cellular collection containing a plurality of epithelial stem cells, assembling a cellular collection containing a plurality of cardiac stem cells, assembling a cellular collection containing a plurality of muscle stem cells, assembling a cellular collection containing a plurality of connective stem cells, assembling a cellular collection containing a plurality of epithelial cells, assembling a cellular collection containing a plurality of cardiac cells, assembling a cellular collection containing a plurality of muscle cells, assembling a cellular collection containing a plurality of connective cells, assembling a cellular collection containing a plurality of nerve cells, assembling a cellular collection containing a plurality of umbilical cord blood cells, assembling a cellular collection containing a plurality of live histological sample cells, assembling a cellular collection containing a plurality of plant seed cells, assembling a cellular collection containing a plurality of plant shoot cells, assembling a cellular collection containing a plurality of ovarian tissue cells, assembling a cellular collection containing a plurality of testicular tissue cells, assembling a cellular collection containing a plurality of embryo cells, assembling a cellular collection containing a plurality of tumorous tissue cells, assembling a cellular collection containing a plurality of yeast cells, assembling a cellular collection containing a plurality of bacterial cells, assembling a cellular collection containing a plurality of algal cells, assembling a cellular collection containing a plurality of fungal cells, assembling a cellular collection containing a plurality of mesenchymal cells, assembling a cellular collection containing a plurality of keratinocytes, assembling a cellular collection containing a plurality of melanocytes, assembling a cellular collection containing a plurality of hepatocytes, assembling a cellular collection containing a plurality of oocytes, and assembling a cellular collection containing a plurality of sperm.

5. A process to enhance the cryopreservation of biological cells comprising the steps of:

assembling a cellular collection containing a plurality of biological cells;

establishing a cryopreservation fluid having a lipid therein to be later incorporated with said biological cells in cryopreservation;

after said step of establishing a cryopreservation fluid having said lipid therein to be later incorporated with said biological cells in cryopreservation, in situ sizing substantially all of said lipid within said cryopreservation fluid without filtering said lipid in said cryopreservation fluid to create droplets of a desired droplet size of said lipid substance within said cryopreservation fluid;

retaining substantially all of said droplets of said lipid within said cryopreservation fluid;

after said step of in situ sizing substantially all of said lipid within said cryopreservation fluid to create droplets of said desired droplet size of said lipid substance within said cryopreservation fluid, mixing substantially all of said cryopreservation fluid and said biological cells to form a fluidic cryopreservation composite;

removing thermal energy from said fluidic cryopreservation composite; and freezing said fluidic cryopreservation composite by reducing the temperature of said fluidic cryopreservation composite below the freezing point of water.

6. A process to enhance the cryopreservation of biological cells as described in claim 5 wherein said step of assembling a cellular collection containing a plurality of biological cells comprises a step chosen from:

assembling a cellular collection containing a plurality of blood cells,
assembling a cellular collection containing a plurality of stem cells,
assembling a cellular collection containing a plurality of skin cells,
assembling a cellular collection containing a plurality of embryonic stem cells,
assembling a cellular collection containing a plurality of neural stem cells,
assembling a cellular collection containing a plurality of epithelial stem cells,
assembling a cellular collection containing a plurality of cardiac stem cells,
assembling a cellular collection containing a plurality of muscle stem cells,
assembling a cellular collection containing a plurality of connective stem cells,
assembling a cellular collection containing a plurality of epithelial cells,
assembling a cellular collection containing a plurality of cardiac cells,
assembling a cellular collection containing a plurality of muscle cells,
assembling a cellular collection containing a plurality of connective cells,
assembling a cellular collection containing a plurality of nerve cells,
assembling a cellular collection containing a plurality of umbilical cord blood cells,
assembling a cellular collection containing a plurality of live histological sample cells,
assembling a cellular collection containing a plurality of plant seed cells,
assembling a cellular collection containing a plurality of plant shoot cells,
assembling a cellular collection containing a plurality of ovarian tissue cells,
assembling a cellular collection containing a plurality of testicular tissue cells,
assembling a cellular collection containing a plurality of embryo cells,
assembling a cellular collection containing a plurality of tumorous tissue cells,
assembling a cellular collection containing a plurality of yeast cells,
assembling a cellular collection containing a plurality of bacterial cells,
assembling a cellular collection containing a plurality of algal cells,
assembling a cellular collection containing a plurality of fungal cells,
assembling a cellular collection containing a plurality of mesenchymal cells,
assembling a cellular collection containing a plurality of keratinocytes,
assembling a cellular collection containing a plurality of melanocytes,
assembling a cellular collection containing a plurality of hepatocytes,
assembling a cellular collection containing a plurality of oocytes, and
assembling a cellular collection containing a plurality of sperm.

7. A process to enhance the cryopreservation of biological cells as described in claim 5 wherein said step of in situ sizing substantially all of said lipid within said cryopreservation fluid to create droplets of a desired droplet size of said lipid substance within said cryopreservation fluid comprises a step chosen from:
   in situ creating a substantial number of droplets of a lipid substance contained within said cryopreservation fluid with no substantial amount of droplets larger than at least 1000 nm,
   in situ creating a substantial number of droplets of a lipid substance contained within said cryopreservation fluid with no substantial amount of droplets larger than at least 900 nm,
   in situ creating a substantial number of droplets of a lipid substance contained within said cryopreservation fluid with no substantial amount of droplets larger than at least 700 nm,
   in situ creating a substantial number of droplets of a lipid substance contained within said cryopreservation fluid with no substantial amount of droplets larger than at least 500 nm,
   in situ creating a substantial number of droplets of a lipid substance contained within said cryopreservation fluid with no substantial amount of droplets larger than at least 300 nm,
   in situ creating a substantial number of droplets of a lipid substance contained within said cryopreservation fluid with no substantial amount of droplets larger than at least 100 nm,
   in situ creating a substantial number of droplets of a lipid substance contained within said cryopreservation fluid with no substantial amount of droplets larger than at least 70 nm,
   in situ creating a substantial number of droplets of a lipid substance contained within said cryopreservation fluid with no substantial amount of droplets larger than at least 50 nm, and
   in situ creating a substantial number of droplets of a lipid substance contained within said cryopreservation fluid with no substantial amount of droplets larger than at least 30 nm.

8. A process to enhance the cryopreservation of biological cells as described in claim 5 wherein said step of in situ sizing substantially all of said lipid within said cryopreservation fluid to create droplets of a desired droplet size of said lipid substance within said cryopreservation fluid comprises the step of in situ causing a substance contained within said cryopreservation fluid to have a droplet size with a skewed size distribution that favors smaller size droplets.

9. A process to enhance the cryopreservation of biological cells as described in claim 8 wherein the step of in situ causing a substance contained within said cryopreservation fluid having a droplet size with a skewed size distribution that favors smaller size droplets comprises a step chosen from:
   in situ modifying a substance contained within said cryopreservation fluid to have a mode drop size of less than at least 1000 nm,
   in situ modifying a substance contained within said cryopreservation fluid to have a mode drop size of less than at least 900 nm,
   in situ modifying a substance contained within said cryopreservation fluid to have a mode drop size of less than at least 700 nm,
   in situ modifying a substance contained within said cryopreservation fluid to have a mode drop size of less than at least 500 nm, in situ modifying a substance contained within said cryopreservation fluid to have a mode drop size of less than at least 300 nm, in situ modifying a substance contained within said cryopreservation fluid to have a mode drop size of less than at least 100 nm, in situ modifying a substance contained within said cryopreservation fluid to have a mode drop size of less than at least 70 nm, in situ modifying a substance contained within said cryopreservation fluid to have a mode drop size of less than at least 50 nm, and in situ modifying a substance contained within said cryopreservation fluid to have a mode drop size of less than at least 30 nm.

10. A process to enhance the cryopreservation of biological cells as described in claim 5 and further comprising the step of:

adding energy to said cryopreservation fluid to create an energy increased cryopreservation fluid;

wherein said step of mixing substantially all of said cryopreservation fluid and said biological cells to form a fluidic cryopreservation composite comprises the step of mixing said energy increased cryopreservation fluid and said biological cells to form an energy increased fluidic cryopreservation composite.

11. A process to enhance the cryopreservation of biological cells as described in claim 10 wherein said step of adding energy to said cryopreservation fluid to create an energy increased cryopreservation fluid comprises a step chosen from:

increasing a surface energy of a substance in said cryopreservation fluid to at least 200 j/kg surface energy, increasing a surface energy of a substance in said cryopreservation fluid to at least 420 j/kg surface energy, increasing a surface energy of a substance in said cryopreservation fluid to at least 760 j/kg surface energy, increasing a surface energy of a substance in said cryopreservation fluid to at least 1200 j/kg surface energy, increasing a surface energy of a substance in said cryopreservation fluid to at least 3800 j/kg surface energy, and increasing a surface energy of a substance in said cryopreservation fluid to at least 5400 j/kg surface energy.

12. A process to enhance the cryopreservation of biological cells as described in claim 5 and further comprising the step of:

establishing non-naturally occurring lipid droplets within said cryopreservation fluid to create a non-natural lipid droplet containing cryopreservation fluid;

wherein said step of mixing substantially all of said cryopreservation fluid and said biological cells to form a fluidic cryopreservation composite comprises the step of mixing substantially all of said non-natural lipid containing cryopreservation fluid and said biological cells to form a non-natural fluidic cryopreservation composite.

13. A process to enhance the cryopreservation of biological cells as described in claim 5 wherein said lipid is chosen from: sea buckthorn lipid, saturated fatty acid, unsaturated fatty acid, palmitic acid, palmitoleic acid, oleic acid, linoleic acid, linolenic acid, lecithin, β-sitosterol, β-amyrin, γ-carotene, α-amyrin, β-carotene, lycopene, lutein, tocopherol, digalactosyldiacylglycerol, monogalactosymonoacylglycerol, 16:1 fatty acids, 18:1 fatty acids, 18:2 fatty acids, and 18:3 fatty acid.

14. A process to enhance the cryopreservation of biological cells as described in claim 1 wherein said step of establishing said lipid containing cryopreservation fluid to be incorporated with said biological cells comprises the step of establishing a lipid chosen from: sea buckthorn lipid, saturated fatty acid, unsaturated fatty acid, palmitic acid, palmitoleic acid, oleic acid, linoleic acid, linolenic acid, lecithin, β-sitosterol, β-amyrin, γ-carotene, α-amyrin, β-carotene, lycopene, lutein, tocopherol, digalactosyldiacylglycerol, monogalactosymonoacylglycerol, 16:1 fatty acids, 18:1 fatty acids, 18:2 fatty acids, and 18:3 fatty acid.

15. A process to enhance the cryopreservation of biological cells as described in claim 1 and further comprising the steps of:

establishing non-naturally occurring lipid droplets within said cryopreservation fluid to create a non-natural lipid droplet containing cryopreservation fluid; and mixing said non-natural lipid droplet containing cryopreservation fluid and said biological cells to form a non-natural fluidic cryopreservation composite.

16. A process to enhance the cryopreservation of biological cells as described in claim 1 and further comprising the step of in situ sizing droplets of at least one substance within said cryopreservation fluid.

17. A process to enhance the cryopreservation of biological cells as described in claim 10 wherein said step of adding energy to said cryopreservation fluid comprises the step of adding surface energy to said lipid in said cryopreservation fluid to create a substantially surface energy enhanced cryopreservation fluid chosen from:

increasing a surface energy of a lipid substance in said cryopreservation fluid to at least 200 j/kg surface energy, increasing a surface energy of a lipid substance in said cryopreservation fluid to at least 420 j/kg surface energy, increasing a surface energy of a lipid substance in said cryopreservation fluid to at least 760 j/kg surface energy, increasing a surface energy of a lipid substance in said cryopreservation fluid to at least 1200 j/kg surface energy, increasing a surface energy of a lipid substance in said cryopreservation fluid to at least 3800 j/kg surface energy, and increasing a surface energy of a lipid substance in said cryopreservation fluid to at least 5400 j/kg surface energy.

18. A process to enhance the cryopreservation of biological cells as described in claim 1 and further comprising the step of excluding adding detergents and salts to said lipid containing cryopreservation fluid during said step of adding at least 270 j/kg surface energy to said substantially all of said lipid in said lipid containing cryopreservation fluid to create said lipid surface energy increased cryopreservation fluid.

19. A process to enhance the cryopreservation of biological cells as described in claim 5 and further comprising the step of excluding adding detergents and salts to said cryopreservation fluid during said step of in situ sizing substantially all of said lipid within said cryopreservation fluid to create droplets of said desired droplet size of said lipid substance within said cryopreservation fluid.

20. A process to enhance the cryopreservation of biological cells as described in claim 1 and wherein said step of adding said at least 270 j/kg surface energy to substantially all of said lipid in said lipid containing cryopreservation fluid to create said lipid surface energy increased cryopreservation fluid comprises the step of adding said at least 270 j/kg surface energy by a process selected from a group consisting of sonication, physical dispersion, shearing, cavitation, pressing, mechanical mixing, and any combination thereof.

21. A process to enhance the cryopreservation of biological cells as described in claim 5 wherein said step of in situ sizing substantially all of said lipid within said cryopreservation fluid to create droplets of said desired droplet size of said lipid substance within said cryopreservation fluid comprises the step of in situ sizing substantially all of said lipid within said cryopreservation fluid by a process selected from a group consisting of sonication, physical dispersion, shearing, cavitation, pressing, mechanical mixing, and any combination thereof.

* * * * *